(12) United States Patent
Yadav et al.

(10) Patent No.: US 7,504,259 B2
(45) Date of Patent: Mar. 17, 2009

(54) Δ12 DESATURASES SUITABLE FOR ALTERING LEVELS OF POLYUNSATURATED FATTY ACIDS IN OLEAGINOUS YEAST

(75) Inventors: Narendra S. Yadav, Wilmington, DE (US); Quinn Qun Zhu, West Chester, PA (US); Hongxiang Zhang, Chadds Ford, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 86 days.

(21) Appl. No.: 10/985,691

(22) Filed: Nov. 10, 2004

(65) Prior Publication Data
US 2005/0216975 A1 Sep. 29, 2005

Related U.S. Application Data

(60) Provisional application No. 60/519,191, filed on Nov. 12, 2003, provisional application No. 60/570,679, filed on May 13, 2004.

(51) Int. Cl.
*C12N 15/74* (2006.01)
*C07H 21/04* (2006.01)

(52) U.S. Cl. ............... 435/471; 536/23.2; 536/23.74

(58) Field of Classification Search ............... None
See application file for complete search history.

(56) References Cited

U.S. PATENT DOCUMENTS

| | | | |
|---|---|---|---|
| 6,075,183 A | 6/2000 | Knutzon et al. | |
| 6,136,574 A | 10/2000 | Knutzon et al. | |
| 6,372,965 B1 | 4/2002 | Lightner et al. | |
| 6,872,872 B1 | 3/2005 | Lightner et al. | |
| 6,902,887 B1 * | 6/2005 | Berka et al. ............... | 435/6 |
| 6,919,466 B2 | 7/2005 | Lightner et al. | |
| 2005/0266537 A1 | 12/2005 | Chen | |

FOREIGN PATENT DOCUMENTS

| | | |
|---|---|---|
| EP | 0 005 277 B1 | 11/1979 |
| WO | 03064596 A2 | 8/2003 |
| WO | WO 03/099216 A1 | 12/2003 |

OTHER PUBLICATIONS

Broun et al, Science 282: 1315-1317, Nov. 13, 1998.*
Van de Loo et al, PNAS, USA 92: 6743-6747, Jul. 1995.*
Doerks et al, TIG 14(6): 248-250, Jun. 1998.*
Smith et al, Nature Biotechnology 15: 1222-1223, Nov. 15, 1997.*
Brenner, S.E., TIG 15(4): 132-133, Apr. 1999.*
Bork et al, TIG 12(10): 425-427, Oct. 1996.*
DeLuca, V, AgBiotech News and Information 5(6): 225N-229N, 1993.*
U.S. Appl. No. 10/985,254, filed Nov. 10, 2004, Yadav.
J. M. Dyer et al., Metabolic engineering of *Saccharomyces cerevisiae* for production of novel lipid compounds, Appl. Microbiol. Biotechnol., vol. 59:224-230, 2002.
Frederic Domergue et al., Cloning and Functional characterization of *Phaeodactylum tricornutum* front-end desaturases involved in eicosapentaenoic acid biosynthesis, Eur. J. Biochem., vol. 269:4105-4113, 2002.
Frederic Beaudoin et al., Heterologous reconstitution in yeast of the polyunsaturated fatty acid biosynthetic pathway, PNAS, vol. 97(12):6421-6426, 2000.
Eiji Sakuradani et al., Identification of alpha 12-fatty acid desaturase from arachidonic acid-producing *Mortierella* fungus by heterologous expression in the yeast *Saccharomyces cerevisiae* and the fungus *Aspergillus oryzae*, Eur. J. Biochem., vol. 261:812-820, 1999.
Colin Ratledge, Microbial Oils and Fats: An Assessment of Their Commercial Potential, Prog. Ind. Microbiol., vol. 16:119-206, 1982.
Berka et al., *Fusarium venenatum*, Accession No. AAF08056, Mar. 13, 2001.
Calvo, Ana M., Genetic Connection Between Fatty Acid Metabolism and Sporulation in *Aspergillus nidulans*, The Journal of Biological Chemistry, Jul. 13, 2001, p. 25766-25774, vol. 276, No. 28.

* cited by examiner

*Primary Examiner*—Elizabeth F McElwain
(74) *Attorney, Agent, or Firm*—Loretta Smith; Neil Feltham

(57) ABSTRACT

The present invention relates to fungal Δ12 fatty acid desaturases that are able to catalyze the conversion of oleic acid to linoleic acid (LA; 18:2). Nucleic acid sequences encoding the desaturases, nucleic acid sequences which hybridize thereto, DNA constructs comprising the desaturase genes, and recombinant host microorganisms expressing increased levels of the desaturases are described. Methods of increasing production of specific ω-3 and ω-6 fatty acids by over-expression of the Δ12 fatty acid desaturases are also described herein.

6 Claims, 9 Drawing Sheets

From

| Pain Distances of Untitled ClustalW (Slow/Accurate, Gonnet) | | | | | | | | | | | | |
|---|---|---|---|---|---|---|---|---|---|---|---|---|
| Percent Similarity in upper triangle | | | | | | | | | | | | |
| Percent Divergence in lower triangle | | | | | | | | | | | | |
|  | Nc1 | Fg1 | Fm1 | Mg1 | An1 | Y1 dl2d | Nc2 | Fg2 | Fm2 | Mg2 | An2 | |
| Nc1 | *** | 55.2 | 54.8 | 56.2 | 46.2 | 35.9 | 40.3 | 40.1 | 40.3 | 41.5 | 39.6 | Nc1 |
| Fg1 | 59.0 | *** | 88.8 | 59.8 | 46.2 | 40.2 | 43.7 | 42.4 | 42.4 | 43.9 | 44.4 | Fg1 |
| Fm1 | 59.8 | 11.9 | *** | 60.9 | 46.8 | 42.0 | 43.8 | 43.8 | 43.5 | 43.5 | 44.5 | Fm1 |
| Mg1 | 54.2 | 53.3 | 51.0 | *** | 48.0 | 41.1 | 45.2 | 43.7 | 43.1 | 42.1 | 42.6 | Mg1 |
| An1 | 78.8 | 84.8 | 83.0 | 81.6 | *** | 38.9 | 43.4 | 41.6 | 40.4 | 42.4 | 40.6 | An1 |
| Y1 dl2d | 116.2 | 103.6 | 97.1 | 102.4 | 109.1 | *** | 52.5 | 52.3 | 51.3 | 53.0 | 53.0 | Y1 dl2d |
| Nc2 | 109.2 | 97.8 | 97.5 | 93.0 | 98.4 | 73.4 | *** | 65.8 | 67.6 | 69.7 | 66.4 | Nc2 |
| Fg2 | 103.7 | 99.4 | 95.0 | 97.9 | 104.0 | 72.1 | 39.1 | *** | 95.0 | 72.1 | 61.6 | Fg2 |
| Fm2 | 108.8 | 102.0 | 98.3 | 99.6 | 108.9 | 76.4 | 41.0 | 5.2 | *** | 70.0 | 61.2 | Fm2 |
| Mg2 | 104.6 | 97.0 | 98.3 | 103.0 | 101.7 | 72.2 | 38.3 | 34.8 | 38.2 | *** | 56.3 | Mg2 |
| An2 | 111.1 | 95.4 | 95.1 | 101.3 | 107.9 | 71.9 | 42.0 | 52.2 | 52.6 | 45.7 | *** | An2 |

FIG. 5

|  |  | 1 | 2 | 3 | 4 | 5 | 6 | 7 | 8 | 9 | 10 | 11 | 12 | 13 | 14 | 15 | 16 | 17 | 18 | 19 | 20 | 21 |  |  |
|---|---|---|---|---|---|---|---|---|---|---|---|---|---|---|---|---|---|---|---|---|---|---|---|---|
|  |  | Sp d12 | Ce d12 | Cr d12 | Cv d12 | AtM d12 | Yl d12 | Dh d12 | MoA d12 | Mr d12 | Pg d12 | Nc d12 | Fg d12 | Fm d12 | Mg d12 | An d12 | Af d12 | Mg d15 | Fg d15 | Fm d15 | An d15 | Nc d15 |  |  |
| 1 | Sp d12 | *** | 24.2 | 41.0 | 18.2 | 17.9 | 19.7 | 14.8 | 19.7 | 19.9 | 19.5 | 20.5 | 19.4 | 19.9 | 20.5 | 19.7 | 18.2 | 18.2 | 20.0 | 19.9 | 20.8 | 18.5 | Sp d12 | 1 |
| 2 | Ce d12 |  | *** | 18.4 | 26.3 | 26.6 | 22.1 | 17.7 | 25.0 | 24.5 | 24.6 | 25.5 | 26.6 | 25.0 | 25.8 | 23.9 | 24.5 | 27.4 | 25.3 | 25.0 | 25.5 | 27.7 | Ce d12 | 2 |
| 3 | Cr d12 |  |  | *** | 19.4 | 20.4 | 20.3 | 11.0 | 19.0 | 15.9 | 21.0 | 19.6 | 17.2 | 19.8 | 17.5 | 14.8 | 14.2 | 14.0 | 18.2 | 17.9 | 17.2 | 17.0 | Cr d12 | 3 |
| 4 | Cv d12 |  |  |  | *** | 50.8 | 35.4 | 27.4 | 41.8 | 37.0 | 35.3 | 41.0 | 40.7 | 40.2 | 40.7 | 39.4 | 39.4 | 39.4 | 38.6 | 39.1 | 39.5 | 37.8 | Cv d12 | 4 |
| 5 | AtM d12 |  |  |  |  | *** | 37.3 | 25.3 | 40.5 | 35.8 | 36.8 | 40.7 | 40.5 | 41.3 | 39.7 | 39.7 | 38.9 | 36.3 | 34.7 | 35.2 | 40.1 | 37.1 | AtM d12 | 5 |
| 6 | Yl d12 |  |  |  |  |  | *** | 38.8 | 38.6 | 36.1 | 49.1 | 51.1 | 49.6 | 48.7 | 50.6 | 51.6 | 51.6 | 39.6 | 40.3 | 41.5 | 40.1 | 34.8 | Yl d12 | 6 |
| 7 | Dh d12 |  |  |  |  |  |  | *** | 30.0 | 27.4 | 27.8 | 38.8 | 36.7 | 38.4 | 42.6 | 38.8 | 38.4 | 30.0 | 30.0 | 30.0 | 28.7 | 34.6 | Dh d12 | 7 |
| 8 | MoA d12 |  |  |  |  |  |  |  | *** | 50.8 | 39.5 | 43.9 | 39.6 | 39.6 | 42.6 | 41.4 | 42.4 | 38.3 | 38.2 | 36.8 | 39.2 | 35.3 | MoA d12 | 8 |
| 9 | Mr d12 |  |  |  |  |  |  |  |  | *** | 35.6 | 39.4 | 37.6 | 37.4 | 41.9 | 38.6 | 36.6 | 34.3 | 31.5 | 31.3 | 36.0 | 32.3 | Mr d12 | 9 |
| 10 | Pg d12 |  |  |  |  |  |  |  |  |  | *** | 49.1 | 47.0 | 46.7 | 51.2 | 49.1 | 49.1 | 38.3 | 38.6 | 39.2 | 34.4 | 37.4 | Pg d12 | 10 |
|  |  |  |  |  |  |  |  |  |  |  |  | *** |  |  |  |  |  | 41.1 | 42.6 | 42.5 | 45.2 | 37.7 | Af d12 | 16 |

FIG. 6

SEQUENCE LISTING

<160> NUMBER OF SEQ ID NOS: 66

<210> SEQ ID NO 1
<211> LENGTH: 1209
<212> TYPE: DNA
<213> ORGANISM: Fusarium monoliforme

<400> SEQUENCE: 1

```
atggcgactc gacagcgaac tgccaccact gttgtggtcg aggaccttcc caaggtcact      60
cttgaggcca agtctgaacc tgtgttcccc gatatcaaga ccatcaagga tgccattccc     120
gcgcactgct tccagccctc gctcgtcacc tcattctact acgtcttccg cgattttgcc     180
atggtctctg ccctcgtctg ggctgctctc acctacatcc ccagcatccc cgaccagacc     240
ctccgcgtcg cagcttggat ggtctacggc ttcgtccagg gtctgttctg caccggtgtc     300
tggattctcg gccatgagtg cggccacggt gctttctctc tccacggaaa ggtcaacaat     360
gtgaccggct ggttcctcca ctcgttcctc ctcgtcccct acttcagctg gaagtactct     420
caccaccgcc accaccgctt caccggccac atggatctcg acatggcttt cgtccccaag     480
actgagccca agccctccaa gtcgctcatg attgctggca ttgacgtcgc cgagcttgtt     540
gaggacaccc ccgctgctca gatggtcaag ctcatcttcc accagctttt cggatggcag     600
gcgtacctct tcttcaacgc tagctctggc aagggcagca agcagtggga gcccaagact     660
ggcctctcca agtggttccg agtcagtcac ttcgagccta ccagcgctgt cttccgcccc     720
aacgaggcca tcttcatcct catctccgat atcggtcttg ctctaatggg aactgctctg     780
tactttgctt ccaagcaagt tggtgtttcg accattctct tcctctacct tgttccctac     840
```

-continued

```
ctgtgggttc accactggct cgttgccatt acctacctcc accaccacca caccgagctc    900
cctcactaca ccgctgaggg ctggacctac gtcaagggag ctctcgccac tgtcgaccgt    960
gagtttggct tcatcggaaa gcacctcttc cacggtatca ttgagaagca cgttgttcac   1020
catctcttcc ctaagatccc cttctacaag gctgacgagg ccaccgaggc catcaagccc   1080
gtcattggcg accactactg ccacgacgac cgaagcttcc tgggccagct gtggaccatc   1140
ttcggcacgc tcaagtacgt cgagcacgac cctgcccgac ccggtgccat gcgatggaac   1200
aaggactag                                                           1209

<210> SEQ ID NO 2
<211> LENGTH: 402
<212> TYPE: PRT
<213> ORGANISM: Fusarium monoliforme

<400> SEQUENCE: 2

Met Ala Thr Arg Gln Arg Thr Ala Thr Thr Val Val Val Glu Asp Leu
1               5                   10                  15

Pro Lys Val Thr Leu Glu Ala Lys Ser Glu Pro Val Phe Pro Asp Ile
            20                  25                  30

Lys Thr Ile Lys Asp Ala Ile Pro Ala His Cys Phe Gln Pro Ser Leu
        35                  40                  45

Val Thr Ser Phe Tyr Tyr Val Phe Arg Asp Phe Ala Met Val Ser Ala
    50                  55                  60

Leu Val Trp Ala Ala Leu Thr Tyr Ile Pro Ser Ile Pro Asp Gln Thr
65                  70                  75                  80

Leu Arg Val Ala Ala Trp Met Val Tyr Gly Phe Val Gln Gly Leu Phe
                85                  90                  95

Cys Thr Gly Val Trp Ile Leu Gly His Glu Cys Gly His Gly Ala Phe
            100                 105                 110

Ser Leu His Gly Lys Val Asn Asn Val Thr Gly Trp Phe Leu His Ser
        115                 120                 125

Phe Leu Leu Val Pro Tyr Phe Ser Trp Lys Tyr Ser His His Arg His
    130                 135                 140

His Arg Phe Thr Gly His Met Asp Leu Asp Met Ala Phe Val Pro Lys
145                 150                 155                 160

Thr Glu Pro Lys Pro Ser Lys Ser Leu Met Ile Ala Gly Ile Asp Val
                165                 170                 175

Ala Glu Leu Val Glu Asp Thr Pro Ala Ala Gln Met Val Lys Leu Ile
            180                 185                 190

Phe His Gln Leu Phe Gly Trp Gln Ala Tyr Leu Phe Phe Asn Ala Ser
        195                 200                 205

Ser Gly Lys Gly Ser Lys Gln Trp Glu Pro Lys Thr Gly Leu Ser Lys
    210                 215                 220

Trp Phe Arg Val Ser His Phe Glu Pro Thr Ser Ala Val Phe Arg Pro
225                 230                 235                 240

Asn Glu Ala Ile Phe Ile Leu Ile Ser Asp Ile Gly Leu Ala Leu Met
                245                 250                 255

Gly Thr Ala Leu Tyr Phe Ala Ser Lys Gln Val Gly Val Ser Thr Ile
            260                 265                 270

Leu Phe Leu Tyr Leu Val Pro Tyr Leu Trp Val His His Trp Leu Val
        275                 280                 285

Ala Ile Thr Tyr Leu His His His His Thr Glu Leu Pro His Tyr Thr
    290                 295                 300
```

```
Ala Glu Gly Trp Thr Tyr Val Lys Gly Ala Leu Ala Thr Val Asp Arg
305                 310                 315                 320

Glu Phe Gly Phe Ile Gly Lys His Leu Phe His Gly Ile Ile Glu Lys
            325                 330                 335

His Val Val His His Leu Phe Pro Lys Ile Pro Phe Tyr Lys Ala Asp
                340                 345                 350

Glu Ala Thr Glu Ala Ile Lys Pro Val Ile Gly Asp His Tyr Cys His
            355                 360                 365

Asp Asp Arg Ser Phe Leu Gly Gln Leu Trp Thr Ile Phe Gly Thr Leu
    370                 375                 380

Lys Tyr Val Glu His Asp Pro Ala Arg Pro Gly Ala Met Arg Trp Asn
385                 390                 395                 400

Lys Asp

<210> SEQ ID NO 3
<211> LENGTH: 1434
<212> TYPE: DNA
<213> ORGANISM: Fusarium monoliforme

<400> SEQUENCE: 3
atggcgtcca cttcggctct gcccaagcag aaccctgcgc ttagacgcac cgtcacctca      60
actactgtga cggattctga gtctgccgcc gtctctcctt cagactctcc ccgccactcg     120
gcctcttcca catcgctctc gtccatgtcc gaggttgata tcgccaagcc caagtccgag     180
tatggtgtca tgctcgacac ctacggcaac cagttcgagg ttcccgactt taccatcaag     240
gacatctaca tgccatccc taagcactgc ttcaagcgct ccgctctcaa gggatacggt     300
tatatcctcc gcgacattgt cctcctgact accactttca gcatctggta caactttgtg     360 accccgaat atatcccctc cacccccgcc cgcgctggtc tgtgggccgt gtacaccgtt     420
cttcagggtc ttttcggtac tggtctctgg gttattgccc atgagtgcgg tcacggtgct     480
ttctccgatt ctcgcatcat caacgacatt actggctggg ttcttcactc ttccctcctt     540
gtcccctact tcagctggca aatctcccac cgaaagcacc acaaggccac tggcaacatg     600
gagcgtgaca tggtcttcgt tccccgaacc cgcgagcagc aggctactcg tctcggaaag     660
atgacccacg agtcgctcca tcttactgag gagaccccg ctttcactct ctcatgctc      720 gtccttcagc agctcgttgg ctggcccaac tacctcatca ccaatgttac cggccacaac     780
taccacgagc gccagcgtga gggtcgcggc aagggcaagc ataacggcct cggcggtggt     840
gttaaccact cgatccccg cagccctctg tacgagaaca gtgacgctaa gctcatcgtc     900
ctcagcgata ttggtatcgg tctgatggcc actgctctgt acttcctcgt tcagaagttc     960
ggtttctaca catggccat ctggtacttt gttccctacc tctgggttaa ccactggctc    1020
gttgccatca ccttcctcca gcacaccgac cctaccccttc cccactacac caacgacgag    1080
tggaacttcg tccgtggtgc cgctgctacc attgaccgtg agatgggctt catcggccgc    1140
caccttctcc acggcatcat cgagactcat gtcctccacc actacgtcag cagcatcccc    1200
ttctacaacg cggacgaggc caccgaggcc attaagccca tcatgggcaa gcactaccgg    1260
gctgatgtcc aggatggtcc tcgtggcttc atccgcgcca tgtaccgcag tgcgcgtatg    1320
tgccagtggg ttgagcccag cgctggtgcc gagggtgctg gtaagggtgt tctgttcttc    1380
cgcaaccgca caacgtggg cacccccccc gctgttatca gcccgttgc  ttaa         1434

<210> SEQ ID NO 4
```

-continued

<211> LENGTH: 477
<212> TYPE: PRT
<213> ORGANISM: Fusarium monoliforme

<400> SEQUENCE: 4

```
Met Ala Ser Thr Ser Ala Leu Pro Lys Gln Asn Pro Ala Leu Arg Arg
1               5                   10                  15

Thr Val Thr Ser Thr Thr Val Thr Asp Ser Glu Ser Ala Ala Val Ser
            20                  25                  30

Pro Ser Asp Ser Pro Arg His Ser Ala Ser Ser Thr Ser Leu Ser Ser
        35                  40                  45

Met Ser Glu Val Asp Ile Ala Lys Pro Lys Ser Glu Tyr Gly Val Met
    50                  55                  60

Leu Asp Thr Tyr Gly Asn Gln Phe Glu Val Pro Asp Phe Thr Ile Lys
65                  70                  75                  80

Asp Ile Tyr Asn Ala Ile Pro Lys His Cys Phe Lys Arg Ser Ala Leu
                85                  90                  95

Lys Gly Tyr Gly Tyr Ile Leu Arg Asp Ile Val Leu Leu Thr Thr Thr
            100                 105                 110

Phe Ser Ile Trp Tyr Asn Phe Val Thr Pro Glu Tyr Ile Pro Ser Thr
        115                 120                 125

Pro Ala Arg Ala Gly Leu Trp Ala Val Tyr Thr Val Leu Gln Gly Leu
    130                 135                 140

Phe Gly Thr Gly Leu Trp Val Ile Ala His Glu Cys Gly His Gly Ala
145                 150                 155                 160

Phe Ser Asp Ser Arg Ile Ile Asn Asp Ile Thr Gly Trp Val Leu His
                165                 170                 175

Ser Ser Leu Leu Val Pro Tyr Phe Ser Trp Gln Ile Ser His Arg Lys
            180                 185                 190

His His Lys Ala Thr Gly Asn Met Glu Arg Asp Met Val Phe Val Pro
        195                 200                 205

Arg Thr Arg Glu Gln Gln Ala Thr Arg Leu Gly Lys Met Thr His Glu
    210                 215                 220

Leu Ala His Leu Thr Glu Glu Thr Pro Ala Phe Thr Leu Leu Met Leu
225                 230                 235                 240

Val Leu Gln Gln Leu Val Gly Trp Pro Asn Tyr Leu Ile Thr Asn Val
                245                 250                 255

Thr Gly His Asn Tyr His Glu Arg Gln Arg Glu Gly Arg Gly Lys Gly
            260                 265                 270

Lys His Asn Gly Leu Gly Gly Gly Val Asn His Phe Asp Pro Arg Ser
        275                 280                 285

Pro Leu Tyr Glu Asn Ser Asp Ala Lys Leu Ile Val Leu Ser Asp Ile
    290                 295                 300

Gly Ile Gly Leu Met Ala Thr Ala Leu Tyr Phe Leu Val Gln Lys Phe
305                 310                 315                 320

Gly Phe Tyr Asn Met Ala Ile Trp Tyr Phe Val Pro Tyr Leu Trp Val
                325                 330                 335

Asn His Trp Leu Val Ala Ile Thr Phe Leu Gln His Thr Asp Pro Thr
            340                 345                 350

Leu Pro His Tyr Thr Asn Asp Glu Trp Asn Phe Val Arg Gly Ala Ala
        355                 360                 365

Ala Thr Ile Asp Arg Glu Met Gly Phe Ile Gly Arg His Leu Leu His
    370                 375                 380

Gly Ile Ile Glu Thr His Val Leu His His Tyr Val Ser Ser Ile Pro
```

```
                385                 390                 395                 400
       Phe Tyr Asn Ala Asp Glu Ala Thr Glu Ala Ile Lys Pro Ile Met Gly
                       405                 410                 415

Lys His Tyr Arg Ala Asp Val Gln Asp Gly Pro Arg Gly Phe Ile Arg
                       420                 425                 430

Ala Met Tyr Arg Ser Ala Arg Met Cys Gln Trp Val Glu Pro Ser Ala
                       435                 440                 445

Gly Ala Glu Gly Ala Gly Lys Gly Val Leu Phe Phe Arg Asn Arg Asn
                       450                 455                 460

Asn Val Gly Thr Pro Pro Ala Val Ile Lys Pro Val Ala
       465                 470                 475

<210> SEQ ID NO 5
<211> LENGTH: 1206
<212> TYPE: DNA
<213> ORGANISM: Aspergillus nidulans

<400> SEQUENCE: 5
atggctgcaa ctgcaacaac cctagcagag attgaaaaga aaaagaagaa ataactctg       60 cagacaatca aaaatgcgat tcccaaacac tgcttcaacc gctctctcct catttcctct      120
gcctacgtcg tccgcgatct cctctacgcc tccgtcctct tctactttgc cctgcacatt      180
gacaccctct tttcctcgca actcctccgc atcctcgcct ggaccgccta cggtttcatg      240
caaggctgcg tcggcaccgg aatctggatc ctcgcacacg aatgcggcca tggagctttc      300
tccccatacc aaacgtggaa cgatgtcgtc ggatggacat tgcactccct cctgatggtc      360
ccgtatttca gctggaagat cacgcacgct cgacaccacc ggtacacaaa caacacagag      420
cgagatacga catttgtccc ctggacagag aaggaatacg acactcgccc gcgctacttc      480
cctgcctggt ttgagatgtt tgaggacacg cccgtctaca accttattag cctactggcg      540
catcagatcg caggatggca gatgtatctc tgttttttacg ttagcgccgg cgcaaagagt      600
aagcctgtac cgcagggaaa acagagcggg tggtttggag ccagcagag cgccagccac      660 tttgatccgg gcagttcgct gtggacggaa aaccagcggc atctgattgc gatttcggac      720
ctggggttgc tgcttgttgc ggcggcaaat tggtaccttg cgcagcaagt gggcgtgctc      780
cgcatggtgc tgatctatgt tgtgccgtac ttctgggtgc accattggct gtgggcgatc      840
acgtacctcc accacacaca ccctcgatc ccgcactaca ctgatagcac ctggacgttc       900
accaaaggcg ctctgtccac cgtcgaccgc gacttcggtt tcatcgggcg gcatttcttc      960
caccatatca ttgaccacca tgtcgtgcat cacttgttta accggatccc gttctaccat     1020
gccgaggagg cgactaatgc cattattccc gtactcgggg acatgtatca tcgcgaagag     1080
accggcttct tgtggagttt aatggagacg tacaagaact gtcggtttgt aggcgttgaa     1140
aatgatgttg gaaaggaggg cgttttgcat tgggtttttg aggagaagaa gggtgccaaa     1200
gcggaa                                                                1206

<210> SEQ ID NO 6
<211> LENGTH: 401
<212> TYPE: PRT
<213> ORGANISM: Aspergillus nidulans

<400> SEQUENCE: 6

Met Ala Ala Thr Ala Thr Thr Leu Ala Glu Ile Glu Lys Lys Lys Glu
 1               5                  10                  15

Glu Ile Thr Leu Gln Thr Ile Lys Asn Ala Ile Pro Lys His Cys Phe
```

-continued

```
                    20                  25                  30
Asn Arg Ser Leu Leu Ile Ser Ser Ala Tyr Val Val Arg Asp Leu Leu
                35                  40                  45
Tyr Ala Ser Val Leu Phe Tyr Phe Ala Leu His Ile Asp Thr Leu Phe
            50                  55                  60
Ser Ser Gln Leu Leu Arg Ile Leu Ala Trp Thr Ala Tyr Gly Phe Met
65                  70                  75                  80
Gln Gly Cys Val Gly Thr Gly Ile Trp Ile Leu Ala His Glu Cys Gly
                    85                  90                  95
His Gly Ala Phe Ser Pro Tyr Gln Thr Trp Asn Asp Val Val Gly Trp
                100                 105                 110
Thr Leu His Ser Leu Leu Met Val Pro Tyr Phe Ser Trp Lys Ile Thr
                115                 120                 125
His Ala Arg His His Arg Tyr Thr Asn Asn Thr Glu Arg Asp Thr Ala
            130                 135                 140
Phe Val Pro Trp Thr Glu Lys Glu Tyr Asp Thr Arg Pro Arg Tyr Phe
145                 150                 155                 160
Pro Ala Trp Phe Glu Met Phe Glu Asp Thr Pro Val Tyr Asn Leu Ile
                165                 170                 175
Ser Leu Leu Ala His Gln Ile Ala Gly Trp Gln Met Tyr Leu Cys Phe
                180                 185                 190
Tyr Val Ser Ala Gly Ala Lys Ser Lys Pro Val Pro Gln Gly Lys Gln
            195                 200                 205
Ser Gly Trp Phe Gly Gly Gln Gln Ser Ala Ser His Phe Asp Pro Gly
        210                 215                 220
Ser Ser Leu Trp Thr Glu Asn Gln Arg His Leu Ile Ala Ile Ser Asp
225                 230                 235                 240
Leu Gly Leu Leu Leu Val Ala Ala Ala Asn Trp Tyr Leu Ala Gln Gln
                245                 250                 255
Val Gly Val Leu Arg Met Val Leu Ile Tyr Val Val Pro Tyr Phe Trp
                260                 265                 270
Val His His Trp Leu Val Ala Ile Thr Tyr Leu His His Thr His Pro
            275                 280                 285
Ser Ile Pro His Tyr Thr Asp Ser Thr Trp Thr Phe Thr Lys Gly Ala
290                 295                 300
Leu Ser Thr Val Asp Arg Asp Phe Gly Phe Ile Gly Arg His Phe Phe
305                 310                 315                 320
His His Ile Ile Asp His His Val Val His His Leu Phe Asn Arg Ile
                325                 330                 335
Pro Phe Tyr His Ala Glu Glu Ala Thr Asn Ala Ile Ile Pro Val Leu
            340                 345                 350
Gly Asp Met Tyr His Arg Glu Glu Thr Gly Phe Leu Trp Ser Leu Met
        355                 360                 365
Glu Thr Tyr Lys Asn Cys Arg Phe Val Gly Val Glu Asn Asp Val Gly
    370                 375                 380
Lys Glu Gly Val Leu His Trp Val Phe Glu Glu Lys Lys Gly Ala Lys
385                 390                 395                 400
Ala
```

<210> SEQ ID NO 7
<211> LENGTH: 1416
<212> TYPE: DNA
<213> ORGANISM: Aspergillus nidulans

<400> SEQUENCE: 7

```
atgtcgtcta ctgccctccc gaagcgcgtt gcgctgcatc gcaacccgac taccgactct    60
tcggtcccca gctccgtctc ggtctccccg ctggactcgc cccgtcagtc tccgtcgtcg   120
acttcgctct cgtcaatggc ctcggatgcg ggcaagggag acttgggcaa gatgctcgac   180
acctatggca atgagttcaa gatccccgac taccaccatca aggatatccg tgatgccatt   240
ccgtcccact gctacaaccg gtctgctatc aggagtctgt cctatgtctt ccgtgatctc   300
gccgtcctcg cttccgtctt ctacgtcttc cacaaatacg tgaccccgga ccgtccct    360
tcgtacccgg cgcgtgttgc gctgtggact ctctacactg tcgtccaggg tctgttcggt   420
accggtatt ggttcttgc tcacgagtgt ggacaccagg cgttctctac ttccaaggtg   480
ctcaacgaca ctgttggctg gatcctgcat tcggctctgc tggtccccta tttctcgtgg   540
aagatctctc acggcaagca ccacaaggcc accggtaacc tggctcgtga catggtcttc   600
gtccccaaga cccgcgaggt gtacgcctcc cgcatcaaga agaccatcta cgacctgaac   660
gaggtgatgg aggagacccc cttggccact gccacccact ccatcctgca gcagctgttc   720
ggctggcct tgtacctgct caccaacgtt accggtcacg acaaccacga cgccagcct   780
gaaggccgcg gcaagggcaa cgtaacggc tacttcaccg gcgtcaacca cttcaacccc   840
aacagccctc tgttcgaggc caaggacgcc aagctcatca ttctgagtga tatcggcctc   900
gccatcaccg ccagcatcct gtacctgatc ggctccaagt tcggctggat gaacttgctc   960
gtctggtacg gtatccccta cctctgggtg aaccactggc ttgttgccat cacctacctc  1020
cagcacaccg accccactct cccccactac cagcccgagt cctggacctt cgcccgcggt  1080
gccgctgcca ccattgaccg cgagttcggc ttcatcggcc gtcacattct ccacggcatc  1140
atcgagaccc acgtcctcca ccactacgtc agcaccatcc ccttctacca cgccgacgag  1200
gccagcgagg ctatcaagaa ggtcatgggc tcgcactacc gcagcgaggc acacaccggt  1260
cctctgggct tcctcaaggc tctctggacc agcgcccgtg tctgccactg ggtcgagccc  1320
accgaaggca ccaagggcga gaacgctggt gtcttgttct ccgcaacac caacggcatc  1380
ggtgttcctc ccattaagct gaccaagcct aactaa                             1416
```

<210> SEQ ID NO 8
<211> LENGTH: 471
<212> TYPE: PRT
<213> ORGANISM: Aspergillus nidulans

<400> SEQUENCE: 8

```
Met Ser Ser Thr Ala Leu Pro Lys Arg Val Ala Leu His Arg Asn Pro
 1               5                  10                  15

Thr Thr Asp Ser Ser Val Pro Ser Ser Val Ser Pro Leu Asp
             20                  25                  30

Ser Pro Arg Gln Ser Pro Ser Thr Ser Leu Ser Ser Met Ala Ser
         35                  40                  45

Asp Ala Gly Lys Gly Asp Leu Gly Lys Met Leu Asp Thr Tyr Gly Asn
     50                  55                  60

Glu Phe Lys Ile Pro Asp Tyr Thr Ile Lys Asp Ile Arg Asp Ala Ile
65                  70                  75                  80

Pro Ser His Cys Tyr Asn Arg Ser Ala Ile Arg Ser Leu Ser Tyr Val
                 85                  90                  95

Phe Arg Asp Leu Ala Val Leu Ala Ser Val Phe Tyr Val Phe His Lys
            100                 105                 110
```

-continued

```
Tyr Val Thr Pro Glu Thr Val Pro Ser Tyr Pro Ala Arg Val Ala Leu
        115                 120                 125

Trp Thr Leu Tyr Thr Val Val Gln Gly Leu Phe Gly Thr Gly Ile Trp
    130                 135                 140

Val Leu Ala His Glu Cys Gly His Gln Ala Phe Ser Thr Ser Lys Val
145                 150                 155                 160

Leu Asn Asp Thr Val Gly Trp Ile Leu His Ser Ala Leu Leu Val Pro
                165                 170                 175

Tyr Phe Ser Trp Lys Ile Ser His Gly Lys His His Lys Ala Thr Gly
            180                 185                 190

Asn Leu Ala Arg Asp Met Val Phe Val Pro Lys Thr Arg Glu Val Tyr
        195                 200                 205

Ala Ser Arg Ile Lys Lys Thr Ile Tyr Asp Leu Asn Glu Val Met Glu
    210                 215                 220

Glu Thr Pro Leu Ala Thr Ala Thr His Ser Ile Leu Gln Gln Leu Phe
225                 230                 235                 240

Gly Trp Pro Leu Tyr Leu Leu Thr Asn Val Thr Gly His Asp Asn His
                245                 250                 255

Glu Arg Gln Pro Glu Gly Arg Gly Lys Gly Lys Arg Asn Gly Tyr Phe
            260                 265                 270

Thr Gly Val Asn His Phe Asn Pro Asn Ser Pro Leu Phe Glu Ala Lys
        275                 280                 285

Asp Ala Lys Leu Ile Ile Leu Ser Asp Ile Gly Leu Ala Ile Thr Ala
    290                 295                 300

Ser Ile Leu Tyr Leu Ile Gly Ser Lys Phe Gly Trp Met Asn Leu Leu
305                 310                 315                 320

Val Trp Tyr Gly Ile Pro Tyr Leu Trp Val Asn His Trp Leu Val Ala
                325                 330                 335

Ile Thr Tyr Leu Gln His Thr Asp Pro Thr Leu Pro His Tyr Gln Pro
            340                 345                 350

Glu Ser Trp Thr Phe Ala Arg Gly Ala Ala Ala Thr Ile Asp Arg Glu
        355                 360                 365

Phe Gly Phe Ile Gly Arg His Ile Leu His Gly Ile Ile Glu Thr His
    370                 375                 380

Val Leu His His Tyr Val Ser Thr Ile Pro Phe Tyr His Ala Asp Glu
385                 390                 395                 400

Ala Ser Glu Ala Ile Lys Lys Val Met Gly Ser His Tyr Arg Ser Glu
                405                 410                 415

Ala His Thr Gly Pro Leu Gly Phe Leu Lys Ala Leu Trp Thr Ser Ala
            420                 425                 430

Arg Val Cys His Trp Val Glu Pro Thr Glu Gly Thr Lys Gly Glu Asn
        435                 440                 445

Ala Gly Val Leu Phe Phe Arg Asn Thr Asn Gly Ile Gly Val Pro Pro
    450                 455                 460

Ile Lys Leu Thr Lys Pro Asn
465                 470
```

<210> SEQ ID NO 9
<211> LENGTH: 1185
<212> TYPE: DNA
<213> ORGANISM: Magnaporthe grisea

<400> SEQUENCE: 9

```
atgtccacca ccgtcactca gcggccgggc gccgctagcc gcgctgaagc caagcccaag     60
```

```
gagcagcaat tccagacat caacaccatc aggaatgcta tccccgcaca ctgttttgag      120
gcatctctgg tgacttcagt tggttacttg gtgcgagatg tggccctcat caccgctctc     180
ggctgggccg ccttgaccta cattccccaa attccggatt cgactttgcg ctggaccgcc     240
tgggccgctt acggctttgt tcagggtctc tttggcaccg gtctctggat ctgccccac      300
gagtgcggcc acggtgcttt cagcaagcac acgcgcatta acaacattct tggctgggcc     360
gcccactcgg ccctgctggt accgtacttc agctggaagt ctctcacca ccgccaccac      420
aacttcaccg ccacatgga aaggacatg gcctttgtgc cccccaggc tgccgaccgc        480
gagtcccgcg ccagcttgct gtcccgcttc ggcatcgacc tcgaggtctt tgaggatacc     540
cccatctttc agcttgctcg cctcgtgagc caccagctct tcggctggca gacttacctg     600
ctcttcaacg ccacctgcgg caaggagtct ctgcagaaca agggtgccgc gtggttccgc     660
cagagccact ttgagcccac tctgccgtc ttccgctcca gcgaggccct ctacatcgcc      720
atctctgaca ttggcctggc catcgttgcc gccgccatct actggggctc caccaaggtc    780
ggcgccggca ccatgttcct cctctacgcc gttccctaca tgtgggttca ccactggctc     840
gtcgccatca cctaccttca ccacaccaac aaggaggtgc accactacga ggccgacagc     900
tggacctttg tcaagggtgc cgtcgccact gtcgaccgtg actttggttt cattgaccgc     960
cacctgttcc acggtatcat tggaacccac gtcgcccacc atctgttccc tcgcattccc    1020
ttttacaagg cagaggaggc caccgaggcc atcaagcctg tcctcggaga cctttaccac   1080
agcgacaatc gccccttcat gcaggctctg tggagcaact tcaccacctg caagtacgtc    1140
gagaaggacc ccaaggttcc cggcgccatg aggtgggccg attga                      1185
```

<210> SEQ ID NO 10
<211> LENGTH: 394
<212> TYPE: PRT
<213> ORGANISM: Magnaporthe grisea

<400> SEQUENCE: 10

```
Met Ser Thr Thr Val Thr Gln Arg Pro Gly Ala Ala Ser Arg Ala Glu
1               5                   10                  15

Ala Lys Pro Lys Glu Gln Gln Phe Pro Asp Ile Asn Thr Ile Arg Asn
                20                  25                  30

Ala Ile Pro Ala His Cys Phe Glu Ala Ser Leu Val Thr Ser Val Gly
            35                  40                  45

Tyr Leu Val Arg Asp Val Ala Leu Ile Thr Ala Leu Gly Trp Ala Ala
        50                  55                  60

Leu Thr Tyr Ile Pro Gln Ile Pro Asp Ser Thr Leu Arg Trp Thr Ala
65                  70                  75                  80

Trp Ala Ala Tyr Gly Phe Val Gln Gly Leu Phe Gly Thr Gly Leu Trp
                85                  90                  95

Ile Leu Ala His Glu Cys Gly His Gly Ala Phe Ser Lys His Thr Arg
            100                 105                 110

Ile Asn Asn Ile Leu Gly Trp Ala Ala His Ser Ala Leu Leu Val Pro
        115                 120                 125

Tyr Phe Ser Trp Lys Phe Ser His Arg His His Asn Phe Thr Gly
    130                 135                 140

His Met Glu Lys Asp Met Ala Phe Val Pro Pro Gln Ala Ala Asp Arg
145                 150                 155                 160

Glu Ser Arg Ala Ser Leu Leu Ser Arg Phe Gly Ile Asp Leu Glu Val
                165                 170                 175
```

```
Phe Glu Asp Thr Pro Ile Phe Gln Leu Ala Arg Leu Val Ser His Gln
                180                 185                 190
Leu Phe Gly Trp Gln Thr Tyr Leu Leu Phe Asn Ala Thr Cys Gly Lys
            195                 200                 205
Glu Ser Leu Gln Asn Lys Gly Ala Ala Trp Phe Arg Gln Ser His Phe
        210                 215                 220
Glu Pro Thr Ser Ala Val Phe Arg Ser Ser Glu Ala Leu Tyr Ile Ala
225                 230                 235                 240
Ile Ser Asp Ile Gly Leu Ala Ile Val Ala Ala Ile Tyr Trp Gly
                245                 250                 255
Ser Thr Lys Val Gly Ala Gly Thr Met Phe Leu Leu Tyr Ala Val Pro
            260                 265                 270
Tyr Met Trp Val His Trp Leu Val Ala Ile Thr Tyr Leu His His
        275                 280                 285
Thr Asn Lys Glu Val His His Tyr Glu Ala Asp Ser Trp Thr Phe Val
        290                 295                 300
Lys Gly Ala Val Ala Thr Val Asp Arg Asp Phe Gly Phe Ile Asp Arg
305                 310                 315                 320
His Leu Phe His Gly Ile Ile Gly Thr His Val Ala His His Leu Phe
                325                 330                 335
Pro Arg Ile Pro Phe Tyr Lys Ala Glu Glu Ala Thr Glu Ala Ile Lys
            340                 345                 350
Pro Val Leu Gly Asp Leu Tyr His Ser Asp Asn Arg Pro Phe Met Gln
        355                 360                 365
Ala Leu Trp Ser Asn Phe Thr Thr Cys Lys Tyr Val Glu Lys Asp Pro
        370                 375                 380
Lys Val Pro Gly Ala Met Arg Trp Ala Asp
385                 390

<210> SEQ ID NO 11
<211> LENGTH: 1656
<212> TYPE: DNA
<213> ORGANISM: Magnaporthe grisea

<400> SEQUENCE: 11
atgccttcca ccagatcgac cacatcgggc attgcccagg agaagactcc tatgaggcga      60
acgaccacct cggccactgt cgaatcggac gtctcagctc cgggaaccgc tgttcagtcg     120
cctatggact cgccccgcca ctctgcctcg tccacctcac tctcttcact ctcttccgtt     180
gatgcggcgg ccgagaagaa atccaacgag tctgtcggca aactcgtcga cacgtacggc     240
aacacctttg agatccctga cttcaccatc aaggacatcc acgatgccat tccaaagcac     300
tgcttttgaac gctctgctat tcgtagcttg agctacgtcg cccgtgatat ggtcctcctg     360
gcgacgacct tctacgtgtt ccacaactac gtgacaccag agtacattcc ctcgaagccg     420
gctcgtgctg gtctgtgggc catttacacg gtgctccagg cctcttcgg caccggaatc     480
tgggttcttg cccatgagtg tggccaccag gctttctcgc cttccaagac atcaacaac     540
acggttggct ggattctcca ctcgtctctg ctggttccgt acttcagctg gcagatgtca     600
cacagcaagc accacaaggc cactggccat attgagcgcg acatggtctt tgtgccccgc     660
acccgggagg agcacgccag caggatcggc gcatggtcc acgagctgtc ggagttgacc     720
gaggagacgc ctattgccac ccttatccac ttggttgggc agcagctgat cggctggcct     780
ctgtacatca tcactaacaa gaccggtcac aactaccacg agcgccagcg tgagggccgt     840
ggcaagggca agaagaacgg tcttttcact ggcgtcaacc acttcaaccc cagcagccct     900
```

-continued

```
ctgtacgaga acaaggacgc cggaaaggtg cttctcagcg acctgggtgt cggccttgtt      960
atcgctggcc tcgtgtacct ttgccaaact ttcggcaccc agaacatgct ggtttggtac     1020
tttatcccct acctctgggt gaaccactgg ctcgttgcca ttacattcct tcagcacacc     1080
gaccsctcgc ttccgcacta tactgccgag gaatggaact tcgtccgagg tgccgctgcc     1140
acgatcgatc gcgagtttgg cttcgtcggc cgccacctgc ttcacggtat cattgagacc     1200
cacgtcctgc accactatgt cagcacgatc ccctttaca acgccgacga ggctactgat      1260
gccatcaaga aggtgatggg caagcactac cgcagcgaca ctgccggcgg ccctgctggc     1320
ttccttaagt cactctggac gagtagccgc atgtgccaat gggttgagcc cagcgccgag     1380
gctgagggta gtggcaaggg tgtcctgttc ttccgcaacc acaacaagat cggcactcct     1440
cctatcaaga tgtctgctca gaaaattaga ctatgcaatg accttcttgg catgcataag     1500
ggaaagaatc aaatgaatgg atcaagggag cgccgcggcg gacaaagtag tttaaagagg     1560
gtgagaaatc agcgatcgac aaatatgaac gaatcacaca tgacggtgtt ccgggcattc     1620
cgaacttgga gctcatgcac gcgcgcgtcc acatga                               1656
```

<210> SEQ ID NO 12
<211> LENGTH: 551
<212> TYPE: PRT
<213> ORGANISM: Magnaporthe grisea

<400> SEQUENCE: 12

```
Met Pro Ser Thr Arg Ser Thr Thr Ser Gly Ile Ala Gln Glu Lys Thr
  1               5                  10                  15

Pro Met Arg Arg Thr Thr Thr Ser Ala Thr Val Glu Ser Asp Val Ser
             20                  25                  30

Ala Pro Gly Thr Ala Val Gln Ser Pro Met Asp Ser Pro Arg His Ser
         35                  40                  45

Ala Ser Ser Thr Ser Leu Ser Ser Leu Ser Ser Val Asp Ala Ala Ala
     50                  55                  60

Glu Lys Lys Ser Asn Glu Ser Val Gly Lys Leu Val Asp Thr Tyr Gly
 65                  70                  75                  80

Asn Thr Phe Glu Ile Pro Asp Phe Thr Ile Lys Asp Ile His Asp Ala
                 85                  90                  95

Ile Pro Lys His Cys Phe Glu Arg Ser Ala Ile Arg Ser Leu Ser Tyr
            100                 105                 110

Val Ala Arg Asp Met Val Leu Leu Ala Thr Thr Phe Tyr Val Phe His
        115                 120                 125

Asn Tyr Val Thr Pro Glu Tyr Ile Pro Ser Lys Pro Arg Ala Gly
    130                 135                 140

Leu Trp Ala Ile Tyr Thr Val Leu Gln Gly Leu Phe Thr Gly Ile
145                 150                 155                 160

Trp Val Leu Ala His Glu Cys Gly His Gln Ala Phe Ser Pro Ser Lys
                165                 170                 175

Thr Ile Asn Asn Thr Val Gly Trp Ile Leu His Ser Ser Leu Leu Val
            180                 185                 190

Pro Tyr Phe Ser Trp Gln Met Ser His Ser Lys His His Lys Ala Thr
        195                 200                 205

Gly His Ile Glu Arg Asp Met Val Phe Val Pro Arg Thr Arg Glu Glu
    210                 215                 220

His Ala Ser Arg Ile Gly Arg Met Val His Glu Leu Ser Glu Leu Thr
225                 230                 235                 240
```

Glu Glu Thr Pro Ile Ala Thr Leu Ile His Leu Val Gly Gln Gln Leu
            245                 250                 255

Ile Gly Trp Pro Leu Tyr Ile Ile Thr Asn Lys Thr Gly His Asn Tyr
        260                 265                 270

His Glu Arg Gln Arg Glu Gly Arg Gly Lys Gly Lys Lys Asn Gly Leu
    275                 280                 285

Phe Thr Gly Val Asn His Phe Asn Pro Ser Ser Pro Leu Tyr Glu Asn
290                 295                 300

Lys Asp Ala Gly Lys Val Leu Leu Ser Asp Leu Gly Val Gly Leu Val
305                 310                 315                 320

Ile Ala Gly Leu Val Tyr Leu Cys Gln Thr Phe Gly Thr Gln Asn Met
                325                 330                 335

Leu Val Trp Tyr Phe Ile Pro Tyr Leu Trp Val Asn His Trp Leu Val
            340                 345                 350

Ala Ile Thr Phe Leu Gln His Thr Asp Pro Ser Leu Pro His Tyr Thr
        355                 360                 365

Ala Glu Glu Trp Asn Phe Val Arg Gly Ala Ala Thr Ile Asp Arg
    370                 375                 380

Glu Phe Gly Phe Val Gly Arg His Leu Leu His Gly Ile Ile Glu Thr
385                 390                 395                 400

His Val Leu His His Tyr Val Ser Thr Ile Pro Phe Tyr Asn Ala Asp
                405                 410                 415

Glu Ala Thr Asp Ala Ile Lys Lys Val Met Gly Lys His Tyr Arg Ser
            420                 425                 430

Asp Thr Ala Gly Gly Pro Ala Gly Phe Leu Lys Ser Leu Trp Thr Ser
        435                 440                 445

Ser Arg Met Cys Gln Trp Val Glu Pro Ser Ala Glu Ala Glu Gly Ser
    450                 455                 460

Gly Lys Gly Val Leu Phe Phe Arg Asn His Asn Lys Ile Gly Thr Pro
465                 470                 475                 480

Pro Ile Lys Met Ser Ala Gln Lys Ile Arg Leu Cys Asn Asp Leu Leu
                485                 490                 495

Gly Met His Lys Gly Lys Asn Gln Met Asn Gly Ser Arg Glu Arg Arg
            500                 505                 510

Gly Gly Gln Ser Ser Leu Lys Arg Val Arg Asn Gln Arg Ser Thr Asn
        515                 520                 525

Met Asn Glu Ser His Met Thr Val Phe Arg Ala Phe Arg Thr Trp Ser
530                 535                 540

Ser Cys Thr Arg Ala Ser Thr
545                 550

<210> SEQ ID NO 13
<211> LENGTH: 1290
<212> TYPE: DNA
<213> ORGANISM: Neurospora crassa

<400> SEQUENCE: 13
atgacggtca ccacccgcag ccacaaggcc gcggccgcca ccgagcccga ggttgtcagc    60
accggcgttg acgccgtctc tgctgctgct cctcctcct cctcctcctc ttccagccaa   120
aagtcggccg agcccatcga ataccccgac atcaagacca tccgcgacgc catccccgac   180
cactgcttcc gccgcgcgt ctggatctcc atggcctact tcatccgcga cttcgccatg   240
gcctttggcc tcggctacct cgcctggcag tacatccccc tgatcgcctc caccccgctc   300

-continued

```
cgctacggcg cctgggctct gtacggctac ctccagggtc tcgtctgcac gggcatctgg    360
attctggcgc acgagtgcgg ccacggcgcc ttctcgaggc acacgtggtt caacaacgtc    420
atggggtgga ttggccactc cttcctcttg gtcccttact tcagctggaa gttcagccac    480
catcgccacc atcgcttcac cggccacatg agaaggaca  tggcgtttgt gcctgccacc    540
gaggctgatc gcaaccagag gaagctggcc aacttgtaca tggacaagga cacggccgag    600
atgtttgag  atgtgcccat tgtccagctc gtcaagctca tcgcccacca gctggccggc    660
tggcagatgt acctcctctt caacgtctcc gccggtaagg gcagcaagca gtgggagact    720
ggcaagggcg gcatgggctg gttgagggtt agccactttg agccttcctc tgctgtgttc    780
cgcaactccg aggccatcta cattgccctg tccgatcttg gtctcatgat catgggctat    840
atcctctacc aggccgcgca ggttgttggc tggcagatgg taggtctgct gtacttccag    900
cagtacttct gggttcacca ttggttggtc gccatcactt acctccacca cacccacgag    960
gaagtccacc actttgacgc cgactcgtgg accttcgtca agggcgctct cgccaccgtc   1020
gaccgcgatt ttggcttcat tggcaagcac ctcttccaca acattatcga ccaccacgtc   1080
gtccaccact tgttccctcg catcccttc  tactacgccg aagaagccac caactcgatc   1140
cgccccatgc tcggcccct  ctaccaccgc gacgaccgct ccttcatggg ccagctgtgg   1200
tacaacttca cccactgcaa gtgggtcgtt ccggaccccc aggtccccgg cgcgcttatt   1260
tgggcgcaca ccgttcagag cacccagtaa                                    1290
```

<210> SEQ ID NO 14
<211> LENGTH: 429
<212> TYPE: PRT
<213> ORGANISM: Neurospora crassa

<400> SEQUENCE: 14

```
Met Thr Val Thr Thr Arg Ser His Lys Ala Ala Ala Thr Glu Pro
1               5                   10                  15

Glu Val Val Ser Thr Gly Val Asp Ala Val Ser Ala Ala Pro Ser
                20                  25                  30

Ser Ser Ser Ser Ser Ser Gln Lys Ser Ala Glu Pro Ile Glu Tyr
                35                  40                  45

Pro Asp Ile Lys Thr Ile Arg Asp Ala Ile Pro Asp His Cys Phe Arg
50                  55                  60

Pro Arg Val Trp Ile Ser Met Ala Tyr Phe Ile Arg Asp Phe Ala Met
65                  70                  75                  80

Ala Phe Gly Leu Gly Tyr Leu Ala Trp Gln Tyr Ile Pro Leu Ile Ala
                85                  90                  95

Ser Thr Pro Leu Arg Tyr Gly Ala Trp Ala Leu Tyr Gly Tyr Leu Gln
                100                 105                 110

Gly Leu Val Cys Thr Gly Ile Trp Ile Leu Ala His Glu Cys Gly His
                115                 120                 125

Gly Ala Phe Ser Arg His Thr Trp Phe Asn Asn Val Met Gly Trp Ile
                130                 135                 140

Gly His Ser Phe Leu Leu Val Pro Tyr Phe Ser Trp Lys Phe Ser His
145                 150                 155                 160

His Arg His His Arg Phe Thr Gly His Met Glu Lys Asp Met Ala Phe
                165                 170                 175

Val Pro Ala Thr Glu Ala Asp Arg Asn Gln Arg Lys Leu Ala Asn Leu
                180                 185                 190

Tyr Met Asp Lys Glu Thr Ala Glu Met Phe Glu Asp Val Pro Ile Val
```

```
                195                 200                 205
Gln Leu Val Lys Leu Ile Ala His Gln Leu Ala Gly Trp Gln Met Tyr
    210                 215                 220

Leu Leu Phe Asn Val Ser Ala Gly Lys Gly Ser Lys Gln Trp Glu Thr
225                 230                 235                 240

Gly Lys Gly Gly Met Gly Trp Leu Arg Val Ser His Phe Glu Pro Ser
                245                 250                 255

Ser Ala Val Phe Arg Asn Ser Glu Ala Ile Tyr Ile Ala Leu Ser Asp
                260                 265                 270

Leu Gly Leu Met Ile Met Gly Tyr Ile Leu Tyr Gln Ala Ala Gln Val
            275                 280                 285

Val Gly Trp Gln Met Val Gly Leu Leu Tyr Phe Gln Gln Tyr Phe Trp
        290                 295                 300

Val His His Trp Leu Val Ala Ile Thr Tyr Leu His His Thr His Glu
305                 310                 315                 320

Glu Val His His Phe Asp Ala Asp Ser Trp Thr Phe Val Lys Gly Ala
                325                 330                 335

Leu Ala Thr Val Asp Arg Asp Phe Gly Phe Ile Gly Lys His Leu Phe
            340                 345                 350

His Asn Ile Ile Asp His His Val Val His Leu Phe Pro Arg Ile
        355                 360                 365

Pro Phe Tyr Tyr Ala Glu Glu Ala Thr Asn Ser Ile Arg Pro Met Leu
    370                 375                 380

Gly Pro Leu Tyr His Arg Asp Asp Arg Ser Phe Met Gly Gln Leu Trp
385                 390                 395                 400

Tyr Asn Phe Thr His Cys Lys Trp Val Val Pro Asp Pro Gln Val Pro
                405                 410                 415

Gly Ala Leu Ile Trp Ala His Thr Val Gln Ser Thr Gln
            420                 425

<210> SEQ ID NO 15
<211> LENGTH: 1446
<212> TYPE: DNA
<213> ORGANISM: Neurospora crassa

<400> SEQUENCE: 15
atggcgtccg tctcctctgc ccttcccgag ggcaacaagc ctgccctgcg caggacccaa      60
accgaggcca cctccgactc ataccctggt accgctgatg cctctccctt cgactctccc     120
cttgagcgct cggcctccaa cacctcgctt tcttcccagg cctctgacaa cgtcaagacc     180
gacaaggccg agttcggcaa gctgctcgac acgtatggca cgagttcga ggtccccgac     240 ttcaccatca aggacatccg cgatgccatc cccgccact gctttgagcg ttcggctctt     300
cacagcttgg cgcacgtcgt ccgcgacatc atttacctca ccgtcacttt ttacgtctgg     360
aacaagtatg tcactcccga gtacatcccc atgaaggctg cccgtgtcgt cctctggggt     420
ctgtacacct tcatgcaggg cctttttcggc accggtctct gggttcttgc catgagtgc     480 ggtcaccagg ctttctcccc gtccaggttg atcaacgaca ccgtcggctg gtcctccac     540 tctgcccttc tcgtccccta cttctcgtgg aagttctccc acagcaagca ccacaaggcc     600
accggcaaca tcgagcgtga catggtcttc gttcctcgga cccgcgagca gtttgcgtct     660
cgcatcggcc gtttcgtcca tgagatttcc gagttgaccg aggagacccc catctacacc     720
ttgatccacc ttatcggtca gcagctcatc ggctggccca actacctcat gaccaacgtc     780
accggccaca acttccacga gaggcagcgc gagggtcgtg gcaagggcaa gaagaacggc     840
```

```
tggttcactg gtgtcaacca cttcaacccc agctctcccc tctatgagga gcgtgaggcc    900
ccctggatca tcgtctccga catcggtatc gctatcgccg ccaccgccct catctacctc    960
ggcaacacct tcggctggtc caacatgttc gtctggtact tccttcccta cctctgggtc   1020
aaccactggc ttgttgccat cacctacctc cagcacaccg accctcgct ccccactac     1080
accectgate agtggaactt tgtccgtggt gccgccgcga ctattgaccg cgagttcggc   1140
ttcatcggcc gtcacctcct ccacggcatt atcgagaccc acgttctcca ccactacgtc   1200
agcaccattc ccttttacca cgccgacgag gcctccgagg ccatcaagaa ggtcatgggc   1260
cgtcactacc gcgctgacgt ccaagatggc cccatcggtt tcatcaaggc catgtggaag   1320
gctgctcgtt ggtgccagtg ggttgagcct accgagggcg ctgagggtaa gggcaagggc   1380
gtcttgttct accgcaacca gaacggtctc ggtgtcaagc ctgccaagct ccccaaaacc   1440
aactaa                                                              1446
```

<210> SEQ ID NO 16
<211> LENGTH: 481
<212> TYPE: PRT
<213> ORGANISM: Neurospora crassa

<400> SEQUENCE: 16

```
Met Ala Ser Val Ser Ser Ala Leu Pro Glu Gly Asn Lys Pro Ala Leu
1               5                   10                  15

Arg Arg Thr Gln Thr Glu Ala Thr Ser Asp Ser Tyr Pro Gly Thr Ala
            20                  25                  30

Asp Ala Ser Pro Phe Asp Ser Pro Leu Glu Arg Ser Ala Ser Asn Thr
        35                  40                  45

Ser Leu Ser Ser Gln Ala Ser Asp Asn Val Lys Thr Asp Lys Ala Glu
    50                  55                  60

Phe Gly Lys Leu Leu Asp Thr Tyr Gly Asn Glu Phe Glu Val Pro Asp
65                  70                  75                  80

Phe Thr Ile Lys Asp Ile Arg Asp Ala Ile Pro Ala His Cys Phe Glu
                85                  90                  95

Arg Ser Ala Leu His Ser Leu Ala His Val Arg Asp Ile Ile Tyr
            100                 105                 110

Leu Thr Val Thr Phe Tyr Val Trp Asn Lys Tyr Val Thr Pro Glu Tyr
        115                 120                 125

Ile Pro Met Lys Ala Ala Arg Val Val Leu Trp Gly Leu Tyr Thr Phe
    130                 135                 140

Met Gln Gly Leu Phe Gly Thr Gly Leu Trp Val Leu Ala His Glu Cys
145                 150                 155                 160

Gly His Gln Ala Phe Ser Pro Ser Arg Leu Ile Asn Asp Thr Val Gly
                165                 170                 175

Trp Val Leu His Ser Ala Leu Leu Val Pro Tyr Phe Ser Trp Lys Phe
            180                 185                 190

Ser His Ser Lys His His Lys Ala Thr Gly Asn Ile Glu Arg Asp Met
        195                 200                 205

Val Phe Val Pro Arg Thr Arg Glu Gln Phe Ala Ser Arg Ile Gly Arg
    210                 215                 220

Phe Val His Glu Ile Ser Glu Leu Thr Glu Thr Pro Ile Tyr Thr
225                 230                 235                 240

Leu Ile His Leu Ile Gly Gln Gln Leu Ile Gly Trp Pro Asn Tyr Leu
                245                 250                 255
```

-continued

```
Met Thr Asn Val Thr Gly His Asn Phe His Glu Arg Gln Arg Glu Gly
            260                 265                 270
Arg Gly Lys Gly Lys Lys Asn Gly Trp Phe Thr Gly Val Asn His Phe
        275                 280                 285
Asn Pro Ser Ser Pro Leu Tyr Glu Glu Arg Glu Ala Pro Trp Ile Ile
    290                 295                 300
Val Ser Asp Ile Gly Ile Ala Ile Ala Ala Thr Ala Leu Ile Tyr Leu
305                 310                 315                 320
Gly Asn Thr Phe Gly Trp Ser Asn Met Phe Val Trp Tyr Phe Leu Pro
                325                 330                 335
Tyr Leu Trp Val Asn His Trp Leu Val Ala Ile Thr Tyr Leu Gln His
            340                 345                 350
Thr Asp Pro Ser Leu Pro His Tyr Thr Pro Asp Gln Trp Asn Phe Val
        355                 360                 365
Arg Gly Ala Ala Ala Thr Ile Asp Arg Glu Phe Gly Phe Ile Gly Arg
    370                 375                 380
His Leu Leu His Gly Ile Ile Glu Thr His Val Leu His His Tyr Val
385                 390                 395                 400
Ser Thr Ile Pro Phe Tyr His Ala Asp Glu Ala Ser Glu Ala Ile Lys
                405                 410                 415
Lys Val Met Gly Arg His Tyr Arg Ala Asp Val Gln Asp Gly Pro Ile
            420                 425                 430
Gly Phe Ile Lys Ala Met Trp Lys Ala Ala Arg Trp Cys Gln Trp Val
        435                 440                 445
Glu Pro Thr Glu Gly Ala Glu Gly Lys Gly Lys Gly Val Leu Phe Tyr
    450                 455                 460
Arg Asn Gln Asn Gly Leu Gly Val Lys Pro Ala Lys Leu Pro Lys Thr
465                 470                 475                 480
Asn

<210> SEQ ID NO 17
<211> LENGTH: 1212
<212> TYPE: DNA
<213> ORGANISM: Fusarium graminearium

<400> SEQUENCE: 17
atggccacca gacagcgaac tgccaccact gttgtggtcg agaaggacct gcccaaggtc      60
actctcgagg ccacttctca gcctcaattc cccgacatca agaccatcaa ggatgccatc     120
cccgcccact gcttccagcc ctcgctcatc acctcatact actatgtcgt ccgcgacttc     180
gccatggtcg gctccctcgt ctgggccgcc ctcacctaca tccccggcat tgaggaccag     240
tacctccgcg tcgccgcctg gatggcctac ggcttcctcc agggtctctt ctgcaccgga     300
atctggattc tcggtcatga gtgcggccac ggtgccttct ctacccacag caagctcaac     360
aatgtgaccg gctggttcct ccactcgttc tcatggtcc cctatttcag ctggaagtac     420
tctcaccacc gtcaccaccg cttcaccggc acatggatc tcgacatggc ctttgtcccc     480
cgcacttcgc ccaagccttc tttgtctttc cgcattgctg gtatgacgt cgctgagctg     540 attgaggaca ccccattgc ccaggccgtc aagctcatct ccaccagct cttcggatgg     600 caggtgtaca ccttcttcaa cgccagctct ggcaagggta gcaagcagtg ggagcccaag     660
agcggcttgg ccagctggtt ccgcgtcagc cacttcgagc ccaccagcgc tgtcttccgc     720
cccgccgagg ctccttttcat cctcatctcc gacattggtc tcgccctcac tggaactgct     780
ctgtactttg cttccaagga ggtcggcgtt tccaccgttc tctacctcta cctcgtcccc     840
```

-continued

```
tacctctggg tccaccactg gctcgtcgcc atcacctacc tccaccacca ccacaccgag    900
cttccccact acaccgccga gggctggacc tacgtcaagg gtgctctcgc tactgttgac    960
cgcgagtttg gcttcattgg caagcacctt ttccacggca tcattgagaa gcacgtcatt   1020
caccacctgt tccctaagat ccccttctac aaggctgacg aggccaccga ggccatcaag   1080
cccatcatcg gcgaccacta ctgccacgac gaccgcagct tccttggcca gctctggacc   1140
atctttggca gcctcaagta cgtcgagcac gaccccgccg tccctggtgc catgcgctgg   1200
gccaaggagt ag                                                       1212

<210> SEQ ID NO 18
<211> LENGTH: 403
<212> TYPE: PRT
<213> ORGANISM: Fusarium graminearium

<400> SEQUENCE: 18

Met Ala Thr Arg Gln Arg Thr Ala Thr Thr Val Val Val Glu Lys Asp
1               5                   10                  15

Leu Pro Lys Val Thr Leu Glu Ala Thr Ser Gln Pro Gln Phe Pro Asp
            20                  25                  30

Ile Lys Thr Ile Lys Asp Ala Ile Pro Ala His Cys Phe Gln Pro Ser
        35                  40                  45

Leu Ile Thr Ser Tyr Tyr Tyr Val Val Arg Asp Phe Ala Met Val Gly
    50                  55                  60

Ser Leu Val Trp Ala Ala Leu Thr Tyr Ile Pro Gly Ile Glu Asp Gln
65                  70                  75                  80

Tyr Leu Arg Val Ala Ala Trp Met Ala Tyr Gly Phe Leu Gln Gly Leu
                85                  90                  95

Phe Cys Thr Gly Ile Trp Ile Leu Gly His Glu Cys Gly His Gly Ala
            100                 105                 110

Phe Ser Thr His Ser Lys Leu Asn Asn Val Thr Gly Trp Phe Leu His
        115                 120                 125

Ser Phe Leu Met Val Pro Tyr Phe Ser Trp Lys Tyr Ser His His Arg
    130                 135                 140

His His Arg Phe Thr Gly His Met Asp Leu Asp Met Ala Phe Val Pro
145                 150                 155                 160

Arg Thr Ser Pro Lys Pro Ser Leu Ser Phe Arg Ile Ala Gly Met Asp
                165                 170                 175

Val Ala Glu Leu Ile Glu Asp Thr Pro Ile Ala Gln Ala Val Lys Leu
            180                 185                 190

Ile Phe His Gln Leu Phe Gly Trp Gln Val Tyr Thr Phe Phe Asn Ala
        195                 200                 205

Ser Ser Gly Lys Gly Ser Lys Gln Trp Glu Pro Lys Ser Gly Leu Ala
    210                 215                 220

Ser Trp Phe Arg Val Ser His Phe Glu Pro Thr Ser Ala Val Phe Arg
225                 230                 235                 240

Pro Ala Glu Ala Pro Phe Ile Leu Ile Ser Asp Ile Gly Leu Ala Leu
                245                 250                 255

Thr Gly Thr Ala Leu Tyr Phe Ala Ser Lys Glu Val Gly Val Ser Thr
            260                 265                 270

Val Leu Tyr Leu Tyr Leu Val Pro Tyr Leu Trp Val His His Trp Leu
        275                 280                 285

Val Ala Ile Thr Tyr Leu His His His His Thr Glu Leu Pro His Tyr
    290                 295                 300
```

Thr Ala Glu Gly Trp Thr Tyr Val Lys Gly Ala Leu Ala Thr Val Asp
305                 310                 315                 320

Arg Glu Phe Gly Phe Ile Gly Lys His Leu Phe His Gly Ile Ile Glu
            325                 330                 335

Lys His Val Ile His His Leu Phe Pro Lys Ile Pro Phe Tyr Lys Ala
                340                 345                 350

Asp Glu Ala Thr Glu Ala Ile Lys Pro Ile Ile Gly Asp His Tyr Cys
            355                 360                 365

His Asp Asp Arg Ser Phe Leu Gly Gln Leu Trp Thr Ile Phe Gly Ser
    370                 375                 380

Leu Lys Tyr Val Glu His Asp Pro Ala Val Pro Gly Ala Met Arg Trp
385                 390                 395                 400

Ala Lys Glu

<210> SEQ ID NO 19
<211> LENGTH: 1371
<212> TYPE: DNA
<213> ORGANISM: Fusarium graminearium

<400> SEQUENCE: 19
tcaaccacgg cgacggatac tgagtctgct gccgtttctc cttcagactc tccccgccat 60
tcggcctctt ccacctcgct ctcgtctctt tccgagattg atatcgccaa gcccaaggcc 120
gaatatggtg ttatgcttga cacctatggc aacaagttcg aggttcccga cttcaccatc 180
aaggagatct acaatgccat ccccaagcac tgcttccagc gctccgctct caagggatac 240
ggatacatcc tccgcgacat tgtccttctt gctaccacct ttagcatctg gtacaactat 300
gtgacccccg agtacatccc tagcactccc gcccgcgctg gtctctgggc tgtctacact 360
gttctccagg gtcttttcgg taccggtctc tgggtcatcg ctcacgagtg tggccacggt 420
gctttctccg actctcgcct tatcaacgac atcaccggct gggtcctcca ctcttctctc 480
ctcgtcccct acttcagctg gcaaatctcc caccgaaagc accacaaggc taccggaaac 540
atggagcgtg acatggtctt tgttccccga actcgcgagc agcaggctac tcgtctcggc 600
aagatgaccc acgagcttgc tcacctcact gaggagaccc ccgtcttcac tctgatcatg 660
cttgttctcc agcagctcgt cggctggccc aactacctca tgaccaacgt tactggccac 720
aactaccacg agcgtcagaa ggagggccgt ggcaagggca agcacaacgg tctcggcggc 780
ggtgtcaacc actttgatcc ccgcagccct ctttacgagc acagcgatgc taagctcatt 840
gtcttgagtg atattggtat cggtctgatg ggtaccgctc tgtacttcct cgtccagaag 900
tttggctttt acaacatggc catctggtac tttgtccctt acctttgggt caaccactgg 960
ctcgtcgcca ttactttcct ccagcacacc gaccctaccc ttccccacta caccaacgac 1020
gagtggaact ttgtccgcgg tgctgctgct accatcgatc gtgagatggg tttcattggc 1080
cgacacctcc tccacggtat catcgagact cacgtcctcc accactacgt cagcagcatc 1140
cccttctaca acgccgacga ggctaccgag gctatcaagc ctgtcatggg caagcactac 1200
cgtgccgacg tccaggatgg tccccgtggt ttcattcgtg ccatgtaccg cagtgcccgt 1260
atgtgccagt gggttgagcc cagcgctgag gccgagggtg ctggcaaggg tgttctgttc 1320
ttccgcaacc gcaacaaggt tggcactgct cctgccgtcc tcaaggctta g 1371

<210> SEQ ID NO 20
<211> LENGTH: 456
<212> TYPE: PRT

-continued

<213> ORGANISM: Fusarium graminearium

<400> SEQUENCE: 20

```
Ser Thr Thr Ala Thr Asp Thr Glu Ser Ala Ala Val Ser Pro Ser Asp
1               5                   10                  15

Ser Pro Arg His Ser Ala Ser Ser Thr Ser Leu Ser Ser Leu Ser Glu
            20                  25                  30

Ile Asp Ile Ala Lys Pro Lys Ala Glu Tyr Gly Val Met Leu Asp Thr
        35                  40                  45

Tyr Gly Asn Lys Phe Glu Val Pro Asp Phe Thr Ile Lys Glu Ile Tyr
    50                  55                  60

Asn Ala Ile Pro Lys His Cys Phe Gln Arg Ser Ala Leu Lys Gly Tyr
65                  70                  75                  80

Gly Tyr Ile Leu Arg Asp Ile Val Leu Leu Ala Thr Thr Phe Ser Ile
                85                  90                  95

Trp Tyr Asn Tyr Val Thr Pro Glu Tyr Ile Pro Ser Thr Pro Ala Arg
            100                 105                 110

Ala Gly Leu Trp Ala Val Tyr Thr Val Leu Gln Gly Leu Phe Gly Thr
        115                 120                 125

Gly Leu Trp Val Ile Ala His Glu Cys Gly His Gly Ala Phe Ser Asp
    130                 135                 140

Ser Arg Leu Ile Asn Asp Ile Thr Gly Trp Val Leu His Ser Ser Leu
145                 150                 155                 160

Leu Val Pro Tyr Phe Ser Trp Gln Ile Ser His Arg Lys His His Lys
                165                 170                 175

Ala Thr Gly Asn Met Glu Arg Asp Met Val Phe Val Pro Arg Thr Arg
            180                 185                 190

Glu Gln Gln Ala Thr Arg Leu Gly Lys Met Thr His Glu Leu Ala His
        195                 200                 205

Leu Thr Glu Glu Thr Pro Val Phe Thr Leu Ile Met Leu Val Leu Gln
    210                 215                 220

Gln Leu Val Gly Trp Pro Asn Tyr Leu Met Thr Asn Val Thr Gly His
225                 230                 235                 240

Asn Tyr His Glu Arg Gln Lys Glu Gly Arg Gly Lys Gly Lys His Asn
                245                 250                 255

Gly Leu Gly Gly Gly Val Asn His Phe Asp Pro Arg Ser Pro Leu Tyr
            260                 265                 270

Glu His Ser Asp Ala Lys Leu Ile Val Leu Ser Asp Ile Gly Ile Gly
        275                 280                 285

Leu Met Gly Thr Ala Leu Tyr Phe Leu Val Gln Lys Phe Gly Phe Tyr
    290                 295                 300

Asn Met Ala Ile Trp Tyr Phe Val Pro Tyr Leu Trp Val Asn His Trp
305                 310                 315                 320

Leu Val Ala Ile Thr Phe Leu Gln His Thr Asp Pro Thr Leu Pro His
                325                 330                 335

Tyr Thr Asn Asp Glu Trp Asn Phe Val Arg Gly Ala Ala Ala Thr Ile
            340                 345                 350

Asp Arg Glu Met Gly Phe Ile Gly Arg His Leu Leu His Gly Ile Ile
        355                 360                 365

Glu Thr His Val Leu His His Tyr Val Ser Ser Ile Pro Phe Tyr Asn
    370                 375                 380

Ala Asp Glu Ala Thr Glu Ala Ile Lys Pro Val Met Gly Lys His Tyr
385                 390                 395                 400
```

```
Arg Ala Asp Val Gln Asp Gly Pro Arg Gly Phe Ile Arg Ala Met Tyr
                405                 410                 415

Arg Ser Ala Arg Met Cys Gln Trp Val Glu Pro Ser Ala Glu Ala Glu
            420                 425                 430

Gly Ala Gly Lys Gly Val Leu Phe Phe Arg Asn Arg Asn Lys Val Gly
        435                 440                 445

Thr Ala Pro Ala Val Leu Lys Ala
    450                 455

<210> SEQ ID NO 21
<211> LENGTH: 424
<212> TYPE: PRT
<213> ORGANISM: Aspergillus fumigatus

<400> SEQUENCE: 21

Met Ala Ser Asp Ala Glu Lys Thr Ser Ser Lys Met Ile Asp Thr Tyr
  1               5                  10                  15

Gly Asn Glu Phe Lys Ile Pro Asp Tyr Thr Ile Lys Gln Ile Arg Asp
                 20                  25                  30

Ala Ile Pro Ala His Cys Tyr Gln Arg Ser Ala Ala Thr Ser Leu Tyr
             35                  40                  45

Tyr Val Phe Arg Asp Met Ala Ile Leu Ala Ser Val Phe Tyr Val Phe
         50                  55                  60

His Asn Tyr Val Thr Pro Glu Thr Val Pro Ser Met Pro Val Arg Val
 65                  70                  75                  80

Val Leu Trp Thr Ile Tyr Thr Val Gln Gly Leu Val Gly Thr Gly Val
                 85                  90                  95

Val Trp Val Leu Ala His Glu Cys Gly His Gln Ala Phe Ser Thr Ser
            100                 105                 110

Lys Val Leu Asn Asp Thr Val Gly Trp Ile Cys His Ser Leu Leu Leu
        115                 120                 125

Val Pro Tyr Phe Ser Trp Lys Ile Ser His Gly Lys His His Lys Ala
    130                 135                 140

Thr Gly Asn Ile Ala Arg Asp Met Val Phe Val Pro Lys Thr Arg Glu
145                 150                 155                 160

Glu Tyr Ala Thr Arg Ile Gly Arg Ala Ala His Glu Leu Ser Glu Leu
                165                 170                 175

Met Glu Glu Thr Pro Ile Leu Thr Ala Thr Asn Leu Val Leu Gln Gln
            180                 185                 190

Leu Phe Gly Trp Pro Met Tyr Leu Leu Thr Asn Val Thr Gly His Asn
        195                 200                 205

Asn His Glu Arg Gln Pro Glu Gly Arg Gly Lys Gly Lys Arg Asn Gly
    210                 215                 220

Tyr Phe Gly Gly Val Asn His Phe Asn Pro Ser Ser Pro Leu Tyr Glu
225                 230                 235                 240

Ala Lys Asp Ala Lys Leu Ile Val Leu Ser Asp Leu Gly Leu Phe Leu
                245                 250                 255

Val Gly Ser Leu Leu Tyr Tyr Ile Gly Ser Thr Tyr Gly Trp Leu Asn
            260                 265                 270

Leu Leu Val Trp Tyr Gly Ile Pro Tyr Leu Trp Val Asn His Trp Leu
        275                 280                 285

Val Ala Ile Thr Phe Leu Gln His Thr Asp Pro Thr Leu Pro His Tyr
    290                 295                 300

Gln Pro Glu Ala Trp Asp Phe Thr Arg Gly Ala Ala Ala Thr Ile Asp
305                 310                 315                 320
```

```
Arg Asp Phe Gly Phe Val Gly Arg His Ile Phe His Gly Ile Ile Glu
                325                 330                 335

Thr His Val Leu His His Tyr Val Ser Thr Ile Pro Phe Tyr His Ala
            340                 345                 350

Asp Glu Ala Ser Glu Ala Ile Gln Lys Val Met Gly Pro His Tyr Arg
        355                 360                 365

Ser Glu Ala His Thr Gly Trp Thr Gly Phe Leu Lys Ala Leu Trp Thr
    370                 375                 380

Ser Ala Arg Thr Cys Gln Trp Val Glu Pro Thr Glu Gly Ala Lys Gly
385                 390                 395                 400

Glu Ser Gln Tyr Val Leu Phe Tyr Arg Asn Ile Asn Gly Ile Gly Val
            405                 410                 415

Pro Pro Ala Lys Ile Pro Ala Lys
            420
```

<210> SEQ ID NO 22
<211> LENGTH: 466
<212> TYPE: PRT
<213> ORGANISM: Aspergillus flavus

<400> SEQUENCE: 22

```
Met Ser Ser Thr Ala Ile Pro Lys Arg Met Ala Leu Asn Arg Asn Pro
1               5                   10                  15

Gly Thr Asp Ser Ser Val Pro Ser Val Ser Val Ser Pro Phe Asp Ser
            20                  25                  30

Pro Arg His Ser Pro Ser Ser Thr Ser Leu Ser Ser Leu Ala Ser Glu
        35                  40                  45

Ser Glu Asn Lys Gly Lys Met Leu Asp Thr Tyr Gly Asn Glu Phe Lys
    50                  55                  60

Ile Pro Asp Tyr Thr Ile Lys Gln Ile Arg Asp Ala Ile Pro Ala His
65                  70                  75                  80

Cys Tyr Glu Arg Lys Ala Leu Thr Ser Leu Tyr Tyr Val Phe Arg Asp
                85                  90                  95

Ile Ala Met Leu Gly Ser Ile Phe Tyr Val Phe His Asn Tyr Val Thr
            100                 105                 110

Pro Glu Thr Val Pro Ser Phe Pro Ala Arg Val Ala Leu Trp Ser Leu
        115                 120                 125

Tyr Thr Val Val Gln Gly Leu Ile Ala Thr Gly Val Trp Val Leu Ala
    130                 135                 140

His Glu Cys Gly His Gln Ala Phe Ser Pro Ser Lys Val Leu Asn Asp
145                 150                 155                 160

Thr Val Gly Trp Ile Cys His Ser Ala Leu Leu Val Pro Tyr Phe Ser
                165                 170                 175

Trp Lys Ile Ser His Gly Lys His His Lys Ala Thr Gly Asn Ile Ala
            180                 185                 190

Arg Asp Met Val Phe Val Pro Lys Thr Arg Glu Glu Tyr Ala Ser Arg
        195                 200                 205

Ile Gly Lys Thr Ile His Asp Leu Asn Glu Leu Met Glu Glu Thr Pro
    210                 215                 220

Ile Ala Thr Val Thr Asn Leu Ile Leu Gln Gln Leu Phe Gly Trp Pro
225                 230                 235                 240

Met Tyr Leu Leu Thr Asn Val Thr Gly His Asn Asn His Glu Arg Gln
                245                 250                 255

Pro Glu Gly Arg Gly Lys Gly Lys Arg Asn Gly Tyr Phe Gly Gly Val
```

```
                    260                 265                 270
Asn His Phe Asn Pro Ser Ser Pro Leu Tyr Glu Ala Lys Asp Ala Lys
                275                 280                 285
Leu Ile Val Leu Ser Asp Leu Gly Leu Ala Ile Thr Gly Ser Val Leu
                290                 295                 300
Tyr Tyr Ile Gly Ser Thr Gly Trp Leu Asn Leu Leu Val Trp Tyr
305                 310                 315                 320
Gly Ile Pro Tyr Leu Trp Val Asn His Trp Leu Val Ala Ile Thr Tyr
                325                 330                 335
Leu Gln His Thr Asp Pro Thr Leu Pro His Tyr Gln Pro Glu Val Trp
                340                 345                 350
Asn Phe Ala Arg Gly Ala Ala Ala Thr Ile Asp Arg Asp Phe Gly Phe
                355                 360                 365
Val Gly Arg His Ile Leu His Gly Ile Ile Glu Thr His Val Leu His
                370                 375                 380
His Tyr Val Ser Thr Ile Pro Phe Tyr His Ala Asp Glu Ala Ser Glu
385                 390                 395                 400
Ala Ile Gln Lys Val Met Gly Ser His Tyr Arg Thr Glu Ala His Thr
                405                 410                 415
Gly Trp Thr Gly Phe Phe Lys Ala Leu Phe Thr Ser Ala Arg Val Cys
                420                 425                 430
His Trp Val Glu Pro Thr Glu Gly Ala Arg Gly Glu Ser Glu Gly Val
                435                 440                 445
Leu Phe Tyr Arg Asn Thr Asn Gly Ile Gly Val Pro Pro Ala Lys Leu
                450                 455                 460
Ser Lys
465

<210> SEQ ID NO 23
<211> LENGTH: 19
<212> TYPE: DNA
<213> ORGANISM: Artificial Sequence
<220> FEATURE:
<223> OTHER INFORMATION: Primer TEF5'

<400> SEQUENCE: 23
agagaccggg ttggcggcg                                                  19

<210> SEQ ID NO 24
<211> LENGTH: 30
<212> TYPE: DNA
<213> ORGANISM: Artificial Sequence
<220> FEATURE:
<223> OTHER INFORMATION: Primer TEF3'

<400> SEQUENCE: 24
ttggatcctt tgaatgattc ttatactcag                                      30

<210> SEQ ID NO 25
<211> LENGTH: 29
<212> TYPE: DNA
<213> ORGANISM: Artificial Sequence
<220> FEATURE:
<223> OTHER INFORMATION: Primer XPR5'

<400> SEQUENCE: 25
tttccgcggc ccgagattcc ggcctcttc                                       29

<210> SEQ ID NO 26
```

```
<211> LENGTH: 31
<212> TYPE: DNA
<213> ORGANISM: Artificial Sequence
<220> FEATURE:
<223> OTHER INFORMATION: Primer XPR3'

<400> SEQUENCE: 26
tttccgcgga cacaatatct ggtcaaattt c                              31

<210> SEQ ID NO 27
<211> LENGTH: 39
<212> TYPE: DNA
<213> ORGANISM: Artificial Sequence
<220> FEATURE:
<223> OTHER INFORMATION: Primer YL5

<400> SEQUENCE: 27
cccccctcga ggtcgatggt gtcgataagc ttgatatcg                      39

<210> SEQ ID NO 28
<211> LENGTH: 39
<212> TYPE: DNA
<213> ORGANISM: Artificial Sequence
<220> FEATURE:
<223> OTHER INFORMATION: Primer YL6

<400> SEQUENCE: 28
cgatatcaag cttatcgaca ccatcgacct cgaggggggg                     39

<210> SEQ ID NO 29
<211> LENGTH: 35
<212> TYPE: DNA
<213> ORGANISM: Artificial Sequence
<220> FEATURE:
<223> OTHER INFORMATION: Primer YL9

<400> SEQUENCE: 29
tggtaaataa atgatgtcga ctcaggcgac gacgg                          35

<210> SEQ ID NO 30
<211> LENGTH: 35
<212> TYPE: DNA
<213> ORGANISM: Artificial Sequence
<220> FEATURE:
<223> OTHER INFORMATION: Primer YL10

<400> SEQUENCE: 30
ccgtcgtcgc ctgagtcgac atcatttatt tacca                          35

<210> SEQ ID NO 31
<211> LENGTH: 37
<212> TYPE: DNA
<213> ORGANISM: Artificial Sequence
<220> FEATURE:
<223> OTHER INFORMATION: Primer YL7

<400> SEQUENCE: 31
caaccgattt cgacagttaa ttaataattt gaatcga                        37

<210> SEQ ID NO 32
<211> LENGTH: 37
<212> TYPE: DNA
<213> ORGANISM: Artificial Sequence
<220> FEATURE:
<223> OTHER INFORMATION: Primer YL8

<400> SEQUENCE: 32
```

```
tcgattcaaa ttattaatta actgtcgaaa tcggttg                                    37

<210> SEQ ID NO 33
<211> LENGTH: 36
<212> TYPE: DNA
<213> ORGANISM: Artificial Sequence
<220> FEATURE:
<223> OTHER INFORMATION: Primer YL3

<400> SEQUENCE: 33
gtataagaat cattcaccat ggatccacta gttcta                                     36

<210> SEQ ID NO 34
<211> LENGTH: 36
<212> TYPE: DNA
<213> ORGANISM: Artificial Sequence
<220> FEATURE:
<223> OTHER INFORMATION: Primer YL4

<400> SEQUENCE: 34
tagaactagt ggatccatgg tgaatgattc ttatac                                     36

<210> SEQ ID NO 35
<211> LENGTH: 30
<212> TYPE: DNA
<213> ORGANISM: Artificial Sequence
<220> FEATURE:
<223> OTHER INFORMATION: Primer YL1

<400> SEQUENCE: 35
cagtgccaaa agccaaggca ctgagctcgt                                            30

<210> SEQ ID NO 36
<211> LENGTH: 31
<212> TYPE: DNA
<213> ORGANISM: Artificial Sequence
<220> FEATURE:
<223> OTHER INFORMATION: Primer YL2

<400> SEQUENCE: 36
gacgagctca gtgccttggc ttttggcact g                                          31

<210> SEQ ID NO 37
<211> LENGTH: 33
<212> TYPE: DNA
<213> ORGANISM: Artificial Sequence
<220> FEATURE:
<223> OTHER INFORMATION: Primer YL61

<400> SEQUENCE: 37
acaattccac acaacgtacg agccggaagc ata                                        33

<210> SEQ ID NO 38
<211> LENGTH: 33
<212> TYPE: DNA
<213> ORGANISM: Artificial Sequence
<220> FEATURE:
<223> OTHER INFORMATION: Primer YL62

<400> SEQUENCE: 38
tatgcttccg gctcgtacgt tgtgtggaat tgt                                        33

<210> SEQ ID NO 39
<211> LENGTH: 26
<212> TYPE: DNA
```

```
<213> ORGANISM: Artificial Sequence
<220> FEATURE:
<223> OTHER INFORMATION: Degenerate primer P73
<220> FEATURE:
<221> NAME/KEY: misc_feature
<222> LOCATION: (24)..(24)
<223> OTHER INFORMATION: n is a, c, g, or t

<400> SEQUENCE: 39
tgggtcctgg gccaygartg yggnca                                            26

<210> SEQ ID NO 40
<211> LENGTH: 9
<212> TYPE: PRT
<213> ORGANISM: Artificial Sequence
<220> FEATURE:
<223> OTHER INFORMATION: Consensus sequence in delta12 desaturases

<400> SEQUENCE: 40

Trp Val Leu Gly His Glu Cys Gly His
1               5

<210> SEQ ID NO 41
<211> LENGTH: 30
<212> TYPE: DNA
<213> ORGANISM: Artificial Sequence
<220> FEATURE:
<223> OTHER INFORMATION: Degenerate primer P76
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 41
ggtggcctcc tcggcgtgrt araanggnat                                        30

<210> SEQ ID NO 42
<211> LENGTH: 10
<212> TYPE: PRT
<213> ORGANISM: Artificial Sequence
<220> FEATURE:
<223> OTHER INFORMATION: Consensus sequence in delta12 desaturases
<220> FEATURE:
<221> NAME/KEY: MISC_FEATURE
<222> LOCATION: (1)..(1)
<223> OTHER INFORMATION: Xaa = Met or Ile

<400> SEQUENCE: 42

Xaa Pro Phe Val His Ala Glu Glu Ala Thr
1               5                   10

<210> SEQ ID NO 43
<211> LENGTH: 29
<212> TYPE: DNA
<213> ORGANISM: Artificial Sequence
<220> FEATURE:
<223> OTHER INFORMATION: Primer P99

<400> SEQUENCE: 43
ggcaagctta acgccccgct gtttgagaa                                         29

<210> SEQ ID NO 44
<211> LENGTH: 36
<212> TYPE: DNA
<213> ORGANISM: Artificial Sequence
```

```
<220> FEATURE:
<223> OTHER INFORMATION: Primer P100

<400> SEQUENCE: 44
tgacgttgtt agatctacgt gggtctcgat gatgtc                              36

<210> SEQ ID NO 45
<211> LENGTH: 35
<212> TYPE: DNA
<213> ORGANISM: Artificial Sequence
<220> FEATURE:
<223> OTHER INFORMATION: Primer P101

<400> SEQUENCE: 45
gacccacgta gatctaacaa cgtcaccgga tgggt                               35

<210> SEQ ID NO 46
<211> LENGTH: 29
<212> TYPE: DNA
<213> ORGANISM: Artificial Sequence
<220> FEATURE:
<223> OTHER INFORMATION: Primer P102

<400> SEQUENCE: 46
cgggaattcg gggttgaagt ggttgacag                                      29

<210> SEQ ID NO 47
<211> LENGTH: 16
<212> TYPE: DNA
<213> ORGANISM: Artificial Sequence
<220> FEATURE:
<223> OTHER INFORMATION: Primer P119

<400> SEQUENCE: 47
taataacgcc agggtt                                                    16

<210> SEQ ID NO 48
<211> LENGTH: 22
<212> TYPE: DNA
<213> ORGANISM: Artificial Sequence
<220> FEATURE:
<223> OTHER INFORMATION: Primer P120

<400> SEQUENCE: 48
gtagaagggc attcgagaca cg                                             22

<210> SEQ ID NO 49
<211> LENGTH: 22
<212> TYPE: DNA
<213> ORGANISM: Artificial Sequence
<220> FEATURE:
<223> OTHER INFORMATION: Primer P121

<400> SEQUENCE: 49
tgtgcccaag gaccgaaagg ag                                             22

<210> SEQ ID NO 50
<211> LENGTH: 28
<212> TYPE: DNA
<213> ORGANISM: Artificial Sequence
<220> FEATURE:
<223> OTHER INFORMATION: Primer P122

<400> SEQUENCE: 50
tgcaggtagg tgatggccac gagttggg                                       28
```

<210> SEQ ID NO 51
<211> LENGTH: 1936
<212> TYPE: DNA
<213> ORGANISM: Yarrowia lioplytica

<400> SEQUENCE: 51

| | | | | | |
|---|---|---|---|---|---|
| cgtagttata | tacaagaggt | agatgcgtgc | tggtgttaga | ggggctctca | ggattaggag | 60 |
| gaaaatttga | cattggccct | caacatataa | cctcgggtgt | gcctctgttt | accctcagct | 120 |
| tttgcttgtc | cccaagtcag | tcacgccagg | ccaaaaaggt | tggtggattg | acagggagaa | 180 |
| aaaaaaaagc | ctagtgggtt | taaactcgag | gtaagacatt | gaaatatata | ccggtcggca | 240 |
| tcctgagtcc | ctttctcgta | ttccaacaga | ccgaccatag | aaatggattc | gaccacgcag | 300 |
| accaacaccg | gcaccggcaa | ggtggccgtg | cagcccccca | cggccttcat | taagcccatt | 360 |
| gagaaggtgt | ccgagcccgt | ctacgacacc | tttggcaacg | agttcactcc | tccagactac | 420 |
| tctatcaagg | atattctgga | tgccattccc | caggagtgct | acaagcggtc | ctacgttaag | 480 |
| tcctactcgt | acgtggcccg | agactgcttc | tttatcgccg | ttttgccta | catggcctac | 540 |
| gcgtacctgc | ctcttattcc | ctcggcttcc | ggccgagctg | tggcctgggc | catgtactcc | 600 |
| attgtccagg | gtctgtttgg | caccggtctg | tgggttcttg | cccacgagtg | tggccactct | 660 |
| gctttctccg | actctaacac | cgtcaacaac | gtcaccggat | gggttctgca | ctcctccatg | 720 |
| ctggtcccctt | actacgcctg | gaagctgacc | cactccatgc | accacaagtc | cactggtcac | 780 |
| ctcacccgtg | atatggtgtt | tgtgcccaag | gaccgaaagg | agtttatgga | gaaccgaggc | 840 |
| gcccatgact | ggtctgagct | tgctgaggac | gctcccctca | tgaccctcta | cggcctcatc | 900 |
| acccagcagg | tgtttggatg | gcctctgtat | ctgctgtctt | acgttaccgg | acagaagtac | 960 |
| cccaagctca | acaaatgggc | tgtcaaccac | ttcaacccca | cgccccgct | gtttgagaag | 1020 |
| aaggactggt | tcaacatctg | gatctctaac | gtcggtattg | gtatcaccat | gtccgtcatc | 1080 |
| gcatactcca | tcaaccgatg | gggcctggct | tccgtcaccc | tctactacct | gatcccctac | 1140 |
| ctgtgggtca | accactggct | cgtggccatc | acctacctgc | agcacaccga | ccccactctg | 1200 |
| ccccactacc | acgccgacca | gtggaacttc | acccgaggag | ccgccgccac | catcgaccga | 1260 |
| gagtttggct | tcatcggctc | cttctgcttc | catgacatca | tcgagaccca | cgttctgcac | 1320 |
| cactacgtgt | ctcgaattcc | cttctacaac | gcccgaatcg | ccactgagaa | gatcaagaag | 1380 |
| gtcatgggca | agcactaccg | acacgacgac | accaacttca | tcaagtctct | ttacactgtc | 1440 |
| gcccgaacct | gccagtttgt | tgaaggtaag | gaaggcattc | agatgtttag | aaacgtcaat | 1500 |
| ggagtcggag | ttgctcctga | cggcctgcct | tctaaaaagt | agagctagaa | atgttatttg | 1560 |
| attgtgtttt | aactgaacag | caccgagccc | gaggctaagc | caagcgaagc | cgagggggttg | 1620 |
| tgtagtccat | ggacgtaacg | agtaggcgat | atcaccgcac | tcggcactgc | gtgtctgcgt | 1680 |
| tcatgggcga | agtcacatta | cgctgacaac | cgttgtagtt | tcccttttagt | atcaatactg | 1740 |
| ttacaagtac | cggtctcgta | ctcgtactga | tacgaatctg | tgggaagaag | tcacccttat | 1800 |
| cagaccttca | tactgatgtt | tcggatatca | atagaactgg | catagagccg | ttaaagaagt | 1860 |
| ttcacttaat | cactccaacc | ctcctacttg | tagattcaag | cagatcgata | agatggattt | 1920 |
| gatggtcagt | gctagc | | | | | 1936 |

<210> SEQ ID NO 52
<211> LENGTH: 419
<212> TYPE: PRT
<213> ORGANISM: Yarrowia lipolytica

<400> SEQUENCE: 52

```
Met Asp Ser Thr Thr Gln Thr Asn Thr Gly Thr Gly Lys Val Ala Val
1               5                   10                  15

Gln Pro Pro Thr Ala Phe Ile Lys Pro Ile Glu Lys Val Ser Glu Pro
            20                  25                  30

Val Tyr Asp Thr Phe Gly Asn Glu Phe Thr Pro Pro Asp Tyr Ser Ile
        35                  40                  45

Lys Asp Ile Leu Asp Ala Ile Pro Gln Glu Cys Tyr Lys Arg Ser Tyr
    50                  55                  60

Val Lys Ser Tyr Ser Tyr Val Ala Arg Asp Cys Phe Phe Ile Ala Val
65                  70                  75                  80

Phe Ala Tyr Met Ala Tyr Ala Tyr Leu Pro Leu Ile Pro Ser Ala Ser
                85                  90                  95

Gly Arg Ala Val Ala Trp Ala Met Tyr Ser Ile Val Gln Gly Leu Phe
            100                 105                 110

Gly Thr Gly Leu Trp Val Leu Ala His Glu Cys Gly His Ser Ala Phe
        115                 120                 125

Ser Asp Ser Asn Thr Val Asn Asn Val Thr Gly Trp Val Leu His Ser
    130                 135                 140

Ser Met Leu Val Pro Tyr Tyr Ala Trp Lys Leu Thr His Ser Met His
145                 150                 155                 160

His Lys Ser Thr Gly His Leu Thr Arg Asp Met Val Phe Val Pro Lys
                165                 170                 175

Asp Arg Lys Glu Phe Met Glu Asn Arg Gly Ala His Asp Trp Ser Glu
            180                 185                 190

Leu Ala Glu Asp Ala Pro Leu Met Thr Leu Tyr Gly Leu Ile Thr Gln
        195                 200                 205

Gln Val Phe Gly Trp Pro Leu Tyr Leu Leu Ser Tyr Val Thr Gly Gln
    210                 215                 220

Lys Tyr Pro Lys Leu Asn Lys Trp Ala Val Asn His Phe Asn Pro Asn
225                 230                 235                 240

Ala Pro Leu Phe Glu Lys Lys Asp Trp Phe Asn Ile Trp Ile Ser Asn
                245                 250                 255

Val Gly Ile Gly Ile Thr Met Ser Val Ile Ala Tyr Ser Ile Asn Arg
            260                 265                 270

Trp Gly Leu Ala Ser Val Thr Leu Tyr Tyr Leu Ile Pro Tyr Leu Trp
        275                 280                 285

Val Asn His Trp Leu Val Ala Ile Thr Tyr Leu Gln His Thr Asp Pro
    290                 295                 300

Thr Leu Pro His Tyr His Ala Asp Gln Trp Asn Phe Thr Arg Gly Ala
305                 310                 315                 320

Ala Ala Thr Ile Asp Arg Glu Phe Gly Phe Ile Gly Ser Phe Cys Phe
                325                 330                 335

His Asp Ile Ile Glu Thr His Val Leu His His Tyr Val Ser Arg Ile
            340                 345                 350

Pro Phe Tyr Asn Ala Arg Ile Ala Thr Glu Lys Ile Lys Lys Val Met
        355                 360                 365

Gly Lys His Tyr Arg His Asp Asp Thr Asn Phe Ile Lys Ser Leu Tyr
    370                 375                 380

Thr Val Ala Arg Thr Cys Gln Phe Val Glu Gly Lys Glu Gly Ile Gln
385                 390                 395                 400

Met Phe Arg Asn Val Asn Gly Val Gly Val Ala Pro Asp Gly Leu Pro
```

<210> SEQ ID NO 53
<211> LENGTH: 25
<212> TYPE: DNA
<213> ORGANISM: Artificial Sequence
<220> FEATURE:
<223> OTHER INFORMATION: Primer P147

<400> SEQUENCE: 53
tcatgccatg gattcgacca cgcag                                   25

<210> SEQ ID NO 54
<211> LENGTH: 26
<212> TYPE: DNA
<213> ORGANISM: Artificial Sequence
<220> FEATURE:
<223> OTHER INFORMATION: Primer P148

<400> SEQUENCE: 54
acatgcggcc gcctactttt tagaag                                  26

<210> SEQ ID NO 55
<211> LENGTH: 37
<212> TYPE: DNA
<213> ORGANISM: Artificial Sequence
<220> FEATURE:
<223> OTHER INFORMATION: Primer P194

<400> SEQUENCE: 55
agactccatg gcgtccactt cggctctgcc caagcag                      37

<210> SEQ ID NO 56
<211> LENGTH: 44
<212> TYPE: DNA
<213> ORGANISM: Artificial Sequence
<220> FEATURE:
<223> OTHER INFORMATION: Primer P195

<400> SEQUENCE: 56
tttatagcgg ccgcctactt aagcaacggg cttgataaca gcgg              44

<210> SEQ ID NO 57
<211> LENGTH: 12649
<212> TYPE: DNA
<213> ORGANISM: Artificial Sequence
<220> FEATURE:
<223> OTHER INFORMATION: Plasmid pKUNF12T6E
<220> FEATURE:
<221> NAME/KEY: misc_feature
<222> LOCATION: (2507)..(2507)
<223> OTHER INFORMATION: n is a, c, g, or t
<220> FEATURE:
<221> NAME/KEY: misc_feature
<222> LOCATION: (2512)..(2515)
<223> OTHER INFORMATION: n is a, c, g, or t

<400> SEQUENCE: 57
taaccctcac taaagggaac aaaagctgga gctccaccgc ggacacaata tctggtcaaa    60
tttcagtttc gttacataaa tcgttatgtc aaaggagtgt gggaggttaa gagaattatc   120
accggcaaac tatctgttaa ttgctaggta cctctagacg tccacccggg tcgcttggcg   180
gccgaagagg ccggaatctc gggccgcggt ggcggccgct tagttggtct tggacttctt   240
gggcttcttc aggtaggact ggacaaagaa gttgccgaac agagcgagca gggtgatcat   300

```
gtacacgccg agcagctgga ccagagcctg agggtagtcg caggggaaga ggtagtcgta    360
cagggactgc accagcatag ccatgaactg ggtcatctgc agagtggtga tgtagggctt    420
gatgggcttg acgaagccga agccctgaga ggaaaagaag tagtaggcgt acatgacggt    480
gtggacgaag gagttgagga tgacggagaa gtaggcgtcg ccaccaggag cgtacttggc    540
aatagcccac cagatggcga agatggtggc atggtggtac acgtgcagga aggagacctg    600
gttgaacttc ttgcacagga tcatgatagc ggtgtccagg aactcgtagg ccttggagac    660
gtagaacacg tagacgattc gggacatgcc ctgagcgtgg gactcgttgc ccttctccat    720
gtcgttgccg aagaccttgt agccacccag gatagcctgt cggatggtct cgacgcacat    780
gtagagggac agtccgaaga ggaacaggtt gtggagcagc ttgatggtct tcagctcgaa    840
gggcttctcc atctgcttca tgatgggaat gccgaagagc agcatggcca tgtagccgac    900
ctcgaaggcg agcatggtgg agacgtccat catgggcaga ccgtcggtca gagcgtaggg    960
cttagctccg tccatccact ggtcgacacc ggtctcgact cgtccgacca cgtcgtccca   1020
gacagaggag ttggccatgg tgaatgattc ttatactcag aaggaaatgc ttaacgattt   1080
cgggtgtgag ttgacaagga gagagagaaa agaagaggaa aggtaattcg gggacggtgg   1140
tcttttatac ccttggctaa agtcccaacc acaaagcaaa aaaattttca gtagtctatt   1200
ttgcgtccgg catgggttac ccggatggcc agacaaagaa actagtacaa agtctgaaca   1260
agcgtagatt ccagactgca gtaccctacg cccttaacgg caagtgtggg aaccggggga   1320
ggtttgatat gtggggtgaa gggggctctc gccggggttg ggcccgctac tgggtcaatt   1380
tggggtcaat tggggcaatt ggggctgttt tttgggacac aaatacgccg ccaacccggt   1440
ctctcctgaa ttctgcatcg atcgaggaag aggacaagcg gctgcttctt aagtttgtga   1500
catcagtatc caaggcacca ttgcaaggat tcaaggcttt gaacccgtca tttgccattc   1560
gtaacgctgg tagacaggtt gatcggttcc ctacggcctc cacctgtgtc aatcttctca   1620
agctgcctga ctatcaggac attgatcaac ttcggaagaa acttttgtat gccattcgat   1680
cacatgctgt tttcgatttg tcttagagga acgcatatac agtaatcata gagaataaac   1740
gatattcatt tattaaagta gatagttgag gtagaagttg taaagagtga taaatagcgg   1800
ccgcgcctac ttaagcaacg ggcttgataa cagcgggggg ggtgcccacg ttgttgcggt   1860
tgcggaagaa cagaacaccc ttaccagcac cctcggcacc agcgctgggc tcaacccact   1920
ggcacatacg cgcactgcgg tacatggcgc ggatgaagcc acgaggacca tcctggacat   1980
cagcccggta gtgcttgccc atgatgggct taatggcctc ggtggcctcg tccgcgttgt   2040
agaaggggat gctgctgacg tagtggtgga ggacatgagt ctcgatgatg ccgtggagaa   2100
ggtggcggcc gatgaagccc atctcacggt caatggtagc agcggcacca cggacgaagt   2160
tccactcgtc gttggtgtag tggggaaggg tagggtcggt gtgctggagg aaggtgatgg   2220
caacgagcca gtggttaacc cagaggtagg gaacaaagta ccagatggcc atgttgtaga   2280
aaccgaactt ctgaacgagg aagtacagag cagtggccat cagaccgata ccaatatcgc   2340
tgaggacgat gagcttagcg tcactgttct cgtacagagg gctgcgggga tcgaagtggt   2400
taacaccacc gccgaggccg ttatgcttgc ccttgccgcg accctcacgc tggcgctcgt   2460
ggtagttgtg gccggtaaca ttggtgatga ggtagttggg ccagccnacg annnnctcag   2520
taagatgagc gagctcgtgg gtcatctttc cgagacgagt agcctgctgc tcgcgggttc   2580
ggggaacgaa gaccatgtca cgctccatgt tgccagtggc cttgtggtgc tttcggtggg   2640
```

```
agatttgcca gctgaagtag gggacaagga gggaagagtg aagaacccag ccagtaatgt    2700
cgttgatgat gcgagaatcg gagaaagcac cgtgaccgca ctcatgggca ataacccaga    2760
gaccagtacc gaaaagaccc tgaagaacgg tgtacacggc ccacagacca gcgcgggcgg    2820
gggtggaggg gatatattcg ggggtcacaa agttgtacca gatgctgaaa gtggtagtca    2880
ggaggacaat gtcgcggagg atataaccgt atcccttgag agcggagcgc ttgaagcagt    2940
gcttagggat ggcattgtag atgtccttga tggtaaagtc gggaacctcg aactggttgc    3000
cgtaggtgtc gagcatgaca ccatactcgg acttgggctt ggcgatatca acctcggaca    3060
tggacgagag cgatgtggaa gaggccgagt ggcggggaga gtctgaagga gagacggcgg    3120
cagactcaga atccgtcaca gtagttgagg tgacggtgcg tctaagcgca gggttctgct    3180
tgggcagagc cgaagtggac gccatggaga gctgggttag tttgtgtaga gagtgtgtgt    3240
tgctagcgac tttcggattg tgtcattaca caaaacgcgt cgtctcgaca ctgatcttgt    3300
cgtggatact cacggctcgg acatcgtcgc cgacgatgac accggacttt cgcttaagga    3360
cgtcagtaac aggcattgtg tgatgtgtag tttagatttc gaatctgtgg ggaaagaaag    3420
gaaaaaagag actggcaacc gattgggaga gccactgttt atatataccc tagacaagcc    3480
ccccgcttgt aagatgttgg tcaatgtaaa ccagtattaa ggttggcaag tgcaggagaa    3540
gcaaggtgtg ggtaccgagc aatggaaatg tgccgaaggc aaaaaaatga ggccacggcc    3600
tattgtcggg gctatatcca gggggcgatt gaagtacact aacatgacat gtgtccacag    3660
accctcaatc tggcctgatg agccaaatcc atacgcgctt tcgcagctct aaaggctata    3720
acaagtcaca ccaccctgct cgacctcagc gccctcactt tttgttaaga caaactgtac    3780
acgctgttcc agcgttttct gcctgcacct ggtgggacat ttggtgcaac ctaaagtgct    3840
cggaacctct gtggtgtcca gatcagcgca gcagttccga ggtagttttg aggcccttag    3900
atgatgcaat ggtgtcagtc gctggatcac gagtcttaat ggcagtattc gttcttattt    3960
gtgccattga gccccgttat cctcgtatct tctaccccccc atcccatccc tttgttggtg    4020
caaccctacc catttattgt tgggtgcagc ccaaccgacg tggagagctt ggcttggcca    4080
tataaaaagg ccccccccta gtggcaatgg cagaaagtca gctgtgagtt gttgaatttg    4140
tcatctaggc ggcctggccg tcttctccgg ggcaattgtt cctctatagt actgcgtaca    4200
ctgtttaaac agtgtacgca gatctgcgac gacggaattc ctgcagccca tctgcagaat    4260
tcaggagaga ccgggttggc ggcgtatttg tgtcccaaaa aacagcccca attgccccaa    4320 ttgacccocaa attgacccag tagcgggccc aaccccggcg agagccccct tcaccccaca    4380
tatcaaacct cccccggttc ccacacttgc cgttaagggc gtagggtact gcagtctgga    4440
atctacgctt gttcagactt tgtactagtt tctttgtctg gccatccggg taacccatgc    4500
cggacgcaaa atagactact gaaaattttt ttgctttgtg gttgggactt tagccaaggg    4560
tataaaagac caccgtcccc gaattacctt tcctcttctt ttctctctct ccttgtcaac    4620
tcacacccga aatcgttaag catttccttc tgagtataag aatcattcac catggctgcc    4680
gctccctctg tgcgaacctt tacccgagcc gaggttctga acgctgaggc tctgaacgag    4740
ggcaagaagg acgctgaggc tcccttcctg atgatcatcg acaacaaggt gtacgacgtc    4800
cgagagttcg tccctgacca tcctggaggc tccgtgattc tcacccacgt tggcaaggac    4860
ggcaccgacg tctttgacac ctttcatccc gaggctgctt gggagactct cgccaacttc    4920
tacgttggag acattgacga gtccgaccga gacatcaaga acgatgactt tgccgctgag    4980
gtccgaaagc tgcgaacccct gttccagtct ctcggctact acgactcctc taaggcctac    5040
```

```
tacgccttca aggtctcctt caacctctgc atctggggac tgtccaccgt cattgtggcc   5100
aagtggggtc agacctccac cctcgccaac gtgctctctg ctgccctgct cggcctgttc   5160
tggcagcagt gcggatggct ggctcacgac tttctgcacc accaggtctt ccaggaccga   5220
ttctggggtg atctcttcgg agccttcctg ggaggtgtct gccagggctt ctcctcttcc   5280
tggtggaagg acaagcacaa cactcaccat gccgctccca acgtgcatgg cgaggatcct   5340
gacattgaca cccacccctct cctgacctgg tccgagcacg ctctggagat gttctccgac   5400
gtccccgatg aggagctgac ccgaatgtgg tctcgattca tggtcctgaa ccagacctgg   5460
ttctacttcc ccattctctc cttcgctcga ctgtcttggt gcctccagtc cattctcttt   5520
gtgctgccca acgtcaggc tcacaagccc tccggagctc gagtgcccat ctccctggtc   5580
gagcagctgt ccctcgccat gcactggacc tggtacctcg ctaccatgtt cctgttcatc   5640
aaggatcctg tcaacatgct cgtgtacttc ctggtgtctc aggctgtgtg cggaaacctg   5700
ctcgccatcg tgttctccct caaccacaac ggtatgcctg tgatctccaa ggaggaggct   5760
gtcgacatgg atttctttac caagcagatc atcactggtc gagatgtcca tcctggactg   5820
ttcgccaact ggttcaccgg tggcctgaac taccagatcg agcatcacct gttcccttcc   5880
atgcctcgac acaacttctc caagatccag cctgccgtcg agaccctgtg caagaagtac   5940
aacgtccgat accacaccac tggtatgatc gagggaactg ccgaggtctt ctcccgactg   6000
aacgaggtct ccaaggccac ctccaagatg ggcaaggctc agtaagcggc cgcatgagaa   6060
gataaatata taaatacatt gagatattaa atgcgctaga ttagagagcc tcatactgct   6120
cggagagaag ccaagacgag tactcaaagg ggattacacc atccatatcc acagacacaa   6180
gctggggaaa ggttctatat acactttccg gaataccgta gtttccgatg ttatcaatgg   6240
gggcagccag gatttcaggc acttcggtgt ctcggggtga atggcgttc ttggcctcca   6300 tcaagtcgta ccatgtcttc atttgcctgt caaagtaaaa cagaagcaga tgaagaatga   6360
acttgaagtg aaggaattta aattgccccg gagaagacgg ccaggccgcc tagatgacaa   6420
attcaacaac tcacagctga ctttctgcca ttgccactag gggggggcct ttttatatgg   6480
ccaagccaag ctctccacgt cggttgggct gcacccaaca ataaatgggt agggttgcac   6540
caacaaaggg atgggatggg gggtagaaga tacgaggata acgggctca atggcacaaa   6600 taagaacgaa tactgccatt aagactcgtg atccagcgac tgacaccatt gcatcatcta   6660
agggcctcaa aactacctcg gaactgctgc gctgatctgg acaccacaga ggttccgagc   6720
actttaggtt gcaccaaatg tcccaccagg tgcaggcaga aaacgctgga acagcgtgta   6780
cagtttgtct taacaaaaag tgagggcgct gaggtcgagc agggtggtgt gacttgttat   6840
agcctttaga gctgcgaaag cgcgtatgga tttggctcat caggccagat tgagggtctg   6900
tggacacatg tcatgttagt gtacttcaat cgccccctgg atatagcccc gacaataggc   6960
cgtggcctca ttttttttgcc ttccgcacat ttccattgct cggtacccac accttgcttc   7020
tcctgcactt gccaacccta atactggttt acattgacca acatcttaca agcgggggc   7080 ttgtctaggg tatatataaa cagtggctct cccaatcggt tgccagtctc ttttttcctt   7140 tctttccccca cagattcgaa atctaaacta cacatcacac aatgcctgtt actgacgtcc   7200
ttaagcgaaa gtccggtgtc atcgtcggcg acgatgtccg agccgtgagt atccacgaca   7260
agatcagtgt cgagacgacg cgttttgtgt aatgacacaa tccgaaagtc gctagcaaca   7320
cacactctct acacaaacta acccagctct ccatggagtc cattgctccc ttcctgccct   7380
```

```
ccaagatgcc tcaggacctg ttcatggacc tcgccagcgc tatcggtgtc cgagctgctc    7440
cctacgtcga tcccctggag gctgccctgg ttgcccaggc cgagaagtac attcccacca    7500
ttgtccatca cactcgaggc ttcctggttg ccgtggagtc tccctggct cgagagctgc    7560
ctctgatgaa ccccttccac gtgctcctga tcgtgctcgc ctacctggtc accgtgtttg    7620
tgggtatgca gatcatgaag aactttgaac gattcgaggt caagaccttc tccctcctgc    7680
acaacttctg tctggtctcc atctccgcct acatgtgcgg tggcatcctg tacgaggctt    7740
atcaggccaa ctatggactg tttgagaacg ctgccgatca caccttcaag ggtctcccta    7800
tggctaagat gatctggctc ttctacttct ccaagatcat ggagtttgtc gacaccatga    7860
tcatggtcct caagaagaac aaccgacaga tttcctttct gcacgtgtac caccactctt    7920
ccatcttcac catctggtgg ctggtcacct tcgttgctcc caacggtgaa gcctacttct    7980
ctgctgccct gaactccttc atccacgtca tcatgtacgg ctactacttt ctgtctgccc    8040
tgggcttcaa gcaggtgtcg ttcatcaagt tctacatcac tcgatcccag atgacccagt    8100
tctgcatgat gtctgtccag tcttcctggg acatgtacgc catgaaggtc cttggccgac    8160
ctggataccc cttcttcatc accgctctgc tctggttcta catgtggacc atgctcggtc    8220
tcttctacaa cttttaccga agaacgcca agctcgccaa gcaggccaag gctgacgctg    8280
ccaaggagaa ggccagaaag ctccagtaag cggccgcaag tgtggatggg gaagtgagtg    8340
cccggttctg tgtgcacaat tggcaatcca agatggatgg attcaacaca gggatatagc    8400
gagctacgtg gtggtgcgag gatatagcaa cggatattta tgtttgacac ttgagaatgt    8460
acgatacaag cactgtccaa gtacaatact aaacatactg tacatactca tactcgtacc    8520
cgggcaacgg tttcacttga gtgcagtggc tagtgctctt actcgtacag tgtgcaatac    8580
tgcgtatcat agtctttgat gtatatcgta ttcattcatg ttagttgcgt acgaagtcgt    8640
caatgatgtc gatatggggtt ttgatcatgc acacataagg tccgacctta tcggcaagct    8700
caatgagctc cttggtggtg gtaacatcca gagaagcaca caggttggtt ttcttggctg    8760
ccacgagctt gagcactcga gcggcaaagg cggacttgtg gacgttagct cgagcttcgt    8820
aggagggcat tttggtggtg aagaggagac tgaaataaat ttagtctgca gaacttttta    8880
tcggaacctt atctggggca gtgaagtata tgttatggta atagttacga gttagttgaa    8940
cttatagata gactggacta tacggctatc ggtccaaatt agaaagaacg tcaatggctc    9000
tctgggcgtc gcctttgccg acaaaaatgt gatcatgatg aaagccagca atgacgttgc    9060
agctgatatt gttgtcggcc aaccgcgccg aaaacgcagc tgtcagaccc acagcctcca    9120
acgaagaatg tatcgtcaaa gtgatccaag cacactcata gttggagtcg tactccaaag    9180
gcggcaatga cgagtcagac agatactcgt cgaccttttc cttgggaacc accaccgtca    9240
gcccttctga ctcacgtatt gtagccaccg acacaggcaa cagtccgtgg atagcagaat    9300
atgtcttgtc ggtccatttc tcaccaactt taggcgtcaa gtgaatgttg cagaagaagt    9360
atgtgccttc attgagaatc ggtgttgctg atttcaataa agtcttgaga tcagtttggc    9420
gcgccagctg cattaatgaa tcggccaacg cgcggggaga ggcggtttgc gtattgggcg    9480
ctcttccgct tcctcgctca ctgactcgct gcgctcggtc gttcggctgc ggcgagcggt    9540
atcagctcac tcaaaggcgg taatacggtt atccacagaa tcaggggata acgcaggaaa    9600
gaacatgtga gcaaaaggcc agcaaaaggc caggaaccgt aaaaaggccg cgttgctggc    9660
gttttttccat aggctccgcc cccctgacga gcatcacaaa aatcgacgct caagtcagag    9720
gtggcgaaac ccgacaggac tataaagata ccaggcgttt ccccctggaa gctccctcgt    9780
```

```
gcgctctcct gttccgaccc tgccgcttac cggatacctg tccgcctttc tcccttcggg   9840
aagcgtggcg ctttctcata gctcacgctg taggtatctc agttcggtgt aggtcgttcg   9900
ctccaagctg ggctgtgtgc acgaaccccc cgttcagccc gaccgctgcg ccttatccgg   9960
taactatcgt cttgagtcca acccggtaag acacgactta tcgccactgg cagcagccac  10020
tggtaacagg attagcagag cgaggtatgt aggcggtgct acagagttct gaagtggtg   10080 gcctaactac ggctacacta gaagaacagt atttggtatc tgcgctctgc tgaagccagt  10140
taccttcgga aaagagttg gtagctcttg atccggcaaa caaaccaccg ctggtagcgg   10200
tggttttttt gtttgcaagc agcagattac gcgcagaaaa aaggatctc aagaagatcc   10260 tttgatcttt tctacggggt ctgacgctca gtggaacgaa aactcacgtt aagggatttt  10320
ggtcatgaga ttatcaaaaa ggatcttcac ctagatcctt ttaaattaaa aatgaagttt  10380
taaatcaatc taaagtatat atgagtaaac ttggtctgac agttaccaat gcttaatcag  10440
tgaggcacct atctcagcga tctgtctatt tcgttcatcc atagttgcct gactccccgt  10500
cgtgtagata actacgatac gggagggctt accatctggc cccagtgctg caatgatacc  10560
gcgagaccca cgctcaccgg ctccagattt atcagcaata accagccag ccggaagggc   10620 cgagcgcaga gtggtcctg caactttatc cgcctccatc cagtctatta attgttgccg   10680
ggaagctaga gtaagtagtt cgccagttaa tagtttgcgc aacgttgttg ccattgctac  10740
aggcatcgtg gtgtcacgct cgtcgtttgg tatggcttca ttcagctccg gttcccaacg  10800
atcaaggcga gttacatgat cccccatgtt gtgcaaaaaa gcggttagct ccttcggtcc  10860
tccgatcgtt gtcagaagta agttggccgc agtgttatca ctcatggtta tggcagcact  10920
gcataattct cttactgtca tgccatccgt aagatgcttt tctgtgactg gtgagtactc  10980
aaccaagtca ttctgagaat agtgtatgcg gcgaccgagt tgctcttgcc cggcgtcaat  11040
acgggataat accgcgccac atagcagaac tttaaaagtg ctcatcattg gaaaacgttc  11100
ttcggggcga aaactctcaa ggatcttacc gctgttgaga tccagttcga tgtaacccac  11160
tcgtgcaccc aactgatctt cagcatcttt tactttcacc agcgtttctg ggtgagcaaa  11220
aacaggaagg caaaatgccg caaaaaaggg aataagggcg acacggaaat gttgaatact  11280
catactcttc ctttttcaat attattgaag catttatcag ggttattgtc tcatgagcgg  11340
atacatattt gaatgtattt agaaaaataa acaaataggg gttccgcgca catttccccg  11400
aaaagtgcca cctgatgcgg tgtgaaatac cgcacagatg cgtaaggaga aaataccgca  11460
tcaggaaatt gtaagcgtta atattttgtt aaaattcgcg ttaaattttt gttaaatcag  11520
ctcatttttt aaccaatagg ccgaaatcgg caaaatccct tataaatcaa agaatagac   11580 cgagataggg ttgagtgttg ttccagtttg gaacaagagt ccactattaa agaacgtgga  11640
ctccaacgtc aaagggcgaa aaaccgtcta tcagggcgat ggcccactac gtgaaccatc  11700
accctaatca agttttttgg ggtcgaggtg ccgtaaagca ctaaatcgga acccTaaagg  11760
gagcccccga tttagagctt gacggggaaa gccggcgaac gtggcgagaa aggaagggaa  11820
gaaagcgaaa ggagcgggcg ctagggcgct ggcaagtgta gcggtcacgc tgcgcgtaac  11880
caccacaccc gccgcgctta atgcgccgct agggcgcg tccattcgcc attcaggctg    11940
cgcaactgtt gggaagggcg atcggtgcgg gcctcttcgc tattacgcca gctggcgaaa  12000
gggggatgtg ctgcaaggcg attaagttgg gtaacgccag ggttttccca gtcacgacgt  12060
tgtaaaacga cggccagtga attgtaatac gactcactat agggcgaatt gggcccgacg  12120
```

```
tcgcatgcag tggtggtatt gtgactgggg atgtagttga gaataagtca tacacaagtc    12180
agctttcttc gagcctcata taagtataag tagttcaacg tattagcact gtacccagca    12240
tctccgtatc gagaaacaca acaacatgcc ccattggaca gatcatgcgg atacacaggt    12300
tgtgcagtat catacatact cgatcagaca ggtcgtctga ccatcataca agctgaacaa    12360
gcgctccata cttgcacgct ctctatatac acagttaaat tacatatcca tagtctaacc    12420
tctaacagtt aatcttctgg taagcctccc agccagcctt ctggtatcgc ttggcctcct    12480
caataggatc tcggttctgg ccgtacagac ctcggccgac aattatgata tccgttccgg    12540
tagacatgac atcctcaaca gttcggtact gctgtccgag agcgtctccc ttgtcgtcaa    12600
gacccacccc gggggtcaga ataagccagt cctcagagtc gcccttaat               12649

<210> SEQ ID NO 58
<211> LENGTH: 973
<212> TYPE: DNA
<213> ORGANISM: Yarrowia lipolytica
<220> FEATURE:
<221> NAME/KEY: misc_feature
<223> OTHER INFORMATION: Promoter FBAIN

<400> SEQUENCE: 58
aaattgcccc ggagaagacg gccaggccgc ctagatgaca aattcaacaa ctcacagctg      60
actttctgcc attgccacta ggggggggcc ttttttatatg gccaagccaa gctctccacg    120
tcggttgggc tgcacccaac aataaatggg tagggttgca ccaacaaagg gatgggatgg    180
ggggtagaag atacgaggat aacggggctc aatggcacaa ataagaacga atactgccat    240
taagactcgt gatccagcga ctgacaccat tgcatcatct aagggcctca aaactacctc    300
ggaactgctg cgctgatctg gacaccacag aggttccgag cactttaggt tgcaccaaat    360
gtcccaccag gtgcaggcag aaaacgctgg aacagcgtgt acagtttgtc ttaacaaaaa    420
gtgagggcgc tgaggtcgag cagggtggtg tgacttgtta tagcctttag agctgcgaaa    480
gcgcgtatgg atttggctca tcaggccaga ttgagggtct gtggacacat gtcatgttag    540
tgtacttcaa tcgcccctg gatatagccc cgacaatagg ccgtggcctc attttttgc     600 cttccgcaca tttccattgc tcggtaccca caccttgctt ctcctgcact tgccaacctt    660
aatactggtt tacattgacc aacatcttac aagcgggggg cttgtctagg gtatatataa    720
acagtggctc tcccaatcgg ttgccagtct ctttttttcct ttctttcccc acagattcga    780
aatctaaact acacatcaca caatgcctgt tactgacgtc cttaagcgaa agtccggtgt    840
catcgtcggc gacgatgtcc gagccgtgag tatccacgac aagatcagtg tcgagacgac    900
gcgttttgtg taatgacaca atccgaaagt cgctagcaac acacactctc tacacaaact    960
aacccagctc tcc                                                       973

<210> SEQ ID NO 59
<211> LENGTH: 957
<212> TYPE: DNA
<213> ORGANISM: Mortierella alpina

<400> SEQUENCE: 59
atggagtcca ttgctcccct cctgccctcc aagatgcctc aggacctgtt catggacctc     60
gccagcgcta tcggtgtccg agctgctccc tacgtcgatc ccctggaggc tgccctggtt    120
gcccaggccg agaagtacat tcccaccatt gtccatcaca ctcgaggctt cctggttgcc    180
gtggagtctc ccctggctcg agagctgcct ctgatgaacc ccttccacgt gctcctgatc    240
```

-continued

```
gtgctcgcct acctggtcac cgtgtttgtg ggtatgcaga tcatgaagaa ctttgaacga      300
ttcgaggtca agaccttctc cctcctgcac aacttctgtc tggtctccat ctccgcctac      360
atgtgcggtg gcatcctgta cgaggcttat caggccaact atggactgtt tgagaacgct      420
gccgatcaca ccttcaaggg tctccctatg ctaagatga tctggctctt ctacttctcc       480
aagatcatgg agtttgtcga caccatgatc atggtcctca agaagaacaa ccgacagatt      540
tcctttctgc acgtgtacca ccactcttcc atcttcacca tctggtggct ggtcaccttc      600
gttgctccca acggtgaagc ctacttctct gctgccctga actccttcat ccacgtcatc      660
atgtacggct actactttct gtctgccctg ggcttcaagc aggtgtcgtt catcaagttc      720
tacatcactc gatcccagat gacccagttc tgcatgatgt ctgtccagtc ttcctgggac      780
atgtacgcca tgaaggtcct tggccgacct ggatacccct tcttcatcac cgctctgctc      840
tggttctaca tgtggaccat gctcggtctc ttctacaact tttaccgaaa gaacgccaag      900
ctcgccaagc aggccaaggc tgacgctgcc aaggagaagg ccagaaagct ccagtaa        957
```

<210> SEQ ID NO 60
<211> LENGTH: 318
<212> TYPE: PRT
<213> ORGANISM: Mortierella alpina (GenBank Accession No. AX464731)

<400> SEQUENCE: 60

```
Met Glu Ser Ile Ala Pro Phe Leu Pro Ser Lys Met Pro Gln Asp Leu
1               5                   10                  15

Phe Met Asp Leu Ala Thr Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45

Thr Ile Val His His Thr Arg Gly Phe Leu Val Ala Val Glu Ser Pro
    50                  55                  60

Leu Ala Arg Glu Leu Pro Leu Met Asn Pro His Val Leu Leu Ile
65                  70                  75                  80

Val Leu Ala Tyr Leu Val Thr Val Phe Val Gly Met Gln Ile Met Lys
                85                  90                  95

Asn Phe Glu Arg Phe Glu Val Lys Thr Phe Ser Leu Leu His Asn Phe
            100                 105                 110

Cys Leu Val Ser Ile Ser Ala Tyr Met Cys Gly Gly Ile Leu Tyr Glu
        115                 120                 125

Ala Tyr Gln Ala Asn Tyr Gly Leu Phe Glu Asn Ala Ala Asp His Thr
    130                 135                 140

Phe Lys Gly Leu Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Met Ser Val Gln
                245                 250                 255
```

```
Ser Ser Trp Asp Met Tyr Ala Met Lys Val Leu Gly Arg Pro Gly Tyr
        260                 265                 270

Pro Phe Phe Ile Thr Ala Leu Leu Trp Phe Tyr Met Trp Thr Met Leu
        275                 280                 285

Gly Leu Phe Tyr Asn Phe Tyr Arg Lys Asn Ala Lys Leu Ala Lys Gln
        290                 295                 300

Ala Lys Ala Asp Ala Ala Lys Glu Lys Ala Arg Lys Leu Gln
305                 310                 315

<210> SEQ ID NO 61
<211> LENGTH: 1374
<212> TYPE: DNA
<213> ORGANISM: Mortierella alpina

<400> SEQUENCE: 61
atggctgccg ctccctctgt gcgaaccttt acccgagccg aggttctgaa cgctgaggct      60
ctgaacgagg gcaagaagga cgctgaggct cccttcctga tgatcatcga caacaaggtg     120
tacgacgtcc gagagttcgt ccctgaccat cctggaggct ccgtgattct cacccacgtt     180
ggcaaggacg gcaccgacgt cttttgacacc tttcatcccg aggctgcttg ggagactctc     240
gccaacttct acgttggaga cattgacgag tccaccgag acatcaagaa cgatgacttt     300
gccgctgagg tccgaaagct gcgaaccctg ttccagtctc tcggctacta cgactcctct     360
aaggcctact acgccttcaa ggtctccttc aacctctgca tctggggact gtccaccgtc     420
attgtggcca gtggggtca gacctccacc ctcgccaacg tgctctctgc tgccctgctc     480
ggcctgttct ggcagcagtg cggatggctg gctcacgact ttctgcacca ccaggtcttc     540
caggaccgat tctggggtga tctcttcgga gccttcctgg aggtgtctg ccagggcttc     600
tcctcttcct ggtggaagga caagcacaac actcaccatg ccgctcccaa cgtgcatggc     660
gaggatcctg acattgacac ccaccctctc ctgacctggt ccgagcacgc tctggagatg     720
ttctccgacg tccccgatga ggagctgacc cgaatgtggt ctcgattcat ggtcctgaac     780
cagacctggt tctacttccc cattctctcc ttcgctcgac tgtcttggtg cctccagtcc     840
attctctttg tgctgcccaa cggtcaggct cacaagccct ccggagctcg agtgcccatc     900
tccctggtcg agcagctgtc cctcgccatg cactggacct ggtacctcgc taccatgttc     960
ctgttcatca aggatcctgt caacatgctc gtgtacttcc tggtgtctca ggctgtgtgc    1020
ggaaacctgc tcgccatcgt gttctccctc aaccacaacg gtatgcctgt gatctccaag    1080
gaggaggctg tcgacatgga tttctttacc aagcagatca tcactggtcg agatgtccat    1140
cctggactgt tcgccaactg gttcaccggt ggcctgaact accagatcga gcatcacctg    1200
ttcccttcca tgcctcgaca caacttctcc aagatccagc ctgccgtcga gaccctgtgc    1260
aagaagtaca cgtccgata ccacaccact ggtatgatcg agggaactgc cgaggtcttc    1320
tcccgactga acgaggtctc caaggccacc tccaagatgg gcaaggctca gtaa           1374

<210> SEQ ID NO 62
<211> LENGTH: 457
<212> TYPE: PRT
<213> ORGANISM: Mortierella alpina (GenBank Accession No. AF465281)

<400> SEQUENCE: 62

Met Ala Ala Ala Pro Ser Val Arg Thr Phe Thr Arg Ala Glu Val Leu
1               5                   10                  15

Asn Ala Glu Ala Leu Asn Glu Gly Lys Lys Asp Ala Glu Ala Pro Phe
```

-continued

```
            20                  25                  30
Leu Met Ile Ile Asp Asn Lys Val Tyr Asp Val Arg Glu Phe Val Pro
         35                  40                  45

Asp His Pro Gly Gly Ser Val Ile Leu Thr His Val Gly Lys Asp Gly
 50                  55                  60

Thr Asp Val Phe Asp Thr Phe His Pro Glu Ala Ala Trp Glu Thr Leu
 65                  70                  75                  80

Ala Asn Phe Tyr Val Gly Asp Ile Asp Glu Ser Asp Arg Asp Ile Lys
                 85                  90                  95

Asn Asp Asp Phe Ala Ala Glu Val Arg Lys Leu Arg Thr Leu Phe Gln
                100                 105                 110

Ser Leu Gly Tyr Tyr Asp Ser Ser Lys Ala Tyr Tyr Ala Phe Lys Val
                115                 120                 125

Ser Phe Asn Leu Cys Ile Trp Gly Leu Ser Thr Val Ile Val Ala Lys
                130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
                165                 170                 175

His Gln Val Phe Gln Asp Arg Phe Trp Gly Asp Leu Phe Gly Ala Phe
                180                 185                 190

Leu Gly Gly Val Cys Gln Gly Phe Ser Ser Trp Trp Lys Asp Lys
                195                 200                 205

His Asn Thr His His Ala Ala Pro Asn Val His Gly Glu Asp Pro Asp
                210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
                260                 265                 270

Arg Leu Ser Trp Cys Leu Gln Ser Ile Leu Phe Val Leu Pro Asn Gly
                275                 280                 285

Gln Ala His Lys Pro Ser Gly Ala Arg Val Pro Ile Ser Leu Val Glu
                290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Leu Val Tyr Phe Leu Val Ser
                325                 330                 335

Gln Ala Val Cys Gly Asn Leu Leu Ala Ile Val Phe Ser Leu Asn His
                340                 345                 350

Asn Gly Met Pro Val Ile Ser Lys Glu Glu Ala Val Asp Met Asp Phe
                355                 360                 365

Phe Thr Lys Gln Ile Ile Thr Gly Arg Asp Val His Pro Gly Leu Phe
                370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Asn Val Arg Tyr His Thr Thr Gly Met
                420                 425                 430

Ile Glu Gly Thr Ala Glu Val Phe Ser Arg Leu Asn Glu Val Ser Lys
                435                 440                 445
```

Ala Thr Ser Lys Met Gly Lys Ala Gln
    450                 455

<210> SEQ ID NO 63
<211> LENGTH: 1001
<212> TYPE: DNA
<213> ORGANISM: Yarrowia lipolytica
<220> FEATURE:
<221> NAME/KEY: misc_feature
<223> OTHER INFORMATION: Promoter FBA

<400> SEQUENCE: 63

| | | | | | |
|---|---|---|---|---|---|
| taaacagtgt | acgcagtact | atagaggaac | aattgccccg | gagaagacgg | ccaggccgcc | 60 |
| tagatgacaa | attcaacaac | tcacagctga | ctttctgcca | ttgccactag | ggggggcctt | 120 |
| tttatatggc | caagccaagc | tctccacgtc | ggttgggctg | cacccaacaa | taaatgggta | 180 |
| gggttgcacc | aacaaaggga | tgggatgggg | ggtagaagat | acgaggataa | cggggctcaa | 240 |
| tggcacaaat | aagaacgaat | actgccatta | agactcgtga | tccagcgact | gacaccattg | 300 |
| catcatctaa | gggcctcaaa | actacctcgg | aactgctgcg | ctgatctgga | caccacagag | 360 |
| gttccgagca | ctttaggttg | caccaaatgt | cccaccaggt | gcaggcagaa | aacgctggaa | 420 |
| cagcgtgtac | agtttgtctt | aacaaaaagt | gagggcgctg | aggtcgagca | gggtggtgtg | 480 |
| acttgttata | gcctttagag | ctgcgaaagc | gcgtatggat | ttggctcatc | aggccagatt | 540 |
| gagggtctgt | ggacacatgt | catgttagtg | tacttcaatc | gcccctgga | tatagccccg | 600 |
| acaataggcc | gtggcctcat | ttttttgcct | tccgcacatt | tccattgctc | ggtacccaca | 660 |
| ccttgcttct | cctgcacttg | ccaaccttaa | tactggttta | cattgaccaa | catcttacaa | 720 |
| gcgggggggct | tgtctagggt | atatataaac | agtggctctc | ccaatcggtt | gccagtctct | 780 |
| tttttccttt | ctttccccac | agattcgaaa | tctaaactac | acatcacaca | atgcctgtta | 840 |
| ctgacgtcct | taagcgaaag | tccggtgtca | tcgtcggcga | cgatgtccga | gccgtgagta | 900 |
| tccacgacaa | gatcagtgtc | gagacgacgc | gttttgtgta | atgacacaat | ccgaaagtcg | 960 |
| ctagcaacac | acactctcta | cacaaactaa | cccagctctc | c | | 1001 |

<210> SEQ ID NO 64
<211> LENGTH: 819
<212> TYPE: DNA
<213> ORGANISM: Thraustochytrium aureum

<400> SEQUENCE: 64

| | | | | | |
|---|---|---|---|---|---|
| atggccaact | cctctgtctg | ggacgacgtg | gtcggacgag | tcgagaccgg | tgtcgaccag | 60 |
| tggatggacg | gagctaagcc | ctacgctctg | accgacggtc | tgcccatgat | ggacgtctcc | 120 |
| accatgctcg | ccttcgaggt | cggctacatg | gccatgctgc | tcttcggcat | tcccatcatg | 180 |
| aagcagatgg | agaagccctt | cgagctgaag | accatcaagc | tgctccacaa | cctgttcctc | 240 |
| ttcggactgt | ccctctacat | gtgcgtcgag | accatccgac | aggctatcct | gggtggctac | 300 |
| aaggtcttcg | gcaacgacat | ggagaagggc | aacgagtccc | acgctcaggg | catgtcccga | 360 |
| atcgtctacg | tgttctacgt | ctccaaggcc | tacgagttcc | tggacaccgc | tatcatgatc | 420 |
| ctgtgcaaga | agttcaacca | ggtctccttc | ctgcacgtgt | accaccatgc | caccatcttc | 480 |
| gccatctggt | gggctattgc | caagtacgct | cctggtggcg | acgcctactt | ctccgtcatc | 540 |
| ctcaactcct | tcgtccacac | cgtcatgtac | gcctactact | tcttttcctc | tcagggcttc | 600 |
| ggcttcgtca | agcccatcaa | gccctacatc | accactctgc | agatgaccca | gttcatggct | 660 |

-continued

```
atgctggtgc agtccctgta cgactacctc ttcccctgcg actaccctca ggctctggtc    720
cagctgctcg gcgtgtacat gatcaccctg ctcgctctgt tcggcaactt ctttgtccag    780
tcctacctga agaagcccaa gaagtccaag accaactaa                            819
```

<210> SEQ ID NO 65
<211> LENGTH: 272
<212> TYPE: PRT
<213> ORGANISM: Thraustochytrium aureum

<400> SEQUENCE: 65

```
Met Ala Asn Ser Ser Val Trp Asp Asp Val Val Gly Arg Val Glu Thr
1               5                   10                  15

Gly Val Asp Gln Trp Met Asp Gly Ala Lys Pro Tyr Ala Leu Thr Asp
            20                  25                  30

Gly Leu Pro Met Met Asp Val Ser Thr Met Leu Ala Phe Glu Val Gly
        35                  40                  45

Tyr Met Ala Met Leu Leu Phe Gly Ile Pro Ile Met Lys Gln Met Glu
    50                  55                  60

Lys Pro Phe Glu Leu Lys Thr Ile Lys Leu Leu His Asn Leu Phe Leu
65                  70                  75                  80

Phe Gly Leu Ser Leu Tyr Met Cys Val Glu Thr Ile Arg Gln Ala Ile
                85                  90                  95

Leu Gly Gly Tyr Lys Val Phe Gly Asn Asp Met Glu Lys Gly Asn Glu
            100                 105                 110

Ser His Ala Gln Gly Met Ser Arg Ile Val Tyr Val Phe Tyr Val Ser
        115                 120                 125

Lys Ala Tyr Glu Phe Leu Asp Thr Ala Ile Met Ile Leu Cys Lys Lys
    130                 135                 140

Phe Asn Gln Val Ser Phe Leu His Val Tyr His His Ala Thr Ile Phe
145                 150                 155                 160

Ala Ile Trp Trp Ala Ile Ala Lys Tyr Ala Pro Gly Gly Asp Ala Tyr
                165                 170                 175

Phe Ser Val Ile Leu Asn Ser Phe Val His Thr Val Met Tyr Ala Tyr
            180                 185                 190

Tyr Phe Phe Ser Ser Gln Gly Phe Gly Phe Val Lys Pro Ile Lys Pro
        195                 200                 205

Tyr Ile Thr Thr Leu Gln Met Thr Gln Phe Met Ala Met Leu Val Gln
    210                 215                 220

Ser Leu Tyr Asp Tyr Leu Phe Pro Cys Asp Tyr Pro Gln Ala Leu Val
225                 230                 235                 240

Gln Leu Leu Gly Val Tyr Met Ile Thr Leu Leu Ala Leu Phe Gly Asn
                245                 250                 255

Phe Phe Val Gln Ser Tyr Leu Lys Lys Pro Lys Lys Ser Lys Thr Asn
            260                 265                 270
```

<210> SEQ ID NO 66
<211> LENGTH: 10
<212> TYPE: DNA
<213> ORGANISM: Yarrowia lipolytica
<220> FEATURE:
<221> NAME/KEY: misc_feature
<222> LOCATION: (8)..(8)
<223> OTHER INFORMATION: n is a, c, g, or t

<400> SEQUENCE: 66

```
mammatgnhs                                                            10
```

Δ12 DESATURASES SUITABLE FOR ALTERING LEVELS OF POLYUNSATURATED FATTY ACIDS IN OLEAGINOUS YEAST

This application claims the benefit of U.S. Provisional Application No. 60/519,191, filed Nov. 12, 2003, and U.S. Provisional Application No. 60/570,679, filed May 13, 2004.

FIELD OF THE INVENTION

This invention is in the field of biotechnology. More specifically, this invention pertains to the identification of nucleic acid fragments encoding Δ12 fatty acid desaturase enzymes useful for disrupting or enhancing the production of polyunsaturated fatty acids in oleaginous microorganisms, such as oleaginous yeast.

BACKGROUND OF THE INVENTION

It has long been recognized that certain polyunsaturated fatty acids, or PUFAs, are important biological components of healthy cells. For example, such PUFAs are recognized as:
  "Essential" fatty acids that can not be synthesized de novo in mammals and instead must be obtained either in the diet or derived by further desaturation and elongation of linoleic acid (LA) or α-linolenic acid (ALA);
  Constituents of plasma membranes of cells, where they may be found in such forms as phospholipids or triglycerides;
  Necessary for proper development, particularly in the developing infant brain, and for tissue formation and repair; and,
  Precursors to several biologically active eicosanoids of importance in mammals, including prostacyclins, eicosanoids, leukotrienes and prostaglandins.

In the 1970's, observations of Greenland Eskimos linked a low incidence of heart disease and a high intake of long-chain ω-3 PUFAs (Dyerberg, J. et al., *Amer. J. Clin Nutr.* 28:958-966 (1975); Dyerberg, J. et al., *Lancet* 2(8081):117-119 (Jul. 15, 1978)). More recent studies have confirmed the cardiovascular protective effects of ω-3 PUFAs (Shimokawa, H., *Word Rev Nutr Diet*, 88:100-108 (2001); von Schacky, C., and Dyerberg, J., *World Rev Nutr Diet*, 88:90-99 (2001)). Further, it has been discovered that several disorders respond to treatment with ω-3 fatty acids, such as the rate of restenosis after angioplasty, symptoms of inflammation and rheumatoid arthritis, asthma, psoriasis and eczema. γ-Linolenic acid (GLA, an ω-6 PUFA) has been shown to reduce increases in blood pressure associated with stress and to improve performance on arithmetic tests. GLA and dihomo-γ-linolenic acid (DGLA, another ω-6 PUFA) have been shown to inhibit platelet aggregation, cause vasodilation, lower cholesterol levels and inhibit proliferation of vessel wall smooth muscle and fibrous tissue (Brenner et al., *Adv. Exp. Med. Biol.* 83: 85-101 (1976)). Administration of GLA or DGLA, alone or in combination with eicosapentaenoic acid (EPA, an ω-3 PUFA), has been shown to reduce or prevent gastrointestinal bleeding and other side effects caused by non-steroidal anti-inflammatory drugs (U.S. Pat. No. 4,666,701). Further, GLA and DGLA have been shown to prevent or treat endometriosis and premenstrual syndrome (U.S. Pat. No. 4,758,592) and to treat myalgic encephalomyelitis and chronic fatigue after viral infections (U.S. Pat. No. 5,116,871). Other evidence indicates that PUFAs may be involved in the regulation of calcium metabolism, suggesting that they may be useful in the treatment or prevention of osteoporosis and kidney or urinary tract stones. Finally, PUFAs can be used in the treatment of cancer and diabetes (U.S. Pat. No. 4,826,877; Horrobin et al., *Am. J. Clin. Nutr.* 57 (Suppl.): 732S-737S (1993)).

PUFAs are generally divided into two major classes (consisting of the ω-6 and the ω-3 fatty acids) that are derived by desaturation and elongation of the essential fatty acids, LA and ALA, respectively. Despite a variety of commercial sources of PUFAs from natural sources [e.g., seeds of evening primrose, borage and black currants; filamentous fungi (*Mortierella*), *Porphyridium* (red alga), fish oils and marine plankton (*Cyclotella, Nitzschia, Crypthecodinium*)], there are several disadvantages associated with these methods of production. First, natural sources such as fish and plants tend to have highly heterogeneous oil compositions. The oils obtained from these sources therefore can require extensive purification to separate or enrich one or more of the desired PUFAs. Natural sources are also subject to uncontrollable fluctuations in availability (e.g., due to weather, disease, or over-fishing in the case of fish stocks); and, crops that produce PUFAs often are not competitive economically with hybrid crops developed for food production. Large-scale fermentation of some organisms that naturally produce PUFAs (e.g., *Porphyridium, Mortierella*) can also be expensive and/or difficult to cultivate on a commercial scale.

As a result of the limitations described above, extensive work has been conducted toward: 1.) the development of recombinant sources of PUFAs that are easy to produce commercially; and 2.) modification of fatty acid biosynthetic pathways, to enable production of desired PUFAs. For example, advances in the isolation, cloning and manipulation of fatty acid desaturase and elongase genes from various organisms have been made over the last several years. Knowledge of these gene sequences offers the prospect of producing a desired fatty acid and/or fatty acid composition in novel host organisms that do not naturally produce PUFAs. The literature reports a number of examples in *Saccharomyces cerevisiae*, such as: Domergue, F., et al. (*Eur. J. Biochem.* 269:4105-4113 (2002)), wherein two desaturases from the marine diatom *Phaeodactylum tricomutum* were cloned into *S. cerevisiae*, leading to the production of EPA; Beaudoin F., et al. (*Proc. Natl. Acad. Sci. U.S.A.* 97(12):6421-6 (2000)), wherein the ω-3 and ω-6 PUFA biosynthetic pathways were reconstituted in *S. cerevisiae*, using genes from *Caenorhabditis elegans*; Dyer, J. M., et al. (*Appl. Env. Microbiol.*, 59:224-230 (2002)), wherein plant fatty acid desaturases (FAD2 and FAD3) were expressed in *S. cerevisiae*, leading to the production of ALA; and, U.S. Pat. No. 6,136,574 (Knutzon et al., Abbott Laboratories), wherein one desaturase from *Brassica napus* and two desaturases from the fungus *Mortierella alpina* were cloned into *S. cerevisiae*, leading to the production of LA, GLA, ALA and STA. There remains a need, however, for an appropriate microbial system in which these types of genes can be expressed to provide for economical production of commercial quantities of one or more PUFAs. Additionally, a need exists for oils enriched in specific PUFAs, notably EPA and DHA.

One class or microorganisms that has not been previously examined as a production platform for PUFAs are the oleaginous yeast. These organisms can accumulate oil up to 80% of their dry cell weight. The technology for growing oleaginous yeast with high oil content is well developed (for example, see EP 0 005 277B1; Ratledge, C., *Prog. Ind. Microbiol.* 16:119-206 (1982)), and may offer a cost advantage compared to commercial micro-algae fermentation for production of ω-3-or ω-6 PUFAs. Whole yeast cells may also represent a convenient way of encapsulating ω-3 or ω-6 PUFA-enriched oils for use in functional foods and animal feed supplements.

Despite the advantages noted above, most oleaginous yeast are naturally deficient in ω-6 and ω-3 PUFAs, since naturally produced PUFAs in these organisms are usually limited to 18:2 fatty acids (and less commonly, 18:3 fatty acids). Thus, the problem to be solved is to develop an oleaginous yeast that accumulates oils enriched in ω-3 and/or ω-6 fatty acids. Toward this end, it is not only necessary to introduce the required desaturases and elongases that allow for the synthesis and accumulation of ω-3 and/or ω-6 fatty acids in oleaginous yeast, but also to increase the availability of the 18:2 substrate (i.e., LA). Generally, the availability of this substrate is controlled by the activity of Δ12 desaturases that catalyze the conversion of oleic acid to LA.

There are a variety of known Δ12 desaturases disclosed in the public literature, some of which originate from fungal sources (e.g., *Mortierella alpina, Emericella nidulans, Mucor rouxii*). These desaturases are not known to be effective for altering fatty acid composition in oleaginous yeast, although the *Mortierella alpina* desaturase, for example, has previously been expressed in the non-oleaginous yeast *Saccharomyces cerevisiae* and enabled accumulation of 18:2 (Sakuradani E., et al., *Eur J Biochem.* 261 (3):812-20 (1999)). WO 2003/099216 describes Δ12 desaturases from *Neurospora crassa* and *Botrytis cinerea*. Subsequent expression analysis in *S. cerevisiae* confirmed the ability of the *N. crassa* desaturase to convert oleic acid to 18:2; however, the percent substrate conversion for this reaction was only 68% (calculated as ([18:2]/[18:1+18:2])*100). Thus, there is need for the identification and isolation of genes encoding Δ12 desaturases that are able to support production of high levels of 18:2 (LA) in oil-producing host organisms (e.g., oleaginous yeast) for use in the production of PUFAs.

Applicants have solved the stated problem by isolating the gene encoding a Δ12 desaturase from the fungus *Fusarium moniliforme* and demonstrating surprisingly efficient conversion of oleic acid to 18:2 (LA) upon expression in an oleaginous yeast. Furthermore, orthologs of this Δ12 desaturase have been identified in *Aspergillus nidulans, Aspergillus flavus, Aspergillus fumigatus, Magnaporthe grisea, Neurospora crassa* and *Fusarium graminearium*.

SUMMARY OF THE INVENTION

The invention relates to a gene encoding a Δ12 desaturase enzyme isolated from *Fusarium* useful for the manipulation of the biochemical pathway leading to the production of ω-3 and ω-6 fatty acids. Accordingly, the invention provides an isolated nucleic acid fragment encoding a fungal Δ12 desaturase enzyme, selected from the group consisting of:

(a) an isolated nucleic acid fragment encoding the amino acid sequence as set forth in SEQ ID NO:4;

(b) an isolated nucleic acid fragment that hybridizes with (a) under the following hybridization conditions: 0.1× SSC, 0.1% SDS, 65° C. and washed with 2×SSC, 0.1% SDS followed by 0.1×SSC, 0.1% SDS; or (c) an isolated nucleic acid fragment that is complementary to (a) or (b).

In one specific embodiment the invention provides an isolated nucleic acid fragment comprising a first nucleotide sequence, encoding a Δ12 desaturase enzyme, having at least 89.2% identity based on the Clustal method of alignment when compared to the nucleic acid fragment having the sequence as set forth in SEQ ID NO:3;

or a second nucleotide sequence comprising the complement of the first nucleotide sequence.

Similarly the invention provides an isolated nucleic acid fragment comprising a first nucleotide sequence encoding a Δ12 desaturase enzyme of at least 477 amino acids that has at least 95% identity based on the Clustal method of alignment when compared to a polypeptide having the sequence as set forth in SEQ ID NO:4;

or a second nucleotide sequence comprising the complement of the first nucleotide sequence.

Similarly the invention provides polypeptides encoded by the isolated nucleic acids of the invention as well as genetic chimera of these nucleic acids and transformed host cells comprising the same.

In another embodiment the invention provides a method of obtaining a nucleic acid fragment encoding a Δ12 desaturase enzyme comprising:

(a) probing a genomic library with the nucleic acid fragment of the invention;

(b) identifying a DNA clone that hybridizes with the nucleic acid fragment of the invention; and (c) sequencing the genomic fragment that comprises the clone identified in step (b), wherein the sequenced genomic fragment encodes a Δ12 desaturase enzyme.

Similarly the invention provides a method of obtaining a nucleic acid fragment encoding a Δ12 desaturase enzyme comprising:

(a) synthesizing at least one oligonucleotide primer corresponding to a portion of the sequence as set forth in SEQ ID NOs:4, 8, 12, 16, 20, 21 and 22; and (b) amplifying an insert present in a cloning vector using the oligonucleotide primer of step (a);

wherein the amplified insert encodes a portion of an amino acid sequence encoding a Δ12 desaturase enzyme.

In another embodiment the invention provides a method for producing linoleic acid comprising:

a) providing an oleaginous yeast comprising:

(i) an isolated nucleic acid fragment encoding a fungal polypeptide having Δ12 desaturase activity that has at least 56.3% identity based on the Clustal method of alignment when compared to a polypeptide having the sequence as set forth in SEQ ID NO:4; and (ii) a source of oleic acid;

b) growing the yeast of step (a) under conditions wherein the chimeric desaturase gene is expressed and the oleic acid is converted to linoleic acid; and c) optionally recovering the linoleic acid of step (b).

Similarly the invention provides a method for the production of ω-3 or ω-6 polyunsaturated fatty acids comprising:

a) providing an oleaginous yeast comprising:

(i) an isolated nucleic acid fragment encoding a protein having Δ12 desaturase activity that has at least 56.3% identity based on the Clustal method of alignment when compared to a polypeptide having the sequence as set forth in SEQ ID NO:4; and (ii) genes encoding a functional ω-3/ω-6 fatty acid biosynthetic pathway;

b) providing a source of desaturase substrate comprising oleic acid; and c) contacting the oleaginous yeast of (a) with the desaturase substrate of (b) wherein polyunsaturated fatty acids are produced; and d) optionally recovering the polyunsaturated fatty acids of step (c).

Additionally the invention provides microbial oils produced by the methods of the invention.

BRIEF DESCRIPTION OF THE DRAWINGS AND SEQUENCE DESCRIPTIONS

FIG. 5 shows a pairwise comparison (% Identity) between and among proteins from different filamentous fungi (i.e., *Aspergillus nidulans, Fusarium moniliforme, F. graminearium, Magnaporthe grisea* and *Neurospora crassa*) having homology to the *Yarrowia lipolytica* Δ12 desaturase enzyme using a ClustalW analysis (Megalign program of DNASTAR sofware).

FIG. 6 shows a pairwise comparison (% Identity) between proteins from different filamentous fungi having homology to the *Yarrowia lipolytica* Δ12 desaturase and Δ12 desaturase proteins from some other fungal and non-fungal species using a ClustalW analysis (Megalign program of DNASTAR sofware).

Figure 7:
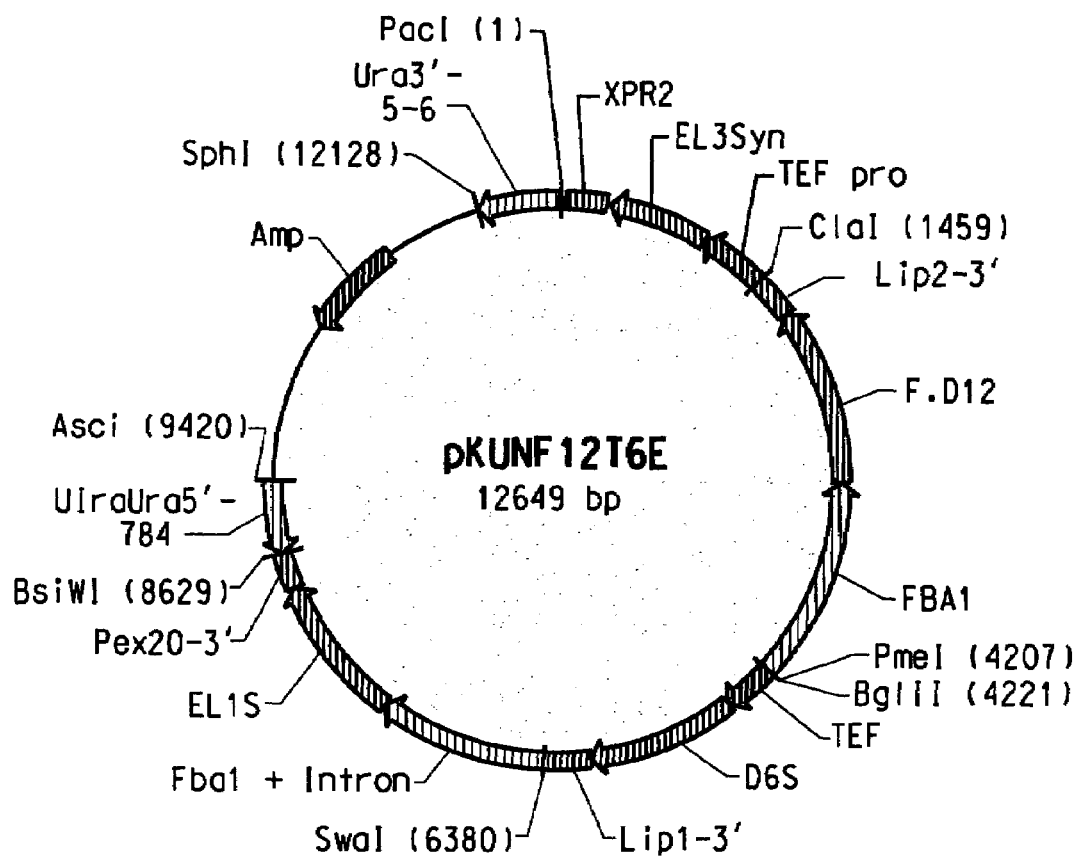

FIG. 7 provides a plasmid map for pKUNF12T6E.

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-22, 51 and 52 are ORFs encoding genes or proteins as identified in Table 1.

TABLE 1

Summary Of Desaturase Gene And Protein SEQ ID Numbers

| Description | ORF Nucleic acid SEQ ID NO. | Protein SEQ ID NO. |
|---|---|---|
| *Fusarium moniliforme* sub-family 1 desaturase (Δ15/Δ12 desaturase) | 1 (1209 bp) | 2 (402 AA) |
| *Fusarium moniliforme* sub-family 2 desaturase (Δ12 desaturase) | 3 (1434 bp) | 4 (477 AA) |
| *Aspergillus nidulans* sub-family 1 desaturase (Δ15 desaturase) | 5 (1206 bp) | 6 (401 AA) |
| *Aspergillus nidulans* sub-family 2 desaturase (Δ12 desaturase) | 7 (1416 bp) | 8 (471 AA) |
| *Magnaporthe grisea* sub-family 1 desaturase (Δ15 desaturase) | 9 (1185 bp) | 10 (394 AA) |
| *Magnaporthe grisea* sub-family 2 desaturase (Δ12 desaturase) | 11 (1656 bp) | 12 (551 AA) |
| *Neurospora crassa* sub-family 1 desaturase (Δ15 desaturase) | 13 (1290 bp) | 14 (429 AA) |
| *Neurospora crassa* sub-family 2 desaturase (Δ12 desaturase) | 15 (1446 bp) | 16 (481 AA) |
| *Fusarium graminearium* sub-family 1 desaturase (Δ15 desaturase) | 17 (1212 bp) | 18 (403 AA) |
| *Fusarium graminearium* sub-family 2 desaturase (Δ12 desaturase) | 19 (1371 bp) | 20 (456 AA) |
| *Aspergillus fumigatus* sub-family 2 desaturase (Δ12 desaturase) | — | 21 (424 AA) |
| *Aspergillus flavus* sub-family 2 desaturase (Δ12 desaturase) | — | 22 (466 AA) |
| *Yarrowia lipolytica* Δ12 desaturase | 51 (1936 bp) | 52 (419 AA) |

SEQ ID NOs:23 and 24 are primers TEF 5' and TEF 3', respectively, used to isolate the TEF promoter.

SEQ ID NOs:25 and 26 are primers XPR 5' and XPR 3', respectively, used to isolate the XPR2 transcriptional terminator.

SEQ ID NOs:27-38 correspond to primers YL5, YL6, YL9, YL10, YL7, YL8, YL3, YL4, YL1, YL2, YL61 and YL62, respectively, used for plasmid construction.

SEQ ID NOs:39 and 41 are the degenerate primers identified as P73 and P76, respectively, used for the isolation of a *Yarrowia lipolytica* Δ12 desaturase gene.

SEQ ID NOs:40 and 42 are the amino acid consensus sequences that correspond to the degenerate primers P73 and P76, respectively.

SEQ ID NOs:43-46 correspond to primers P99, P100, P101 and P102, respectively, used for targeted disruption of the native *Y. lipolytica* Δ12 desaturase gene.

SEQ ID NOs:47-50 correspond to primers P119, P120, P121 and P122, respectively, used to screen for targeted integration of the disrupted *Y. lipolytica* Δ12 desaturase gene.

SEQ ID NOs:53 and 54 correspond to primers P147 and P148, respectively, used to amplify the full-length *Y. lipolytica* Δ12 desaturase coding region.

SEQ ID NOs:55 and 56 correspond to primers P194 and P195, respectively, used to amplify the full-length *Fusarium moniliforme* Δ12 desaturase coding region.

SEQ ID NO:57 provides the DNA sequence of plasmid pKUNF12T6E.

SEQ ID NO:58 corresponds to the *Yarrowia lipolytica* FBAIN promoter region.

SEQ ID NO:59 is the 957 bp nucleotide sequence of a synthetic elongase 1 gene derived from *Mortierella alpina*, codon-optimized for expression in *Y. lipolytica*, while SEQ ID NO:60 is the corresponding 318 amino acid sequence.

SEQ ID NO:61 is the 1374 bp nucleotide sequence of a synthetic Δ6 desaturase gene derived from *Mortierella alpina*, codon-optimized for expression in *Y. lipolytica*, while SEQ ID NO:62 is the corresponding 457 amino acid sequence.

SEQ ID NO:63 corresponds to the *Yarrowia lipolytica* FBA promoter region.

SEQ ID NO:64 is the 819 bp nucleotide sequence of a synthetic elongase 2 gene derived from *Thraustochytrium aureum*, codon-optimized for expression in *Y. lipolytica*, while SEQ ID NO:65 is the corresponding 272 amino acid sequence.

SEQ ID NO:66 corresponds to the codon-optimized translation initiation site for genes optimally expressed in *Yarrowia* sp.

DETAILED DESCRIPTION OF THE INVENTION

In accordance with the subject invention, Applicants have isolated and confirmed the identity of a *Fusarium moniliforme* gene encoding a Δ12 desaturase and identified its orthologs in other fungi. Additionally, methods and compositions are provided which permit modification of the long-chain polyunsaturated fatty acid (PUFA) content and composition of oleaginous yeast, such as *Yarrowia lipolytica*.

The invention relates to novel Δ12 desaturase enzymes and genes encoding the same that may be used for the manipulation of biochemical pathways for the production of healthful PUFAs. Thus, the subject invention finds many applications. PUFAs, or derivatives thereof, made by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary). In this case, the PUFAs are generally administered orally but can be administered by any route by which they may be successfully absorbed, e.g., parenterally (e.g., subcutaneously, intramuscularly or intravenously), rectally, vaginally or topically (e.g., as a skin ointment or lotion).

Supplementation of humans or animals with PUFAs produced by recombinant means can result in increased levels of the added PUFAs, as well as their metabolites. For example, treatment with arachidonic acid (ARA) can result not only in increased levels of ARA, but also downstream products of ARA such as prostaglandins. Complex regulatory mechanisms can make it desirable to combine various PUFAs, or add different conjugates of PUFAs, in order to prevent, control or overcome such mechanisms to achieve the desired levels of specific PUFAs in an individual.

definitions

In this disclosure, a number of terms and abbreviations are used. The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

The term "*Fusarium moniliforme*" is synonymous with "*Fusarium verticillioides*".

The term "fatty acids" refers to long-chain aliphatic acids (alkanoic acids) of varying chain length, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon atoms in the particular fatty acid and Y is the number of double bonds.

Generally, fatty acids are classified as saturated or unsaturated. The term "saturated fatty acids" refers to those fatty acids that have no "double bonds" between their carbon backbone. In contrast, "unsaturated fatty acids" have "double bonds" along their carbon backbones (which are most commonly in the cis-configuration). "Monounsaturated fatty acids" have only one "double bond" along the carbon backbone (e.g., usually between the $9^{th}$ and $10^{th}$ carbon atom as for palmitoleic acid (16:1) and oleic acid (18:1)), while "polyunsaturated fatty acids" (or "PUFAs") have at least two double bonds along the carbon backbone (e.g., between the $9^{th}$ and $10^{th}$, and $12^{th}$ and $13^{th}$ carbon atoms for linoleic acid (18:2); and between the $9^{th}$ and $10^{th}$, $12^{th}$ and $13^{th}$, and $15^{th}$ and $16^{th}$ for α-linolenic acid (18:3)).

"PUFAs" can be classified into two major families (depending on the position (n) of the first double bond nearest the methyl end of the fatty acid carbon chain). Thus, the "omega-6 fatty acids" (ω-6 or n-6) have the first unsaturated double bond six carbon atoms from the omega (methyl) end of the molecule and additionally have a total of two or more double bonds, with each subsequent unsaturation occurring 3 additional carbon atoms toward the carboxyl end of the molecule. In contrast, the "omega-3 fatty acids" (ω-3 or n-3) have the first unsaturated double bond three carbon atoms away from the omega end of the molecule and additionally have a total of three or more double bonds, with each subsequent unsaturation occurring 3 additional carbon atoms toward the carboxyl end of the molecule.

For the purposes of the present disclosure, the omega-reference system will be used to indicate the number of carbons, the number of double bonds and the position of the double bond closest to the omega carbon, counting from the omega carbon (which is numbered 1 for this purpose). This nomenclature is shown below in Table 2, in the column titled "Shorthand Notation". The remainder of the Table summarizes the common names of (ω-3 and ω-6 fatty acids, the abbreviations that will be used throughout the specification, and each compounds' chemical name.

TABLE 2

Nomenclature Of Polyunsaturated Fatty Acids

| Common Name | Abbreviation | Chemical Name | Shorthand Notation |
|---|---|---|---|
| Linoleic | LA | cis-9, 12-octadecadienoic | 18:2 ω-6 |
| γ-Linolenic | GLA | cis-6, 9, 12-octadecatrienoic | 18:3 ω-6 |
| Eicosadienoic | EDA | cis-11, 14- eicosadienoic | 20:2 ω-6 |
| Dihomo-γ-Linoleic | DGLA | cis-8, 11, 14-eicosatrienoic | 20:3 ω-6 |
| Arachidonic | ARA | cis-5, 8, 11, 14-eicosatetraenoic | 20:4 ω-6 |
| α-Linolenic | ALA | cis-9, 12, 15-octadecatrienoic | 18:3 ω-3 |
| Stearidonic | STA | cis-6, 9, 12, 15-octadecatetraenoic | 18:4 ω-3 |
| Eicosatrienoic | ETrA | cis-11, 14, 17-eicosatrienoic | 20:3 ω-3 |
| Eicosatetraenoic | ETA | cis-8, 11, 14, 17-eicosatetraenoic | 20:4 ω-3 |
| Eicosapentaenoic | EPA | cis-5, 8, 11, 14, 17-eicosapentaenoic | 20:5 ω-3 |
| Docosapentaenoic | DPA | cis-7, 10, 13, 16, 19-docosapentaenoic | 22:5 ω-3 |
| Docosahexaenoic | DHA | cis-4, 7, 10, 13, 16, 19-docosahexaenoic | 22:6 ω-3 |

The term "essential fatty acid" refers to a particular PUFA that an individual must ingest in order to survive, being unable to synthesize the particular essential fatty acid de novo. Linoleic (18:2, ω-6) and linoleic (18:3, ω-3) fatty acids are "essential fatty acids", since humans cannot synthesize them and have to obtain them in their diet.

The term "fat" refers to a lipid substance that is solid at 25° C. and usually saturated.

The term "oil" refers to a lipid substance that is liquid at 25° C. and usually polyunsaturated. PUFAs are found in the oils of some algae, oleaginous yeast and filamentous fungi. "Microbial oils" or "single cell oils" are those oils naturally produced by microorganisms during their lifespan. Such oils can contain long-chain PUFAs.

The term "PUFA biosynthetic pathway enzyme" refers to any of the following enzymes (and genes which encode said enzymes) associated with the biosynthesis of a PUFA, including: a Δ4 desaturase, a Δ5 desaturase, a Δ6 desaturase, a Δ12 desaturase, a Δ15 desaturase, a Δ17 desaturase, a Δ9 desaturase, a Δ8 desaturase and/or an elongase(s).

Figure 2:
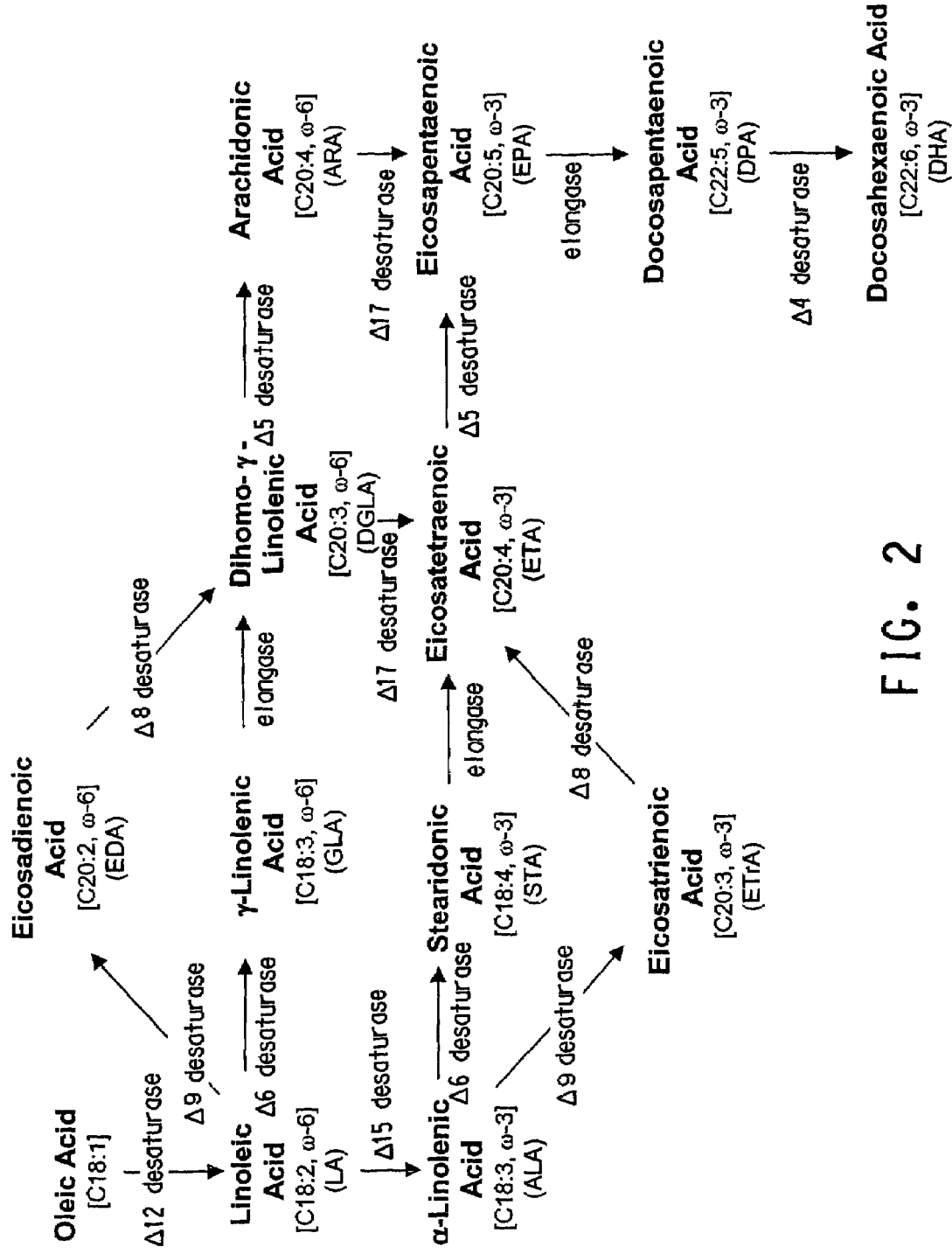
FIG. 2 illustrates the ω-3 and ω-6 fatty acid biosynthetic pathways.
Figure 3A:
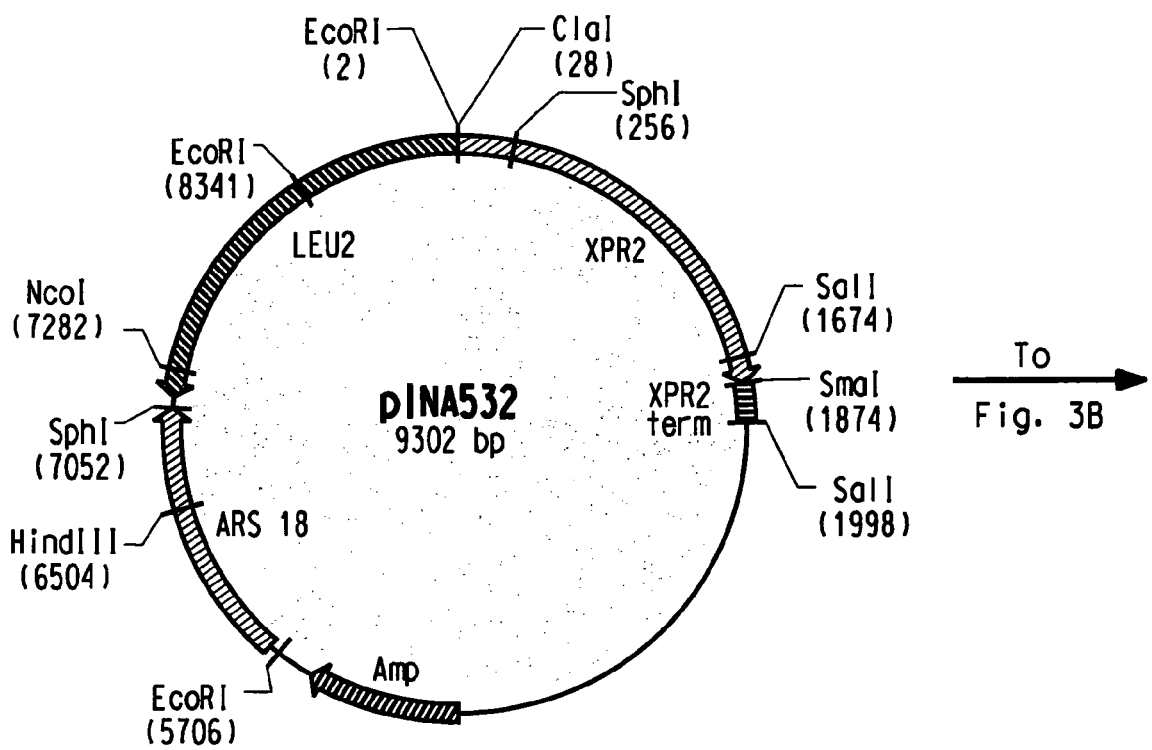
FIG. 3 illustrates the construction of the plasmid vector pY5 for gene expression in *Yarrowia lipolytica*.
Figure 3A:
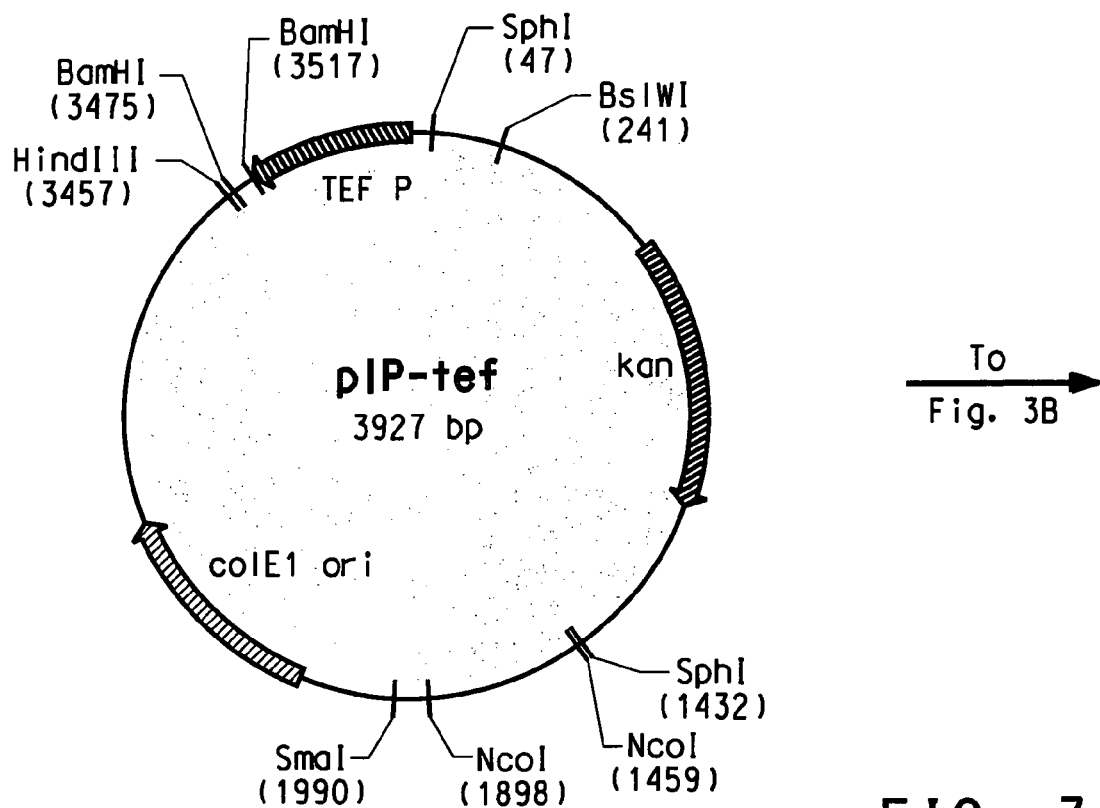
Figure 3B:
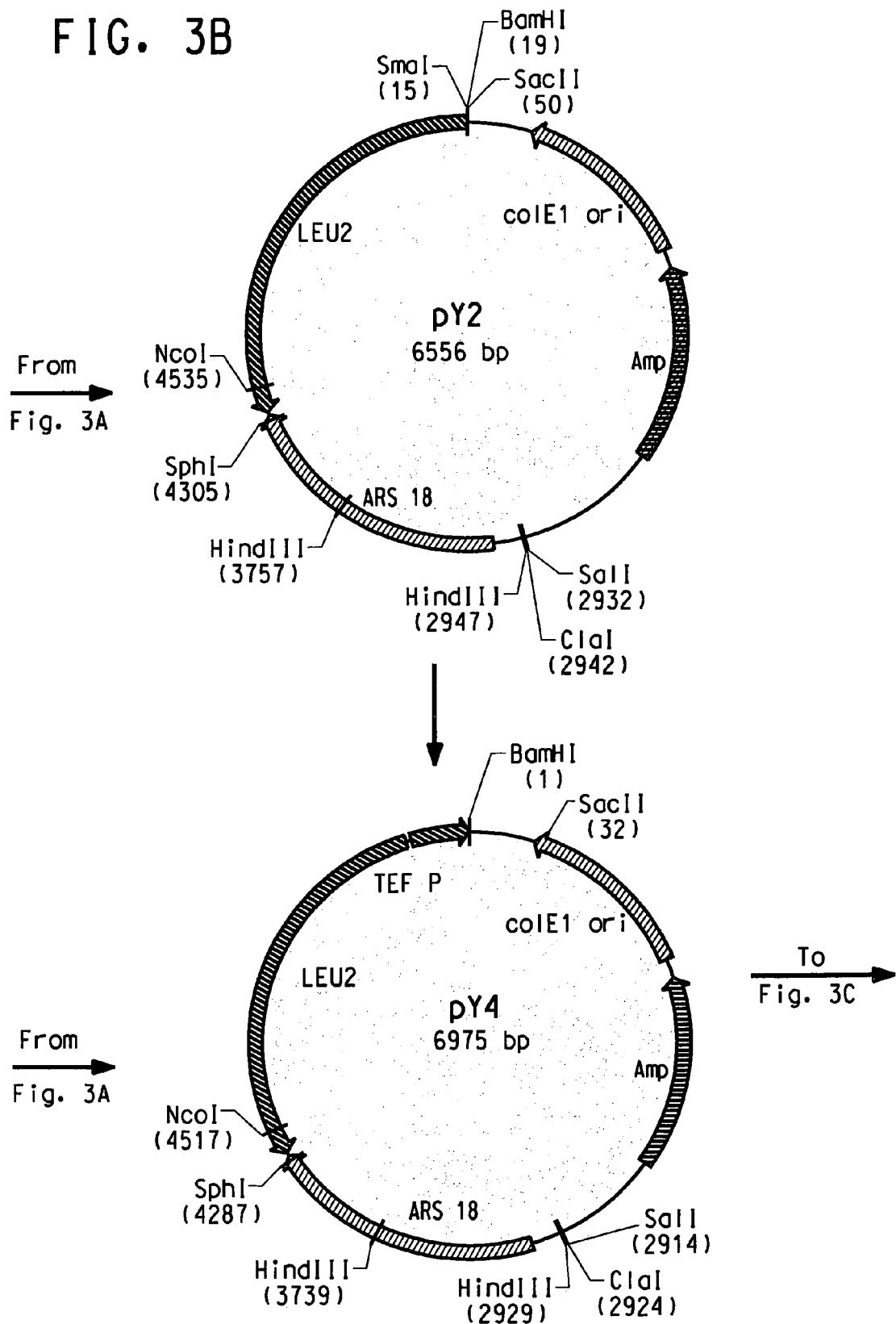
Figures 3B, 3C:
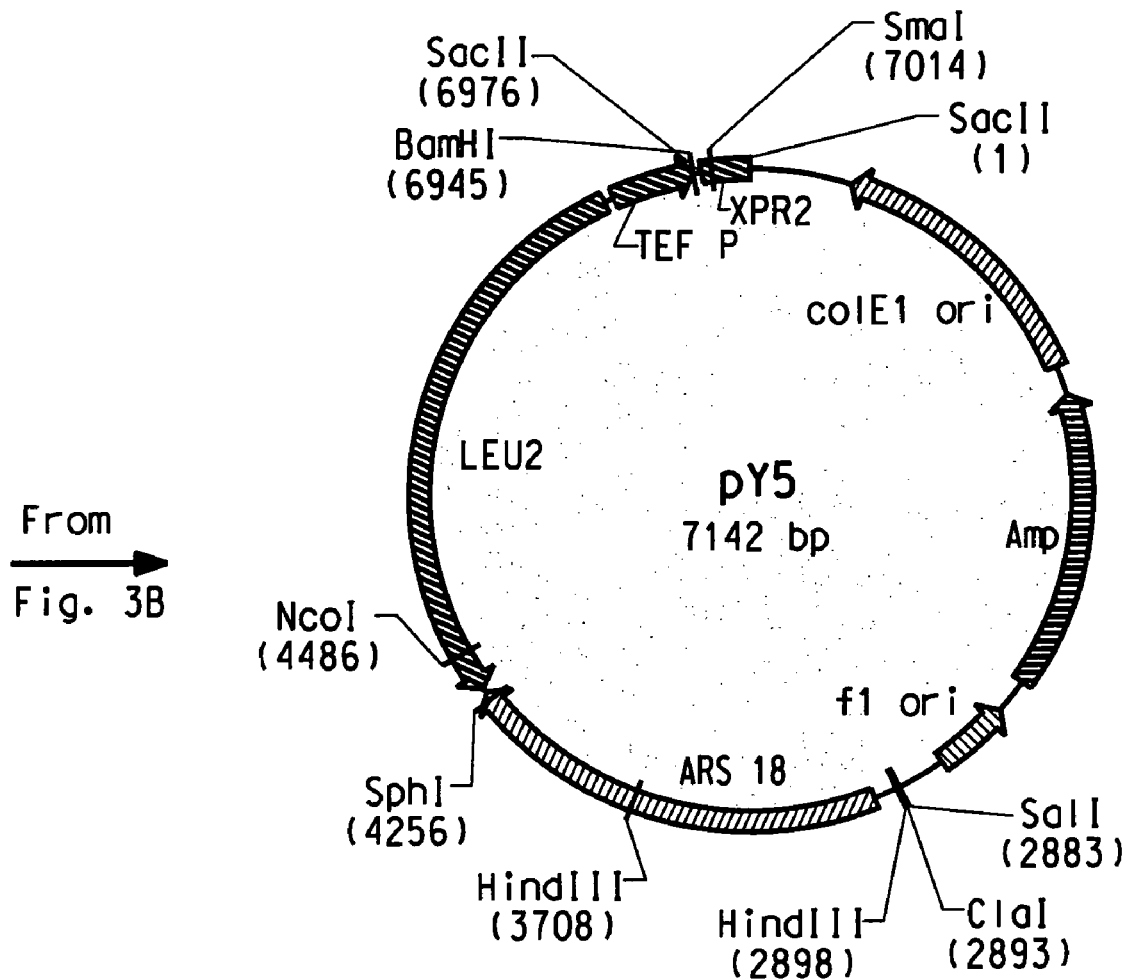

The term "ω-3/ω-6 fatty acid biosynthetic pathway" refers to a set of genes which, when expressed under the appropriate conditions encode enzymes that catalyze the production of either or both ω-3 and ω-6 fatty acids. Typically the genes involved in the ω-3/ω-6 fatty acid biosynthetic pathway encode some or all of the following enzymes: Δ12 desaturase, Δ6 desaturase, elongase, Δ5 desaturase, Δ17 desaturase, Δ15 desaturase, Δ9 desaturase, Δ8 desaturase and Δ4 desaturase. A representative pathway is illustrated in FIG. 2, providing for the conversion of oleic acid through various intermediates to DHA, which demonstrates how both ω-3 and ω-6 fatty acids may be produced from a common source. The pathway is naturally divided into two portions where one portion will generate ω-3 fatty acids and the other portion, only ω-6 fatty acids. That portion that only generates ω-3 fatty acids will be referred to herein as the ω-3 fatty acid biosynthetic pathway, whereas that portion that generates only ω-6 fatty acids will be referred to herein as the ω-6 fatty acid biosynthetic pathway.

The term "functional" as used herein in context with the ω-3/ω-6 fatty acid biosynthetic pathway means that some (or all of) the genes in the pathway express active enzymes. It should be understood that "ωc-3/ω-6 fatty acid biosynthetic pathway" or "functional ω-3/ω-6 fatty acid biosynthetic pathway" does not imply that all the genes listed in the above paragraph are required, as a number of fatty acid products will only require the expression of a subset of the genes of this pathway.

The term "desaturase" refers to a polypeptide that can desaturate, i.e., introduce a double bond, in one or more fatty acids to produce a mono- or polyunsaturated fatty acid. Despite use of the omega-reference system throughout the specification in reference to specific fatty acids, it is more convenient to indicate the activity of a desaturase by counting from the carboxyl end of the substrate using the delta-system. Of particular interest herein are Δ12 desaturases that desaturate a fatty acid between the $12^{th}$ and $13^{th}$ carbon atoms numbered from the carboxyl-terminal end of the molecule and that catalyze the conversion of oleic acid to LA. Other desaturases relevant to the present disclosure include: Δ15 desaturases that catalyze the conversion of LA to ALA; Δ17 desaturases that catalyze the conversion of DGLA to ETA and/or ARA to EPA; Δ6 desaturases that catalyze the conversion of LA to GLA and/or ALA to STA; Δ5 desaturases that catalyze the conversion of DGLA to ARA and/or ETA to EPA; Δ4 desaturases that catalyze the conversion of DPA to DHA; Δ8 desaturases that catalyze the conversion of EDA to DGLA and/or ETrA to ETA; and Δ9 desaturases that catalyze the conversion of palmitate to palmitoleic acid (16:1) and/or stearate to oleic acid (18:1). In the art, Δ15 and Δ17 desaturases are also occassionally referred to as "omega-3 desaturases", "w-3 desaturases", and/or "ω-3 desaturases". Some desaturases have activities on two or more substrates (e.g., the substrates of the *Saprolegnia diclina* Δ17 desaturase include ARA and DGLA, while those of the *Caenorhabditis elegans* ω-3 desaturase include LA and GLA).

The term "proteins having homology to the *Yarrowia lipolytica* Δ12 desaturase" refers to the proteins identified herein as SEQ ID NOs:2, 4, 6, 8, 10, 12, 14, 16, 18, 20, 21 and 22, and that have homology to the *Y. lipolytica* desaturase identified herein as SEQ ID NO:52 (characterized in co-pending U.S. patent application Ser. No. 10/840,325, herein incorporated by reference in its entirety). Phylogenetic analysis determined that these proteins (i.e., SEQ ID NOs:2, 4, 6, 8, 10, 12, 14, 16, 18, 20, 21 and 22) clustered into two distinct sub-families, referred to herein as "Sub-family 1" and "Sub-family 2". Specifically, the Sub-family 1 proteins appear to encode Δ15 desaturases (i.e., SEQ ID NOs:2, 6, 10, 14 and 18; see co-pending U.S. Provisional Application 60/519,191, herein incorporated by reference in its entirety). In contrast, the Sub-family 2 proteins encode proteins with Δ12 desaturase activity (i.e., SEQ ID NOs:4, 8, 12, 16, 20, 21 and 22) as characterized herein.

The terms "conversion efficiency" and "percent substrate conversion" refer to the efficiency by which a particular enzyme (e.g., a desaturase or elongase) can convert substrate to product. The conversion efficiency is measured according to the following formula: ([product]/[substrate+product])*100, where 'product' includes the immediate product and all products in the pathway derived from it. In the present Application, it is desirable to identify those Δ12 desaturases characterized by a high percent substrate conversion when expressed in oleaginous yeast hosts; thus, for example, a conversion efficiency to LA of at least about 70% is preferred, while a conversion efficiency to LA of at least about 80% is particularly suitable, and a conversion efficiency to LA of at least about 85% is most preferred.

The term "elongase" refers to a polypeptide that can elongate a fatty acid carbon chain to produce an acid that is 2 carbons longer than the fatty acid substrate that the elongase acts upon. This process of elongation occurs in a multi-step mechanism in association with fatty acid synthase, whereby CoA is the acyl carrier (Lassner et al., *The Plant Cell* 8:281-292 (1996)). Briefly, malonyl-CoA is condensed with a long-chain acyl-CoA to yield $CO_2$ and a β-ketoacyl-CoA (where the acyl moiety has been elongated by two carbon atoms). Subsequent reactions include reduction to β-hydroxyacyl-CoA, dehydration to an enoyl-CoA, and a second reduction to yield the elongated acyl-CoA. Examples of reactions catalyzed by elongases are the conversion of GLA to DGLA, STA to ETA, and EPA to DPA. Accordingly, elongases can have different specificities. For example, a $C_{16/18}$ elongase will prefer a $C_{16}$ substrate, a $C_{18/20}$ elongase will prefer a $C_{18}$ substrate and a $C_{20/22}$ elongase will prefer a $C_{20}$ substrate. In like manner, a Δ9 elongase is able to catalyze the conversion of LA and ALA to EDA and ETrA, respectively.

The term "oleaginous" refers to those organisms that tend to store their energy source in the form of lipid (Weete, In: Fungal Lipid Biochemistry, $2^{nd}$ ed., Plenum, 1980). These include oilseed plants (e.g., soybean, corn, safflower, sunflower, canola, rapeseed, flax, maize and primrose) and microorganisms (e.g., *Thraustochytrium* sp., *Schizochytrium* sp., *Mortierella* sp. and certain oleaginous yeast).

The term "oleaginous yeast" refers to those microorganisms classified as yeasts that can make oil. Generally, the cellular oil or triacylglycerol content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419-25 (1991)). It is not uncommon for oleaginous microorganisms to accumulate in excess of about 25% of their dry cell weight as oil. Examples of oleaginous yeast include, but are no means limited to, the following genera: *Yarrowia*, *Candida*, *Rhodotorula*, *Rhodosporidium*, *Cryptococcus*, *Trichosporon* and *Lipomyces*.

The term "fermentable carbon substrate" means a carbon source that a microorganism will metabolize to derive energy. Typical carbon substrates of the invention include, but are not limited to: monosaccharides, oligosaccharides, polysaccharides, alkanes, fatty acids, esters of fatty acids, monoglycerides, carbon dioxide, methanol, formaldehyde, formate and carbon-containing amines.

The term "codon optimized" as it refers to genes or coding regions of nucleic acid fragments for transformation of various hosts, refers to the alteration of codons in the gene or coding regions of the nucleic acid molecules to reflect the typical codon usage of the host organism without altering the polypeptide for which the DNA codes.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, $2^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular fungal proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing, as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: N.J. (1994); 4.) *Sequence*

*Analysis in Molecular Biology* (von Heinje, G., Ed.) Academic (1987); and 5.) *Sequence Analysis Primer* (Gribskov, M. and Devereux, J., Eds.) Stockton: N.Y. (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp, *CABIOS.* 5:151-153 (1989)) with default parameters (GAP PENALTY=10, GAP LENGTH PENALTY=10), unless otherwise specified. Default parameters for pairwise alignments using the Clustal method are: KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "homology" refers to the relationship among sequences whereby there is some extent of likeness, typically due to descent from a common ancestral sequence. Homologous sequences can share homology based on genic, structural, functional and/or behavioral properties. The term "ortholog" or "orthologous sequences" refers herein to a relationship where sequence divergence follows speciation (i.e., homologous sequences in different species arose from a common ancestral gene during speciation). In contrast, the term "paralogous" refers to homologous sequences within a single species that arose by gene duplication. One skilled in the art will be familiar with techniques required to identify homologous, orthologous and paralogous sequences.

"Codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Chemically synthesized", as related to a sequence of DNA, means that the component nucleotides were assembled in vitro. Manual chemical synthesis of DNA may be accomplished using well-established procedures; or automated chemical synthesis can be performed using one of a number of commercially available machines. "Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes introduced into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The terms "3' non-coding sequences" and "transcription terminator" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment(s) of the invention. Expression may also refer to translation of mRNA into a polypeptide.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be (but are not limited to) intracellular localization signals.

"Transformation" refers to the transfer of a nucleic acid fragment into a host organism, resulting in genetically stable inheritance. The nucleic acid fragment may be a plasmid that replicates autonomously, for example; or, it may integrate into the genome of the host organism. Host organisms containing the transformed nucleic acid fragments are referred to as "transgenic" or "recombinant" or "transformed" organisms.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing e.g., a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "homologous recombination" refers to the exchange of DNA fragments between two DNA molecules (during cross over). The fragments that are exchanged are flanked by sites of identical nucleotide sequences between the two DNA molecules (i.e., "regions of homology"). The term "regions of homology" refer to stretches of nucleotide sequence on nucleic acid fragments that participate in homologous recombination that have homology to each other. Effective homologous recombination will generally take place where these regions of homology are at least about 10 bp in length where at least about 50 bp in length is preferred. Typically fragments that are intended for recombination contain at least two regions of homology where targeted gene disruption or replacement is desired.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992,111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used herein are well known in the art and are described by Sambrook, J., Fritsch, E. F. and Maniatis, T., *Molecular Cloning: A Laboratory Manual,* 2nd ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions,* Cold Spring Harbor Laboratory: Cold Spring Harbor, N.Y. (1984); and by Ausubel, F. M. et al., *Current Protocols in Molecular Biology,* published by Greene Publishing Assoc. and Wiley-Interscience (1987).

Microbial Biosynthesis of Fatty Acids

Figure 1:
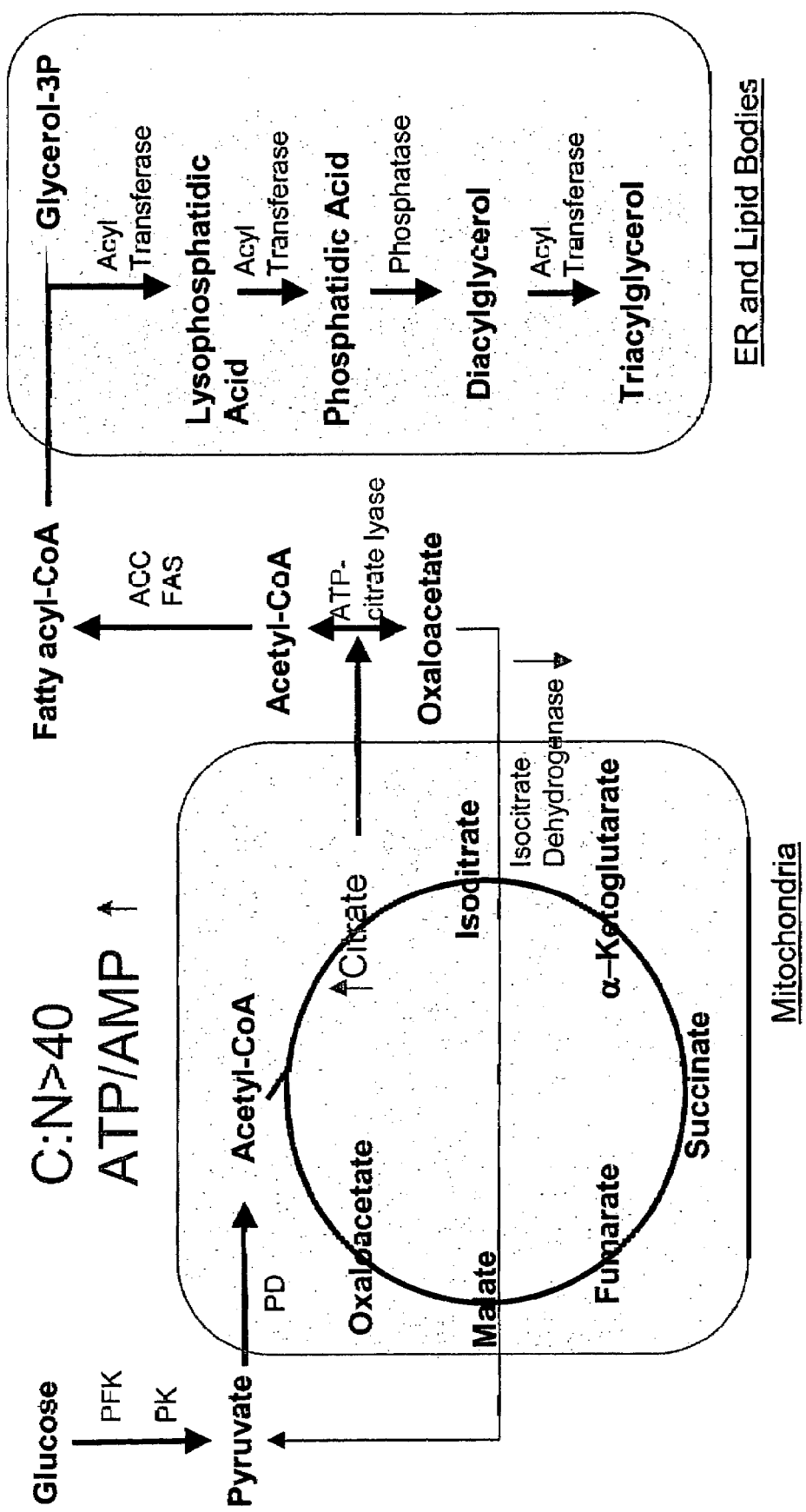
FIG. 1 shows a schematic illustration of the biochemical mechanism for lipid accumulation in oleaginous yeast.

In general, lipid accumulation in oleaginous microorganisms is triggered in response to the overall carbon to nitrogen ratio present in the growth medium (FIG. 1). When cells have exhausted available nitrogen supplies (e.g., when the carbon to nitrogen ratio is greater than about 40), the depletion of cellular adenosine monophosphate (AMP) leads to the cessation of AMP-dependent isocitrate dehydrogenase activity in the mitochondria and the accumulation of citrate, transport of citrate into the cytosol, and subsequent cleavage of the citrate by ATP-citrate lyase to yield acetyl-CoA. Acetyl-CoA is the principle building block for de novo biosynthesis of fatty acids. Although any compound that can effectively be metabolized to produce acetyl-CoA can serve as a precursor of fatty acids, glucose is the primary source of carbon in this type of reaction (FIG. 1). Glucose is converted to pyruvate via glycolysis, and pyruvate is then transported into the mitochondria where it can be converted to acetyl-CoA by pyruvate dehydrogenase ("PD"). Since acetyl-CoA can not be transported directly across the mitochondrial membrane into the cytoplasm, the two carbons from acetyl-CoA condense with oxaloacetate to yield citrate (catalyzed by citrate synthase). Citrate is transported directly into the cytoplasm, where it is cleaved by ATP-citrate lyase to regenerate acetyl-CoA and oxaloacetate. The oxaloacetate reenters the tricarboxylic acid cycle, via conversion to malate.

The synthesis of malonyl-CoA is the first committed step of fatty acid biosynthesis, which takes place in the cytoplasm. Malonyl-CoA is produced via carboxylation of acetyl-CoA by acetyl-CoA carboxylase ("ACC"). Fatty acid synthesis is catalyzed by a multi-enzyme fatty acid synthase complex ("FAS") and occurs by the condensation of eight two-carbon fragments (acetyl groups from acetyl-CoA) to form a 16-carbon saturated fatty acid, palmitate. More specifically, FAS catalyzes a series of 7 reactions, which involve the following (Smith, S. *FASEB J.*, 8(15):1248-59 (1994)):

1. Acetyl-CoA and malonyl-CoA are transferred to the acyl carrier protein (ACP) of FAS. The acetyl group is then transferred to the malonyl group, forming β-ketobutyryl-ACP and releasing $CO_2$.
2. The β-ketobutyryl-ACP undergoes reduction (via β-ketoacyl reductase) and dehydration (via β-hydroxyacyl dehydratase) to form a trans-monounsaturated fatty acyl group.
3. The double bond is reduced by NADPH, yielding a saturated fatty-acyl group two carbons longer than the initial one. The butyryl-group's ability to condense with a new malonyl group and repeat the elongation process is then regenerated.
4. When the fatty acyl group becomes 16 carbons long, a thioesterase activity hydrolyses it, releasing free palmitate.

Palmitate (16:0) is the precursor of longer chain saturated and unsaturated fatty acids (e.g., stearic (18:0), palmitoleic (16:1) and oleic (18:1) acids) through the action of elongases and desaturases present in the endoplasmic reticulum membrane. Palmitate and stearate (as CoA and/or ACP esters) are converted to their unsaturated derivatives, palmitoleic (16:1) and oleic (18:1) acids, respectively, by the action of a Δ9 desaturase.

Triacylglycerols (the primary storage unit for fatty acids) are formed by the esterification of two molecules of acyl-CoA to glycerol-3-phosphate to yield 1,2-diacylglycerol phosphate (commonly identified as phosphatidic acid) (FIG. 1). The phosphate is then removed, by phosphatidic acid phosphatase, to yield 1,2-diacylglycerol. Triacylglycerol is formed upon the addition of a third fatty acid, for example, by the action of a diacylglycerol-acyl transferase.

Biosynthesis of Omega Fatty Acids

Simplistically, the metabolic process that converts LA to GLA, DGLA and ARA (the ω-6 pathway) and ALA to STA, ETA, EPA, DPA and DHA (the ω-3 pathway) involves elongation of the carbon chain through the addition of two-carbon units and desaturation of the molecule through the addition of double bonds (FIG. 2). This requires a series of special desaturation and elongation enzymes present in the endoplasmic reticulum membrane.

ω-6 Fatty Acids

Oleic acid is converted to LA (18:2), the first of the ω-6 fatty acids, by the action of a Δ12 desaturase. Subsequent ω-6 fatty acids are produced as follows: 1.) LA is converted to GLA by the activity of a Δ6 desaturase; 2.) GLA is converted to DGLA by the action of an elongase; and 3.) DGLA is converted to ARA by the action of a Δ5 desaturase.

ω-3 Fatty Acids

Linoleic acid (LA) is converted to ALA, the first of the ω-3 fatty acids, by the action of a Δ15 desaturase. Subsequent ω-3 fatty acids are produced in a series of steps similar to that for the ω-6 fatty acids. Specifically: 1.) ALA is converted to STA by the activity of a Δ6 desaturase; 2.) STA is converted to ETA by the activity of an elongase; and 3.) ETA is converted to EPA by the activity of a Δ5 desaturase. Alternatively, ETA and EPA can be produced from DGLA and ARA, respectively, by the activity of a Δ17 desaturase. EPA can be further converted to DHA by the activity of an elongase and a Δ4 desaturase.

In alternate embodiments, a Δ9 elongase is able to catalyze the conversion of LA and ALA to EDA and ETrA, respectively. A Δ8 desaturase then converts these products to DGLA and ETA, respectively.

Genes Involved in Omega Fatty Acid Production

Many microorganisms, including algae, bacteria, molds and yeast, can synthesize PUFAs and omega fatty acids in the ordinary course of cellular metabolism. Particularly well-studied are fungi including *Schizochytrium aggregatm*, species of the genus *Thraustochytrium* and *Morteriella alpina*. Additionally, many dinoflagellates (Dinophyceaae) naturally produce high concentrations of PUFAs. As such, a variety of genes involved in oil production have been identified through genetic means and the DNA sequences of some of these genes are publicly available (non-limiting examples are shown below in Table 3):

TABLE 3

Some Publicly Available Genes involved in PUFA Production

| Genbank Accession No. | Description |
| --- | --- |
| AY131238 | *Argania spinosa* Δ6 desaturase |
| Y055118 | *Echium pitardii* var. *pitardii* Δ6 desaturase |
| AY055117 | *Echium gentianoides* Δ6 desaturase |
| AF296076 | *Mucor rouxii* Δ6 desaturase |
| AF007561 | *Borago officinalis* Δ6 desaturase |
| L11421 | *Synechocystis* sp. Δ6 desaturase |
| NM_031344 | *Rattus norvegicus* Δ6 fatty acid desaturase |
| AF465283, AF465281, AF110510 | *Mortierella alpina* Δ6 fatty acid desaturase |
| AF465282 | *Mortierella isabellina* Δ6 fatty acid desaturase |
| AF419296 | *Pythium irregulare* Δ6 fatty acid desaturase |
| AB052086 | *Mucor circinelloides* D6d mRNA for Δ6 fatty acid desaturase |
| AJ250735 | *Ceratodon purpureus* mRNA for Δ6 fatty acid desaturase |
| AF126799 | *Homo sapiens* Δ6 fatty acid desaturase |
| AF126798 | *Mus musculus* Δ6 fatty acid desaturase |
| AF199596, AF226273 | *Homo sapiens* Δ5 desaturase |
| AF320509 | *Rattus norvegicus* liver Δ5 desaturase |
| AB072976 | *Mus musculus* D5D mRNA for Δ5 desaturase |
| AF489588 | *Thraustochytrium* sp. ATCC21685 Δ5 fatty acid desaturase |
| AJ510244 | *Phytophthora megasperma* mRNA for Δ5 fatty acid desaturase |
| AF419297 | *Pythium irregulare* Δ5 fatty acid desaturase |
| AF07879 | *Caenorhabditis elegans* Δ5 fatty acid desaturase |
| AF067654 | *Mortierella alpina* Δ5 fatty acid desaturase |
| AB022097 | *Dictyostelium discoideum* mRNA for Δ5 fatty acid desaturase |
| AF489589.1 | *Thraustochytrium* sp. ATCC21685 Δ4 fatty acid desaturase |
| AX464731 | *Mortierella alpina* elongase gene (also WO 00/12720) |
| AAG36933 | *Emericella nidulans* oleate Δ12 desaturase |
| AF110509, AB020033 | *Mortierella alpina* Δ12 fatty acid desaturase mRNA |
| AAL13300 | *Mortierella alpina* Δ12 fatty acid desaturase |

TABLE 3-continued

Some Publicly Available Genes involved in PUFA Production

| Genbank Accession No. | Description |
|---|---|
| AF417244 | *Mortierella alpina* ATCC 16266 Δ12 fatty acid desaturase gene |
| AF161219 | *Mucor rouxii* Δ12 desaturase mRNA |
| X86736 | *Spiruline platensis* Δ12 desaturase |
| AF240777 | *Caenorhabditis elegans* Δ12 desaturase |
| AB007640 | *Chlamydomonas reinhardtii* Δ12 desaturase |
| AB075526 | *Chlorella vulgaris* Δ12 desaturase |
| AP002063 | *Arabidopsis thaliana* microsomal Δ12 desaturase |
| NP_441622, BAA18302, BAA02924 | *Synechocystis* sp. PCC 6803 Δ15 desaturase |
| AAL36934 | *Perilla frutescens* Δ15 desaturase |
| AF338466 | *Acheta domesticus* Δ9 desaturase 3 mRNA |
| AF438199 | *Picea glauca* desaturase Δ9 (Des9) mRNA |
| E11368 | *Anabaena* Δ9 desaturase |
| E11367 | *Synechocystis* Δ9 desaturase |
| D83185 | *Pichia angusta* DNA for Δ9 fatty acid desaturase |
| U90417 | *Synechococcus vulcanus* Δ9 acyl-lipid fatty acid desaturase (desC) gene |
| AF085500 | *Mortierella alpina* Δ9 desaturase mRNA |
| AY504633 | *Emericella nidulans* Δ9 stearic acid desaturase (sdeB) gene |
| NM_069854 | *Caenorhabditis elegans* essential fatty acid desaturase, stearoyl-CoA desaturase (39.1 kD) (fat-6) complete mRNA |
| AF230693 | *Brassica oleracea* cultivar Rapid Cycling stearoyl-ACP desaturase (Δ9-BO-1) gene, exon sequence |
| AX464731 | *Mortierella alpina* elongase gene (also WO 02/08401) |
| NM_119617 | *Arabidopsis thaliana* fatty acid elongase 1 (FAE1) (At4g34520) mRNA |
| NM_134255 | *Mus musculus* ELOVL family member 5, elongation of long chain fatty acids (yeast) (Elovl5), mRNA |
| NM_134383 | *Rattus norvegicus* fatty acid elongase 2 (rELO2), mRNA |
| NM_134382 | *Rattus norvegicus* fatty acid elongase 1 (rELO1), mRNA |
| NM_068396, NM_068392, NM_070713, NM_068746, NM_064685 | *Caenorhabditis elegans* fatty acid ELOngation (elo-6), (elo-5), (elo-2), (elo-3), and (elo-9) mRNA |

Additionally, the patent literature provides many additional DNA sequences of genes (and/or details concerning several of the genes above and their methods of isolation) involved in oil production. See, for example: U.S. Pat. No. 5,968,809 (Δ6 desaturases); U.S. Pat. Nos. 5,972,664 and 6,075,183 (Δ5 desaturases); WO 91/13972 and U.S. Pat. No. 5,057,419 (Δ9 desaturases); U.S. 2003/0196217 A1 (Δ17 desaturases); WO 02/090493 (Δ4 desaturases); WO 93/11245 and WO 03/099216 (Δ15 desaturases); WO 00/12720 and U.S. 2002/0139974A1 (elongases). Each of these patents and applications are herein incorporated by reference in their entirety.

Of particular interest herein are Δ12 desaturases, and more specifically, Δ12 desaturases that are suitable for heterologous expression in oleaginous yeast (e.g., *Yarrowia lipolytica*). Sequences of some Δ12 desaturases (i.e., *Glycine max, Brassica napus, Arabidopsis thaliana, Ricinus communis, Zea mays; Neurospora crassa, Botrytis cinerea*) are disclosed in WO 94/11516 and WO 03/099216.

Additionally, the native *Yarrowia lipolytica* Δ12 fatty acid desaturase was recently isolated and characterized (see copending U.S. patent application Ser. No. 10/840,325, incorporated entirely by reference; see also Examples 2 and 3 herein and SEQ ID NOs:51 and 52). Briefly, a partial putative Δ12 desaturase DNA fragment from *Yarrowia lipolytica* was cloned by PCR using degenerate PCR primers. Targeted disruption of the endogenous *Yarrowia lipolytica* Δ12 desaturase gene using the fragment produced increased levels of 18:1 and no detectable 18:2 in the disrupted strain, thereby confirming that the native Δ12 desaturase activity was eliminated. Subsequently, genomic DNA sequences flanking the integrated plasmid were isolated using plasmid rescue and a full-length *Yarrowia lipolytica* Δ12 desaturase gene was assembled (SEQ ID NO:51). The sequence included an open reading frame of 1257 bases (nucleotides +283 to +1539 of SEQ ID NO:51), while the deduced encoded amino acid sequence was 419 residues in length (SEQ ID NO:52). Overexpression of this Δ12 desaturase was suitable to increase the percent substrate conversion of oleic acid to LA (calculated as ([18:2]/[18:1+18:2])*100), such that it increased from 59% in the wildtype cells to 74% in the transformed host cells. Despite the increased availability of LA within these host cells, however, it was desirable to obtain an even larger substrate pool suitable to enable high-level production of a variety of (0-3 and/or ω-6 PUFAs within the *Y. lipolytica* transformant cells. Thus, expression of a heterologous protein having high-level Δ12 desaturase activity was therefore advantageous in the pathway engineering of the organism.

Many factors affect the choice of a specific polypeptide having Δ12 desaturase activity that is to be expressed in a host cell for production of PUFAs (optionally in combination with other desaturases and elongases). Depending upon the host cell, the availability of substrate, and the desired end product(s), several polypeptides are of interest; however, considerations for choosing a specific polypeptide having desaturase activity include the substrate specificity of the polypeptide, whether the polypeptide or a component thereof is a rate-limiting enzyme, whether the desaturase is essential for synthesis of a desired PUFA, and/or co-factors required by the polypeptide. The expressed polypeptide preferably has parameters compatible with the biochemical environment of its location in the host cell. For example, the polypeptide may have to compete for substrate with other enzymes in the host cell. Analyses of the KM and specific activity of the polypeptide are therefore considered in determining the suitability of a given polypeptide for modifying PUFA production in a given host cell. The polypeptide used in a particular host cell is one which can function under the biochemical conditions present in the intended host cell but otherwise can be any polypeptide having Δ12 desaturase activity capable of modifying the desired fatty acids (i.e., oleic acid). Thus, the sequences may be derived from any source, e.g., isolated from a natural source (from bacteria, algae, fungi, plants, animals, etc.), produced via a semi-synthetic route or synthesized de novo.

For the purposes of the present invention herein, however, it is most desirable for the polypeptide having Δ12 desaturase activity to have a conversion efficiency of at least about 70% when expressed in the desired host cell, wherein a conversion efficiency of at least about 80% is particularly suitable, and a conversion efficiency of at least about 85% is most preferred.

Identification of Novel Fungal Δ12 Desaturases

A novel Δ12 desaturase from *Fusarium moniliforme* was identified herein, by sequence comparison using the *Yarrowia lipolytica* Δ12 desaturase protein sequence (SEQ ID NO:52) as a query sequence. Specifically, this *Yarrowia* query sequence was used to search putative encoded protein sequences of a proprietary DuPont expressed sequence tag (EST) library of *Fusarium moniliforme* strain M-8114 (E.I. du Pont de Nemours and Co., Inc., Wilmington, Del.). This resulted in the identification of two homologous sequences, Fm1 (SEQ ID NO:2) and Fm2 (SEQ ID NO:4), encoded by nucleotide sequences SEQ ID NOs:1 and 3, respectively.

The *Yarrowia* Δ12 desaturase sequence was also used as a query against public databases of several filamentous fungi; specifically, homologous protein sequences were identified in *Aspergillus nidulans* (SEQ ID NOs:6 and 8), *Magnaporthe grisea* (SEQ ID NOs:10 and 12), *Neurospora crassa* (SEQ ID NOs:14 and 16), *Fusarium graminearium* (SEQ ID NOs:18 and 20), *Aspergillus fumigatus* (SEQ ID NO:21) and *Aspergillus flavus* (SEQ ID NO:22). Subsequent phylogenetic and homology analysis, based on comparison of these sequences (i.e., SEQ ID NOs:2, 4, 6, 8,10, 12, 14, 16,18, 20, 21 and 22) using the method of Clustal W (slow, accurate, Gonnet option; Thompson et al. *Nucleic Acids Res.* 22:46734680 (1994)), revealed two distinct "sub-families" of proteins having homology with the *Yarrowia* Δ12 desaturase. Specifically, all proteins of "sub-family 1" (SEQ ID NOs:2, 6,10, 14 and 18) were at least 46.2% identical to each other and were less than 39.6% identical to the proteins of "sub-family 2" (SEQ ID NOs:4, 8, 12,16, 20, 21 and 22) (FIGS. 4 and 5; Clustal method of alignment (supra)). The proteins of sub-family 2 were at least 56.3% identical to each other (see Example 4).

Since *Yarrowia* is only able to synthesize 18:2 (but not 18:3) while most of the filamentous fungi described above can make both 18:2 and ALA, and since *Yarrowia* has a single Δ12 desaturase while most of the filamentous fungi had two homologs to the *Yarrowia* Δ12 desaturase, the Applicants postulated that one of the sub-families of desaturases in these organisms represented Δ12 desaturases and the other represented Δ15 desaturases. This hypothesis was tested by determining the activity of a representative protein within each of the two sub-families using expression analysis. Specifically, Fm1 and Mg1 were expressed in *Yarrowia lipolytica* and found to encode Δ15 desaturases (see co-pending U.S. Provisional Application 60/519,191); similarly, the Dec. 4, 2003 publication of WO 03/099216 suggests that the sequences identified herein as the sub-family 1 Neurospora crassa and Aspergillus nidulans sequences had Δ15 desaturase activity. In contrast, Fm2 was expressed in *Y. lipolytica* as described herein and was characterized as a Δ12 desaturase. The Δ12 desaturase activity of the sub-family 2 Neurospora crassa sequence was similarly confirmed in WO 03/099216.

The *Fusarium moniliforme* Δ12 desaturase deduced amino acid sequence (SEQ ID NO:4) was compared to public database sequences using a Clustal method of alignment (Thompson et al., *Nucleic Acids Res.* 22:46734680 (1994)). Thus, the *Fusarium moniliforme* Δ12 desaturase amino acid sequence was most similar based on percent identity to the *Fusarium graminearium* Δ12 desaturase provided herein as SEQ ID NO:20 (95% identical over a length of 477 amino acids). More preferred amino acid fragments are at least about 96% identical to the sequence herein, where those sequences that are 97%-98% identical are particularly suitable and those sequences that are about 99% identical are most preferred.

In like manner, comparison of the *Fusarium moniliforme* Δ12 desaturase nucleotide base sequence to public databases using the Clustal method of alignment reveals that the most similar known nucleic acid sequence (Contig 1.233 in the *F. graminearium* genome project; SEQ ID NO:19 herein) is about 89.2% identical to the nucleic acid sequence of the *Fusarium moniliforme* Δ12 desaturase reported herein (SEQ ID NO:3). Preferred Δ12 desaturase encoding nucleic acid sequences corresponding to the instant ORF are those encoding active proteins and which are at least about 89%-90% identical to the nucleic acid sequence encoding the *Fusarium moniliforme* Δ12 desaturase reported herein, where those sequences that are 91%-95% identical are particularly suitable and those sequences that are greater than 95% identical are most preferred.

Identification and Isolation of Homologs

The Δ12 desaturase nucleic acid fragment of the instant invention may be used to identify and isolate genes encoding homologous proteins from the same or other bacterial, algal, fungal or plant species.

Identification Techniques

For example, a substantial portion of the *Fusarium moniliforme* Δ12 desaturase amino acid or nucleotide sequence described herein can be used to putatively identify related polypeptides or genes, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403-410 (1993)) and ClustalW (Megalign program of DNASTAR software). As described above, use of the *Yarrowia lipolytica* Δ12 desaturase (SEQ ID NO:52) permitted the identification of a suite of fungal desaturases which, upon analysis, clustered as two distinct sub-families of proteins (i.e., sub-family 1 and sub-family 2). Subfamily-2 comprised the *Fusarium moniliforme* Δ12 desaturase described above, as well as the proteins whose coding DNA sequences are found within the following:

Contig 1.15 (scaffold 1) (AAG36933) in the *Aspergillus nidulans* genome project (sponsored by the Center for Genome Research (CGR), Cambridge, Mass.) (SEQ ID NO:8);

Locus MG01985.1 in contig 2.375 in the *Magnaporthe grisea* genome project (sponsored by the CGR and International Rice Blast Genome Consortium) (SEQ ID NO:12);

GenBank Accession No. MBX01000374 (*Neurospora crassa*) (SEQ ID NO:16);

Contig 1.233 in the *Fusarium graminearium* genome project (sponsored by the CGR and the International *Gibberella zeae* Genomics Consortium (IGGR)) (SEQ ID NO:20);

AFA.344248:345586 (reverse) in the *Aspergillus fumigatus* genome project (sponsored by Sanger Institute, collaborators at the University of Manchester and The Institute of Genome Research (TIGR)) (SEQ ID NO:21); and, GenBank Accession No. AY280867 (*Aspergillus flavus*) (SEQ ID NO:22).

Each of the above proteins are hypothesized to encode a Δ12 desaturase. This hypothesis was confirmed for *Neurospora crassa* in WO 03/099216.

Analysis of the above proteins revealed that these proteins have at least 56.3% sequence identity to the *Fusarium moniliforme* Δ12 desaturase (SEQ ID NO:4), according to the Clustal method of alignment (supra) (FIG. 5). Additionally, the Δ12 desaturases of sub-family 2 in the present invention were also compared to other known Δ12 desaturase proteins; however, the Δ12 desaturases of sub-family 2 herein are more homologous to the *Yarrowia lipolytica* Δ12 desaturase (51.6% identity; FIG. 6) than they are to any other known Δ12 desaturase. One skilled in the art would be able to use similar methodology to identify other orthologous proteins that would also cluster within sub-family 2 (identified herein as Δ12 desaturases).

Alternatively, any of the instant desaturase sequences (i.e., SEQ ID NOs:3, 4, 7, 8, 11, 12, 15, 16, 19, 20, 21 and 22) may be employed as hybridization reagents for the identification of homologs. The basic components of a nucleic acid hybridization test include a probe, a sample suspected of containing the gene or gene fragment of interest and a specific hybridization method. Probes of the present invention are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Isolation Methods

The *Fusarium moniliforme* Δ12 desaturase nucleic acid fragment of the instant invention (or any of the Δ12 desaturases identified herein [SEQ ID NOs:7, 8, 11, 12, 15, 16, and 19-22]) may be used to isolate genes encoding homologous proteins from the same or other bacterial, algal, fungal or plant species. Isolation of homologous genes using sequence-dependent protocols is well known in the art.

Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker, et al., *Proc. Natl. Acad. Sci. U.S.A.,* 89:392 (1992)]; and 3.) methods of library construction and screening by complementation.

For example, genes encoding similar proteins or polypeptides to the desaturases described herein could be isolated directly by using all or a portion of the instant nucleic acid fragments as DNA hybridization probes to screen libraries from any desired yeast or fungus using methodology well known to those skilled in the art (wherein those yeast or fungus producing LA [or LA-derivatives] would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in *Human Genetic Diseases*: A Practical Approach, K. E. Davis Ed., (1986) pp 33-50, IRL: Herndon, V A; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Gibco/BRL, Gaithersburg, Md.), specific 3' or 5' cDNA fragments can be isolated (Ohara et al., *PNAS USA* 86:5673 (1989); Loh et al., *Science* 243:217 (1989)).

Availability of the instant nucleotide and deduced amino acid sequences facilitates immunological screening of DNA expression libraries. Synthetic peptides representing portions of the instant amino acid sequence may be synthesized. These peptides can be used to immunize animals to produce polyclonal or monoclonal antibodies with specificity for peptides or proteins comprising the amino acid sequences. These antibodies can be then be used to screen DNA expression libraries to isolate full-length DNA clones of interest (Lerner, R. A. *Adv. Immunol.* 36:1 (1984); Maniatis, supra).

Gene Optimization for Improved Heterologous Expression

A variety of techniques can be utilized to improve expression of a particular Δ12 desaturase of interest in an alternative host. Two such techniques include codon-optimization and mutagenesis of the gene.

Codon Optimization

For some embodiments, it may be desirable to modify a portion of the codons encoding polypeptides having Δ12 desaturase activity, for example, to enhance the expression of the genes encoding those polypeptides in an alternative host (i.e., oleaginous yeast).

In general, host preferred codons can be determined within a particular host species of interest by examining codon usage in proteins (preferably those proteins expressed in the largest amount) and determining which codons are used with highest frequency. Then, the coding sequence for the polypeptide of interest having desaturase activity can be synthesized in whole or in part using the codons preferred in the host species. All (or portions) of the DNA also can be synthesized to remove any destabilizing sequences or regions of secondary structure that would be present in the transcribed mRNA. All (or portions) of the DNA also can be synthesized to alter the base composition to one more preferable in the desired host cell.

In preferred embodiments of the invention, the Δ12 desaturases from e.g., *Fusarium moniliforme, Aspergillus nidulans, Magnaporthe grisea, Neurospora crassa, Fusarium graminearium, Aspergillus fumigatus* and *Aspergillus flavus* could be codon-optimized prior to their expression in a heterologous oleaginous yeast host, such as *Yarrowia lipolytica.*

Mutagenesis

Methods for synthesizing sequences and bringing sequences together are well established in the literature. For example, in vitro mutagenesis and selection, site-directed mutagenesis, error prone PCR (Melnikov et al., *Nucleic Acids Research,* 27(4):1056-1062 (Feb. 15, 20 1999)), "gene shuffling" (U.S. Pat. Nos. 5,605,793; 5,811,238; 5,830,721; and 5,837,458) or other means can be employed to obtain mutations of naturally occurring desaturase genes, such as the Δ12 desaturases described herein. This would permit production of a polypeptide having desaturase activity in vivo with more desirable physical and kinetic parameters for function in the host cell (e.g., a longer half-life or a higher rate of production of a desired PUFA).

If desired, the regions of a desaturase polypeptide important for enzymatic activity can be determined through routine mutagenesis, expression of the resulting mutant polypeptides and determination of their activities. Mutants may include deletions, insertions and point mutations, or combinations thereof. A typical functional analysis begins with deletion mutagenesis to determine the N- and C-terminal limits of the protein necessary for function, and then internal deletions, insertions or point mutants are made to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after the 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites. Internal deletions can similarly be made through a variety of methods including the use of existing restriction sites in the DNA, by use of mutagenic primers via site-directed mutagenesis or mutagenic PCR. Insertions are made through methods such as linker-scanning mutagenesis, site-directed mutagenesis or mutagenic PCR. Point mutations are made through techniques such as site-directed mutagenesis or mutagenic PCR.

Chemical mutagenesis also can be used for identifying regions of a desaturase polypeptide important for activity. A mutated construct is expressed, and the ability of the resulting altered protein to function as a desaturase is assayed. Such structure-function analysis can determine which regions may be deleted, which regions tolerate insertions, and which point mutations allow the mutant protein to function in substantially the same way as the native desaturase. All such mutant proteins and nucleotide sequences encoding them that are derived from the desaturase genes described herein are within the scope of the present invention.

Thus, the present invention comprises the complete sequences of the Δ12 desaturase genes as reported in the accompanying Sequence Listing, the complement of those complete sequences, substantial portions of those sequences, codon-optimized desaturases derived therefrom, and those sequences that are substantially homologous thereto.

Microbial Production Of ω-3 and/or ω-6 Fatty Acids

Microbial production of ω-3 and/or ω-6 fatty acids can have several advantages over purification from natural sources such as fish or plants. For example:

1.) Many microbes are known with greatly simplified oil compositions compared with those of higher organisms, making purification of desired components easier;
2.) Microbial production is not subject to fluctuations caused by external variables, such as weather and food supply;
3.) Microbially produced oil is substantially free of contamination by environmental pollutants;
4.) Microbes can provide PUFAs in particular forms which may have specific uses; and
5.) Microbial oil production can be manipulated by controlling culture conditions, notably by providing particular substrates for microbially expressed enzymes, or by addition of compounds or genetic engineering approaches to suppress undesired biochemical pathways.

In addition to these advantages, production of ω-3 and/or ω-6 fatty acids from recombinant microbes provides the ability to alter the naturally occurring microbial fatty acid profile by providing new biosynthetic pathways in the host or by suppressing undesired pathways, thereby increasing levels of desired PUFAs (or conjugated forms thereof) and decreasing levels of undesired PUFAs (see co-pending U.S. patent application Ser. No. 10/840,579, herein incorporated entirely by reference).

Methods for Production of Various ω-3 and/or ω-6 Fatty Acids

It is expected that introduction of chimeric genes encoding the Δ12 desaturases described herein, under the control of the appropriate promoters will result in increased production of LA in the transformed host organism. As such, the present invention encompasses a method for the direct production of PUFAs comprising exposing a fatty acid substrate (i.e., oleic acid) to the PUFA enzyme(s) described herein (e.g., the *Fusarium moniliforme* Δ12 desaturase), such that the substrate is converted to the desired fatty acid product (i.e., LA). More specifically, it is an object of the present invention to provide a method for the production of LA in an oleaginous yeast, wherein the oleaginous yeast is provided: (a) an isolated nucleic acid fragment encoding a fungal protein having Δ12 desaturase activity that has at least 56.3% identity based on the Clustal method of alignment when compared to a polypeptide having the sequence as set forth in SEQ ID NO:4; and, (b) a source of desaturase substrate consisting of oleic acid; wherein the yeast is grown under conditions such that the chimeric desaturase gene is expressed and the oleic acid is converted to LA, and wherein the LA is optionally recovered. Thus, this method minimally includes the use of the following Δ12 desaturases: SEQ ID NOs:4, 8, 12, 16, 20, 21 and 22, as described herein.

Alternatively, each PUFA gene and its corresponding enzyme product described herein can be used indirectly for the production of ω-3 and/or ω-6 PUFAs. Indirect production of PUFAs occurs wherein the fatty acid substrate is converted indirectly into the desired fatty acid product, via means of an intermediate step(s) or pathway intermediate(s). Thus, it is contemplated that the Δ12 desaturases described herein may be expressed in conjunction with one or more genes that encode other enzymes, such that a series of reactions occur to produce a desired product. In a preferred embodiment, for example, a host organism may be co-transformed with a vector comprising additional genes encoding enzymes of the PUFA biosynthetic pathway to result in higher levels of production of ω-3 and/or ω-6 fatty acids (e.g., GLA, DGLA, ARA, ALA, STA, ETA, EPA, DPA and DHA). Specifically, for example, it may be desirable to over-express any one of the Δ12 desaturases described herein in host cells that are also expressing: 1.) a gene encoding a Δ6 desaturase for the overproduction of GLA; 2.) an expression cassette comprising genes encoding a Δ6 desaturase and a high-affinity elongase for the overproduction of DGLA; 3.) genes encoding a Δ6 desaturase, high-affinity elongase and Δ5 desaturase for the overproduction of ARA; or 4.) genes encoding a Δ6 desaturase, high-affinity elongase, Δ5 desaturase and Δ17 desaturase for the overproduction of EPA. In alternative embodiments, for example, it may be desirable to overexpress the Δ12 desaturase as described herein in cells that are also expressing: 1.) a gene encoding a Δ15 desaturase for the overproduction of ALA; 2.) genes encoding a Δ15 desaturase and Δ6 desaturase for the overproduction of STA; 3.) genes encoding a Δ15 desaturase, Δ6 desaturase and a high-affinity elongase for the overproduction of ETA; or 4.) genes encoding a Δ15 desaturase, Δ6 desaturase, high-affinity elongase and Δ5 desaturase for the overproduction of EPA. As is well known to one skilled in the art, various other combinations of the following enzymatic activities may be useful to express in a host in conjunction with the desaturase(s) herein: a Δ15 desaturase, a Δ4 desaturase, a Δ5 desaturase, a Δ6 desaturase, a Δ17 desaturase, a Δ9 desaturase, a Δ8 desaturase and/or an elongase(s) (see FIG. 2). The particular genes included within a particular expression cassette will depend on the host cell (and its PUFA profile and/or desaturase profile), the availability of substrate, and the desired end product(s).

In alternative embodiments, it may be useful to disrupt a host organism's native Δ12 desaturase, based on the complete sequences described herein, the complement of those complete sequences, substantial portions of those sequences, codon-optimized desaturases derived therefrom and those sequences that are substantially homologous thereto. For example, the targeted disruption of the Δ12 desaturase in a host organism produces a mutant strain that is unable to synthesize LA.

Expression Systems, Cassettes And Vectors

The gene and gene product of the instant sequences described herein may be produced in heterologous microbial host cells, particularly in the cells of oleaginous yeast (e.g., *Yarrowia lipolytica*). Expression in recombinant microbial hosts may be useful for the production of various PUFA pathway intermediates, or for the modulation of PUFA pathways already existing in the host for the synthesis of new products heretofore not possible using the host.

Microbial expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate microorganisms via transformation to provide high-level expression of the encoded enzymes.

Vectors or DNA cassettes useful for the transformation of suitable host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation and a region 3' of the DNA fragment that controls transcriptional termination. It is most preferred when both control regions are derived from genes from the transformed host cell, although it is to be understood that such control regions need not be derived from the genes native to the specific species chosen as a production host.

Initiation control regions or promoters which are useful to drive expression of the instant ORFs in the desired host cell are numerous and familiar to those skilled in the art. Virtually any promoter capable of directing expression of these genes in the selected host cell is suitable for the present invention. Expression in a host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species. The transcriptional initiation regulatory regions can be obtained, for example, from: 1.) genes in the glycolytic pathway, such as alcohol dehydrogenase, glyceraldehyde-3-phosphate-dehydrogenase (see U.S. patent application Ser. No. 10/869,630), phosphoglycerate mutase (see U.S. patent application Ser. No. 10/869,630), fructose-bisphosphate aldolase (see U.S. Patent Application No. 60/519,971), phosphoglucose-isomerase, phosphoglycerate kinase, glycerol-3-phosphate O-acyltransferase (see U.S. Patent Application No. 60/610,060), etc.; or, 2.) regulatable genes such as acid phosphatase, lactase, metallothionein, glucoamylase, the translation elongation factor EF1-α (TEF) protein (U.S. Pat. No. 6,265,185), ribosomal protein S7 (U.S. Pat. No. 6,265,185), etc. Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon ATG have been found to affect expression in yeast cells. If any of the instant Δ12 desaturases are poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest (see, e.g., U.S. patent application Ser. No. 10/840,478 for specific teachings applicable for *Yarrowia lipolytica*).

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, the termination region is derived from a yeast gene, particularly *Saccharomyces, Schizosaccharomyces, Candida, Yarrowia* or *Kluyveromyces*. The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation, and secretion from the host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation in the host organism; 5.) the intrinsic stability of the cloned gene protein within the host cell; and 6.) the codon usage within the cloned gene, such that its frequency approaches the frequency of preferred codon usage of the host cell. Each of these types of modifications are encompassed in the present invention, as means to further optimize expression of the Δ12 desaturases described herein.

Transformation of Microbial Hosts

Once the DNA encoding a polypeptide suitable for expression in an oleaginous yeast has been obtained, it is placed in a plasmid vector capable of autonomous replication in a host cell, or it is directly integrated into the genome of the host cell. Integration of expression cassettes can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a host cell by any standard technique. These techniques include transformation (e.g., lithium acetate transformation [*Methods in Enzymology*, 194:186-187 (1991)]), protoplast fusion, biolistic impact, electroporation, microinjection, or any other method that introduces the gene of interest into the host cell. More specific teachings applicable for oleaginous yeast (i.e., *Yarrowia lipolytica*) include U.S. Pat. Nos. 4,880,741 and 5,071,764 and Chen, D. C. et al. (*Appl Microbiol Biotechnol*. 48(2):232-235-(1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified, or is present on an extrachromosomal element having multiple copy numbers. The transformed host cell can be identified by selection for a marker contained on the introduced construct. Alternatively, a separate marker construct may be co-transformed with the desired construct, as many transformation techniques introduce many DNA molecules into host cells. Typically, transformed hosts are selected for their ability to grow on selective media. Selective media may incorporate an antibiotic or lack a factor necessary for growth of the untransformed host, such as a nutrient or growth factor. An introduced marker gene may confer antibiotic resistance, or encode an essential growth factor or enzyme, thereby permitting growth on selective media when expressed in the transformed host. Selection of a transformed host can also occur when the expressed marker protein can be detected, either directly or indirectly. The marker protein may be expressed alone or as a fusion to another protein. The marker protein can be detected by: 1.) its enzymatic activity (e.g., β-galactosidase can convert the substrate X-gal [5-bromo4-chloro-3-indolyl-β-D-galactopyranoside] to a colored product; luciferase can convert luciferin to a light-emitting product); or 2.) its light-producing or modifying characteristics (e.g., the green fluorescent protein of *Aequorea victoria* fluoresces when illuminated with blue light). Alternatively, antibodies can be used to detect the marker protein or a molecular tag on, for example, a protein of interest. Cells expressing the marker protein or tag can be selected, for example, visually, or by techniques such as FACS or panning using antibodies. For selection of yeast transformants, any marker that functions in yeast may be used. Desirably, resistance to kanamycin, hygromycin and the amino glycoside G418 are of interest, as well as ability to grow on media lacking uracil or leucine.

Following transformation, substrates suitable for the instant Δ12 desaturases (and, optionally other PUFA enzymes that are co-expressed within the host cell) may be produced by the host either naturally or transgenically, or they may be provided exogenously.

Metabolic Engineering of ω-3 and/or ω-6 Fatty Acid Biosynthesis in Microbes

Knowledge of the sequences of the present Δ12 desaturases will be useful for manipulating ω-3 and/or ω-6 fatty acid biosynthesis in oleaginous yeast, and particularly, in *Yarrowia lipolytica*. This may require metabolic engineering directly within the PUFA biosynthetic pathway or additional manipulation of pathways that contribute carbon to the PUFA biosynthetic pathway. Methods useful for manipulating biochemical pathways are well known to those skilled in the art.

Techniques to Up-Requlate Desirable Biosynthetic Pathways

Additional copies of desaturase (and optionally elongase) genes may be introduced into the host to increase the output of ω-3 and/or ω-6 fatty acid biosynthesis pathways, typically through the use of multicopy plasmids. Expression of desaturase and elongase genes also can be increased at the transcriptional level through the use of a stronger promoter (either regulated or constitutive) to cause increased expression, by removing/deleting destabilizing sequences from either the mRNA or the encoded protein, or by adding stabilizing sequences to the mRNA (U.S. Pat. No. 4,910,141). Yet another approach to increase expression of heterologous desaturase or elongase genes is to increase the translational efficiency of the encoded mRNAs by replacement of codons in the native gene with those for optimal gene expression in the selected host microorganism.

Techniques to Down-Regulate Undesirable Biosynthetic Pathways

Conversely, biochemical pathways competing with the ω-3 and/or ω-6 fatty acid biosynthesis pathways for energy or carbon, or native PUFA biosynthetic pathway enzymes that interfere with production of a particular PUFA end-product, may be eliminated by gene disruption or down-regulated by other means (e.g., antisense mRNA). For gene disruption, a foreign DNA fragment (typically a selectable marker gene) is inserted into the structural gene to be disrupted in order to interrupt its coding sequence and thereby functionally inactivate the gene. Transformation of the disruption cassette into the host cell results in replacement of the functional native gene by homologous recombination with the non-functional disrupted gene (See, for example: Hamilton et al. *J. Bacteriol.* 171:4617-4622 (1989); Balbas et al. *Gene* 136:211-213 (1993); Gueldener et al. *Nucleic Acids Res.* 24:2519-2524 (1996); and Smith et al. *Methods Mol. Cell. Biol.* 5:270-277 (1996)).

Antisense technology is another method of down-regulating genes when the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA that encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down-regulating genes where the sequence is known, other less specific methodologies have been developed that are not sequence-based. For example, cells may be exposed to UV radiation and then screened for the desired phenotype. Mutagenesis with chemical agents is also effective for generating mutants and commonly used substances include chemicals that affect nonreplicating DNA (e.g., $HNO_2$ and $NH_2OH$), as well as agents that affect replicating DNA (e.g., acridine dyes, notable for causing frameshift mutations). Specific methods for creating mutants using radiation or chemical agents are well documented in the art. See, for example: Thomas D. Brock in *Biotechnology: A Textbook of Industrial Microbiology*, $2^{nd}$ ed. (1989) Sinauer Associates: Sunderland, Mass.; or Deshpande, Mukund V., *Appl. Biochem. Biotechnol.*, 36: 227 (1992).

Another non-specific method of gene disruption is the use of transposable elements or transposons. Transposons are genetic elements that insert randomly into DNA but can be later retrieved on the basis of sequence to determine where the insertion has occurred. Both in vivo and in vitro transposition methods are known. Both methods involve the use of a transposable element in combination with a transposase enzyme. When the transposable element or transposon is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available [see, for example: 1.) The Primer Island Transposition Kit, available from Perkin Elmer Applied Biosystems, Branchburg, N.J., based upon the yeast Ty1 element; 2.) The Genome Priming System, available from New England Biolabs, Beverly, Mass., based upon the bacterial transposon Tn7; and 3.) the EZ::TN Transposon Insertion Systems, available from Epicentre Technologies, Madison, Wis., based upon the Tn5 bacterial transposable element].

Within the context of the present invention, it may be useful to modulate the expression of the fatty acid biosynthetic pathway by any one of the methods described above. For example, the present invention provides genes (i.e., Δ12 desaturases) encoding key enzymes in the biosynthetic pathways leading to the production of ω-3 and/or ω-6 fatty acids. It will be particularly useful to express these genes in oleaginous yeast that produce insufficient amounts of 18:2 fatty acids and to modulate the expression of this and other PUFA biosynthetic genes to maximize production of preferred PUFA products using various means for metabolic engineering of the host organism. Likewise, to maximize PUFA production with these genes, it may be necessary to disrupt pathways that compete for the carbon flux directed toward PUFA biosynthesis.

In alternate embodiments, it may be desirable to disrupt the Δ12 desaturase herein, to prevent synthesis of ω-3 and/or ω-6 fatty acids. In another alternate embodiment it will be possible to regulate the production of ω-3 and/or ω-6 fatty acids by placing any of the present Δ12 desaturase genes under the control of an inducible or regulated promoter.

Preferred Microbial Hosts for Recombinant Expression of Δ12 Desaturases

Host cells for expression of the instant genes and nucleic acid fragments may include microbial hosts that grow on a variety of feedstocks, including simple or complex carbohydrates, organic acids and alcohols, and/or hydrocarbons over a wide range of temperature and pH values. Although the genes described in the instant invention have been isolated for expression in an oleaginous yeast, and in particular *Yarrowia lipolytica*, it is contemplated that because transcription, translation and the protein biosynthetic apparatus is highly conserved, any bacteria, yeast, algae and/or filamentous fungus will be a suitable host for expression of the present nucleic acid fragments.

Preferred hosts are oleaginous organisms, such as oleaginous yeast. These oleaginous organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodospordium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

Most preferred is the oleaginous yeast *Yarrowia lipolytica*; and, in a further embodiment, most preferred are the *Yarrowia lipolytica* strains designated as ATCC #76982, ATCC #20362, ATCC #8862, ATCC #18944 and/or LGAM S(7)1 (Papanikolaou S., and Aggelis G., *Bioresour. Technol.* 82(1): 43-9 (2002)).

Other preferred microbial hosts include oleaginous bacteria, algae and other fungi (e.g., *Thraustochytrium* sp., *Schizochytrium* sp. and *Mortierella* sp.).

Fermentation Processes for PUFA Production

The transformed microbial host cell is grown under conditions that optimize activity of fatty acid biosynthetic genes and produce the greatest and the most economical yield of fatty acids (e.g., LA, which can in turn increase the production of various ω-3 and/or ω-6 fatty acids). In general, media conditions that may be optimized include the type and amount of carbon source, the type and amount of nitrogen source, the carbon-to-nitrogen ratio, the oxygen level, growth temperature, pH, length of the biomass production phase, length of the oil accumulation phase and the time of cell harvest. Microorganisms of interest, such as oleaginous yeast, are grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources may include, but are not limited to: monosaccharides (e.g., glucose, fructose), disaccharides (e.g., lactose or sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, barley malt). Additionally, carbon sources may include alkanes, fatty acids, esters of fatty acids, monoglycerides, diglycerides, triglycerides, phospholipids and various commercial sources of fatty acids including vegatable oils (e.g., soybean oil) and animal fats. Additionally, the carbon substrate may include one-carbon substrates (e.g., carbon dioxide or methanol) for which metabolic conversion into key biochemical intermediates has been demonstrated. Hence it is contemplated that the source of carbon utilized in the present invention may encompass a wide variety of carbon-containing substrates and will only be limited by the choice of the host organism. Although all of the above mentioned carbon substrates and mixtures thereof are expected to be suitable in the present invention, preferred carbon substrates are sugars and/or fatty acids. Most preferred is glucose and/or fatty acids containing between 10-22 carbons.

Nitrogen may be supplied from an inorganic (e.g., $(NH_4)_2SO_4$) or organic source (e.g., urea or glutamate). In addition to appropriate carbon and nitrogen sources, the fermentation media must also contain suitable minerals, salts, cofactors, buffers, vitamins, and other components known to those skilled in the art, suitable for the growth of the microorganism and promotion of the enzymatic pathways necessary for PUFA production. Particular attention is given to several metal ions (e.g., $Mn^{+2}$, $Co^{+2}$, $Zn^{+2}$, $Mg^{+2}$).that promote synthesis of lipids and PUFAs (Nakahara, T. et al. *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.0 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast. In this approach, the first stage of the fermentation is dedicated to the generation and accumulation of cell mass and is characterized by rapid cell growth and cell division. In the second stage of the fermentation, it is preferable to establish conditions of nitrogen deprivation in the culture to promote high levels of lipid accumulation. The effect of this nitrogen deprivation is to reduce the effective concentration of AMP in the cells, thereby reducing the activity of the NAD-dependent isocitrate dehydrogenase of mitochondria. When this occurs, citric acid will accumulate, thus forming abundant pools of acetyl-CoA in the cytoplasm and priming fatty acid synthesis. Thus, this phase is characterized by the cessation of cell division followed by the synthesis of fatty acids and accumulation of oil.

Although cells are typically grown at about 30° C., some studies have shown increased synthesis of unsaturated fatty acids at lower temperatures (Yongmanitchai and Ward, *Appl. Environ. Microbiol.* 57:419-25 (1991)). Based on process economics, this temperature shift should likely occur after the first phase of the two-stage fermentation, when the bulk of the organisms' growth has occurred.

It is contemplated that a variety of fermentation process designs may be applied, where commercial production of omega fatty acids using the instant Δ12 desaturase genes is desired. For example, commercial production of PUFAs from a recombinant microbial host may be produced by a batch, fed-batch or continuous fermentation process.

A batch fermentation process is a closed system wherein the media composition is set at the beginning of the process and not subject to further additions beyond those required for maintenance of pH and oxygen level during the process. Thus, at the beginning of the culturing process the media is inoculated with the desired organism and growth or metabolic activity is permitted to occur without adding additional substrates (i.e., carbon and nitrogen sources) to the medium. In batch processes the metabolite and biomass compositions of the system change constantly up to the time the culture is terminated. In a typical batch process, cells moderate through a static lag phase to a high-growth log phase and finally to a stationary phase, wherein the growth rate is diminished or halted. Left untreated, cells in the stationary phase will eventually die. A variation of the standard batch process is the fed-batch process, wherein the substrate is continually added to the fermentor over the course of the fermentation process. A fed-batch process is also suitable in the present invention. Fed-Batch processes are useful when catabolite repression is apt to inhibit the metabolism of the cells or where it is desirable to have limited amounts of substrate in the media at any one time. Measurement of the substrate concentration in fed-batch systems is difficult and therefore may be estimated on the basis of the changes of measurable factors such as pH, dissolved oxygen and the partial pressure of waste gases (e.g., $CO_2$). Batch and fed-batch culturing methods are common and well known in the art and examples may be found in Thomas D. Brock in *Biotechnology: A Textbook of Industrial Microbiology*, $2^{nd}$ ed., (1989) Sinauer Associates: Sunderland, Mass.; or Deshpande, Mukund V., *Appl. Biochem. Biotechnol.*, 36:227 (1992), herein incorporated by reference.

Commercial production of omega fatty acids using the instant Δ12 desaturases may also be accomplished by a continuous fermentation process wherein a defined media is continuously added to a bioreactor while an equal amount of culture volume is removed simultaneously for product recovery. Continuous cultures generally maintain the cells in the log phase of growth at a constant cell density. Continuous or semi-continuous culture methods permit the modulation of one factor or any number of factors that affect cell growth or end product concentration. For example, one approach may limit the carbon source and allow all other parameters to moderate metabolism. In other systems, a number of factors affecting growth may be altered continuously while the cell concentration, measured by media turbidity, is kept constant. Continuous systems strive to maintain steady state growth and thus the cell growth rate must be balanced against cell loss due to media being drawn off the culture. Methods of modulating nutrients and growth factors for continuous culture processes, as well as techniques for maximizing the rate of product formation, are well known in the art of industrial microbiology and a variety of methods are detailed by Brock, supra.

Purification of PUFAs

The PUFAs may be found in the host microorganism as free fatty acids or in esterified forms such as acylglycerols, phospholipids, sulfolipids or glycolipids, and may be extracted from the host cell through a variety of means well-known in the art. One review of extraction techniques, quality analysis and acceptability standards for yeast lipids is that of Z. Jacobs (*Critical Reviews in Biotechnology* 12(5/6):463-491 (1992)). A brief review of downstream processing is also available by A. Singh and O. Ward (*Adv. Appl. Microbiol.* 45:271-312 (1997)).

In general, means for the purification of PUFAs may include extraction with organic solvents, sonication, supercritical fluid extraction (e.g., using carbon dioxide), saponification, and physical means such as presses, or combinations thereof. Of particular interest is extraction with methanol and chloroform in the presence of water (E. G. Bligh & W. J. Dyer, Can. *J. Biochem. Physiol.* 37:911-917 (1959)). Where desirable, the aqueous layer can be acidified to protonate negatively-charged moieties and thereby increase partitioning of desired products into the organic layer. After extraction, the organic solvents can be removed by evaporation under a stream of nitrogen. When isolated in conjugated forms, the products may be enzymatically or chemically cleaved to release the free fatty acid or a less complex conjugate of interest, and can then be subject to further manipulations to produce a desired end product. Desirably, conjugated forms of fatty acids are cleaved with potassium hydroxide.

If further purification is necessary, standard methods can be employed. Such methods may include extraction, treatment with urea, fractional crystallization, HPLC, fractional distillation, silica gel chromatography, high-speed centrifugation or distillation, or combinations of these techniques. Protection of reactive groups, such as the acid or alkenyl groups, may be done at any step through known techniques (e.g., alkylation or iodination). Methods used include methylation of the fatty acids to produce methyl esters. Similarly, protecting groups may be removed at any step. Desirably, purification of fractions containing GLA, STA, ARA, DHA and EPA may be accomplished by treatment with urea and/or fractional distillation.

DESCRIPTION OF PREFERRED EMBODIMENTS

The ultimate goal of the work described herein is the development of an oleaginous yeast that accumulates oils enriched in ω-3 and/or ω-6 PUFAs. Toward this end, desaturases must be identified that function efficiently in oleaginous yeast, to enable synthesis and high accumulation of preferred PUFAs in these hosts. Identification of efficient desaturases is also necessary for the manipulation of the ratio of ω-3 to ω-6 PUFAs produced in host cells.

In previous work, the Applicants have isolated the native *Yarrowia lipolytica* Δ12 desaturase and over-expressed this protein, resulting in increased conversion of oleic acid to LA with respect to the wildtype cells (U.S. patent application Ser. No. 10/840,325, incorporated entirely by reference; see also Example 2 herein and SEQ ID NOs:51 and 52). Specifically, the percent substrate conversion (measured as ([18:2]/[18:1+18:2])*100) was 74% in the transformed cells, as opposed to a percent substrate conversion of only 59% in wildtype *Yarrowia*. Despite the observed increase in LA availability within these host cells, however, it was desirable to identify genes encoding proteins with Δ12 desaturase activity that would enable even greater conversion of oleic acid to LA. This would permit increased availability of LA as a substrate for high-level synthesis of a variety of ω-3 and/or ω-6 PUFAs within the *Y. lipolytica* transformant cells (e.g., GLA, DGLA, ARA, ALA, STA, ETA, EPA, DPA and DHA). Thus, expression of a heterologous protein having high-level Δ12 desaturase activity was therefore advantageous in the pathway engineering of the organism.

To achieve these goals, in the present invention Applicants have isolated and cloned a DNA fragment from *Fusarium moniliforme* that encodes a Δ12 desaturase enzyme (SEQ ID NOs:3 and 4). Confirmation of this gene's activity as a Δ12 desaturase was provided based upon: 1.) restoration of LA biosynthesis (via complementation) upon expression of the *Fusarium moniliforme* gene in a *Yarrowia lipolytica* strain in which the native Δ12 desaturase gene was disrupted; and 2.)

over-production of LA in wild type *Y. lipolytica* cells expressing the *F. moniliforme* gene (Example 6).

The experimentation described above led to a surprising discovery, however, wherein the *F. moniliforme* Δ12 desaturase was more efficient than the *Yarrowia lipolytica* Δ12 desaturase in producing 18:2 in *Yarrowia lipolytica* (see Example 6, Table 11). Specifically, expression of the *F. moniliforme* Δ12 desaturase under the control of the TEF promoter in *Yarrowia lipolytica* was determined to produce higher levels of 18:2 (68% product accumulation of LA) than were previously attainable by expression of a chimeric gene encoding the *Yarrowia lipolytica* Δ12 desaturase under the control of the TEF promoter (59% product accumulation of LA). This corresponds to a difference in percent substrate conversion (calculated as ([18:2]/[18:1+18:2])*100) of 85% versus 74%, respectively. Furthermore, the *F. moniliforme* Δ12 desaturase functioned much more efficiently than previous reports for any known Δ12 desaturase (e.g., only 68% substrate conversion of oleic acid to 18:2 was achieved upon overexpression of the *Neurospora crassa* Δ12 desaturase in *S. cerevisiae* [WO 2003/099216]).

On the basis of these results, expression of the present fungal *F. moniliforme* Δ12 desaturase is preferred relative to other known Δ12 desaturases as a means to engineer an oleaginous yeast that accumulates oils enriched in ω-3 and/or ω-6 PUFAs (however, one skilled in the art would expect that the activity of the *F. moniliforme* Δ12 desaturase could be enhanced in *Yarrowia lipolytica*, following e.g., codon-optimization).

Additionally, Applicants have also identified a suite of Δ12 desaturases orthologous to the *Fusarium moniliforme* protein described above from *Aspergillus nidulans, Magnaporthe grisea, Neurospora crassa, Fusarium graminearium, Aspergillus fumigatus* and *Aspergillus flavus* (i.e., SEQ ID NOs:8, 12, 16, 20, 21 and 22). These proteins (including the *Fusarium moniliforme* Δ12 desaturase (SEQ ID NO:4)) clustered within a distinct sub-family of proteins (referred to herein as "Sub-family 2") that are well-distinguished from the proteins clustered within "Sub-family 1" (i.e., SEQ ID NOs:2, 6, 10,14 and 18, identified in co-pending U.S. Provisional Application 60/519,191 as Δ15 desaturases), despite all proteins' identification as homologous to the *Y. lipolytica* Δ12 desaturase identified herein as SEQ ID NO:52 (characterized in co-pending U.S. patent application Ser. No. 10/840, 325). Together, the proteins of sub-family 2 (identified herein as Δ12 desaturases and supported by the functional characterization of the *Neurospora crassa* protein as a Δ12 desaturase in WO 03/099216) represent a group of proteins having at least 56.3% identity to one another (Example 4) and they are well-distinguished by sequence homology from previously described Δ12 desaturases.

It is expected that this unique class of fungal Δ12 desaturases will be useful for expression in oleaginous yeast (e.g., *Yarrowia lipolytica*) as a means to alter the fatty acid composition, based on the expectation that they will function with high efficiency (i.e., percent substrate conversion, wherein % substrate conversion of oleic acid to LA of at least about 70% is preferred, while a % substrate conversion to LA of at least about 80% is particularly suitable, and a % substrate conversion to LA of at least about 85% is most preferred). Thus, one embodiment of the invention is a method of altering fatty acid profiles in an oleaginous yeast, whereby a Δ12 desaturase protein of sub-family 2 is expressed alone or in combination with other fatty acid biosynthetic genes (e.g., a Δ4 desaturase, a Δ5 desaturase, a Δ6 desaturase, a Δ12 desaturase, a Δ15 desaturase, a Δ17 desaturase, a Δ9 desaturase, a Δ8 desaturase and/or an elongase).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: 1.) Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, Experiments with Gene Fusions; Cold Spring Harbor Laboratory: Cold Spring Harbor, N.Y. (1984); and 3.) Ausubel, F. M. et al., Current Protocols in Molecular Biology, published by Greene Publishing Assoc. and Wiley-Interscience (1987).

Materials and methods suitable for the maintenance and growth of bacterial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in *Biotechnology: A Textbook of Industrial Microbiology* $2^{nd}$ ed., Sinauer Associates: Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified.

*E. coli* TOP10 cells and *E. coli* Electromax DH10B cells were obtained from Invitrogen (Carlsbad, Calif.). Max Efficiency competent cells of *E. coli* DH5α were obtained from GIBCO/BRL (Gaithersburg, Md.). *E. coli* (XL1-Blue) competent cells were purchased from the Stratagene Company (San Diego, Calif.). All *E. coli* strains were typically grown at 37° C. on Luria Bertani (LB) plates.

General molecular cloning was performed according to standard methods (Sambrook et al., supra). Oligonucleotides were synthesized by Sigma-Genosys (Spring, Tex.). PCR products were cloned into Promega's pGEM-T-easy vector (Madison, Wis.).

DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNASTAR Inc., Madison, Wis.).

The meaning of abbreviations is as follows: "sec" means second(s), "min" means minute(s), "h" means hour(s), "d" means day(s), "μl" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Cultivation of *Yarrowia lipolytica*

*Yarrowia lipolytica* strains ATCC #76982 and ATCC #90812 were purchased from the American Type Culture Collection (Rockville, Md.). *Y. lipolytica* strains were usually grown at 28° C. on YPD agar (1% yeast extract, 2% bactopeptone, 2% glucose, 2% agar). For transformation selection, minimal medium (0.17% yeast nitrogen base (DIFCO Laboratories, Detroit, Mich.) without ammonium sulfate and without amino acids, 2% glucose, 0.1% proline, pH 6.1) was used. Supplements of adenine, leucine, lysine and/or uracil were added as appropriate to a final concentration of 0.01%.

Fatty Acid Analysis of *Yarrowia lipolytica*

For fatty acid analysis, cells were collected by centrifugation and lipids were extracted as described in Bligh, E. G. & Dyer, W. J. (Can. *J. Biochem. Physiol.* 37:911-917 (1959)). Fatty acid methyl esters were prepared by transesterification of the lipid extract with sodium methoxide (Roughan, G., and Nishida I. *Arch Biochem Biophys.* 276(1):3846 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 μl of 1%) was added to the sample, and then the sample was vortexed and rocked for 20 min. After adding 3 drops of 1 M NaCl and 400 μl hexane, the sample was vortexed and spun. The upper layer was removed and analyzed by GC as described above.

Example 1

Construction of *Yarrowia* Expression Vectors

The present Example describes the construction of plasmid pY5, pY5-13 (comprising a chimeric TEF promoter::XPR terminator gene), and pY5-20 (comprising a chimeric hygromycin resistance gene).

Construction of Plasmid pY5

The plasmid pY5, a derivative of pINA532 (a gift from Dr. Claude Gaillardin, Insitut National Agronomics, Centre de biotechnologie Agro-Industrielle, laboratoire de Genetique Moleculaire et Cellularie INRA-CNRS, F-78850 Thiverval-Grignon, France), was constructed for expression of heterologous genes in *Yarrowia lipolytica* (FIG. 3).

First, the partially-digested 3598 bp EcoRI fragment containing the ARS18 sequence and LEU2 gene of pINA532 was subcloned into the EcoRI site of pBluescript (Strategene, San Diego, Calif.) to generate pY2. The TEF promoter (Muller S., et al. *Yeast,* 14: 1267-1283 (1998)) was amplified from *Yarrowia lipolytica* genomic DNA by PCR using TEF5' (SEQ ID NO:23) and TEF3' (SEQ ID NO:24) as primers. PCR amplification was carried out in a 50 μl total volume containing: 100 ng *Yarrowia* genomic DNA, PCR buffer containing 10 mM KCl, 10 mM $(NH_4)_2SO_4$, 20 mM Tris-HCl (pH 8.75), 2 mM $MgSO_4$, 0.1% Triton X-100, 100 μg/mL BSA (final concentration), 200 μM each deoxyribonucleotide triphosphate, 10 pmole of each primer and 1 μl of PfuTurbo DNA polymerase (Stratagene, San Diego, Calif.). Amplification was carried out as follows: initial denaturation at 95° C. for 3 min, followed by 35 cycles of the following: 95° C. for 1 min, 56° C. for 30 sec, 72° C. for 1 min. A final extension cycle of 72° C. for 10 min was carried out, followed by reaction termination at 4° C. The 418 bp PCR product was ligated into pCR-Blunt to generate pIP-tef. The BamHI/EcoRV fragment of pIP-tef was subcloned into the BamHI/SmaI sites of pY2 to generate pY4.

The XPR2 transcriptional terminator was amplified by PCR using pINA532 as template and XPR5' (SEQ ID NO:25) and XPR3' (SEQ ID NO:26) as primers. The PCR amplification was carried out in a 50 μl total volume, using the components and conditions described above. The 179 bp PCR product was digested with SacII and then ligated into the SacII site of pY4 to generate pY5. Thus, pY5 (shown in FIG. 3) is useful as a *Yarrowia-E. coli* shuttle plasmid containing:

1.) a *Yarrowia* autonomous replication sequence (ARS18);
2.) a ColE1 plasmid origin of replication;
3.) an ampicillin-resistance gene (AmpR), for selection in *E. coli;*
4.) a *Yarrowia* LEU2 gene, for selection in *Yarrowia;*
5.) the translation elongation promoter (TEF P), for expression of heterologous genes in *Yarrowia;* and
6.) the extracellular protease gene terminator (XPR2) for transcriptional termination of heterologous gene expression in *Yarrowia.*

Construction of Plasmids PY5-13 and pY5-20 pY5-13 and pY5-20 were constructed as derivatives of pY5 to faciliate subcloning and heterologous gene expression in *Yarrowia lipolytica.*

Specifically, pY5-13 was constructed by 6 rounds of site-directed mutagenesis using pY5 as template. Both SalI and ClaI sites were eliminated from pY5 by site-directed mutagenesis using oligonucleotides YL5 and YL6 (SEQ ID NOs:27 and 28) to generate pY5-5. A SalI site was introduced into pY5-5 between the Leu2 gene and the TEF promoter by site-directed mutagenesis using oligonucleotides YL9 and YL10 (SEQ ID NOs:29 and 30) to generate pY5-6. A PacI site was introduced into pY5-6 between the LEU2 gene and ARS18 using oligonucleotides YL7 and YL8 (SEQ ID NOs: 31 and 32) to generate pY5-8. An NcoI site was introduced into pY5-8 around the translation start codon of the TEF promoter using oligonucleotides YL3 and YL4 (SEQ ID NOs: 33 and 34) to generate pY5-9. The NcoI site inside the Leu2 gene of pY5-9 was eliminated using YL1 and YL2 oligonucleotides (SEQ ID NOs:35 and 36) to generate pY5-12. Finally, a BsiWI site was introduced into pY5-12 between the ColEI and XPR region using oligonucleotides YL61 and YL62 (SEQ ID NOs:37 and 38) to generate pY5-13.

Plasmid pY5-20 is a derivative of pY5. It was constructed by inserting a Not I fragment containing a chimeric hygromycin resistance gene into the Not I site of pY5. The chimeric gene had the hygromycin resistance ORF under the control of the *Yarrowia lipolytica* TEF promoter.

Example 2

Cloning of the *Yarrowia lipolytica* Δ12 Desaturase and Disruption of the Endogenous Δ12 Desaturase Gene Based on the fatty acid composition of *Yarrowia lipolytica* (ATCC #76982) which demonstrated that the organism could make LA (18:2) but not ALA (18:3), it was assumed that *Y. lipolytica* would likely contain gene(s) having Δ12 desaturase activity but not Δ15 desaturase activity. Thus, the present Example describes the use of degenerate PCR primers to isolate a partial coding sequence of the *Yarrowia lipolytica*

Δ12 desaturase, the use of the partial sequence to disrupt the native gene in *Yarrowia lipolytica*, and subsequent cloning of the full-length gene.

Cloning of a Partial Putative Δ12 Desaturase Sequence from *Yarrowia lipolytica* by PCR Using Degenerate PCR Primers Genomic DNA was isolated from *Yarrowia lipolytica* (ATCC #76982) using DNeasy Tissue Kit (Qiagen, Catalog #69504) and resuspended in kit buffer AE at a DNA concentration of 0.5 μg/μl. PCR amplifications were performed using the genomic DNA as template and several sets of degenerate primers made to amino acid sequences conserved between different Δ12 desaturases. The best results were obtained with a set of upper and lower degenerate primers, P73 and P76, respectively, as shown in the Table below.

TABLE 4

Degenerate Primers Used For Amplification Of A Partial Putative Δ12 Desaturase

| Primer Set | Description | Degenerate Nucleotide Sequence | Corresponding Amino Acid Sequence |
|---|---|---|---|
| P73 | (32) 26-mers | 5'-TGGGTCCTGGGCCA YGARTGYGGNCA-3' (SEQ ID NO:39) | WVLGHECGH (SEQ ID NO:40) |
| P76 | (64) 30-mers | 5'-GGTGGCCTCCTCGGC (M/I)PFVHAEEAT GTGRTARAANGGNAT-3' (SEQ ID NO:41) | (SEQ ID NO:42) |

[Note: Abbreviations are standard for nucleotides and proteins. The nucleic acid degereracy code used is as follows: R = A/G; Y = C/T; and N = A/C/G/T.]

The PCR was carried out in an Eppendorf Mastercycler Gradient thermocycler according to the manufacturer's recommendations. Amplification was carried out as follows: initial denaturation at 95° C. for 1 min, followed by 30 cycles of denaturation at 95° C. for 30 sec, annealing at 58° C. for 1 min, and elongation at 72° C. for 1 min. A final elongation cycle at 72° C. for 10 min was carried out, followed by reaction termination at 4° C.

The expected (ca. 740 bp) size PCR product was detected by agarose gel electrophoresis, isolated, purified, cloned into a pTA vector (Invitrogen), and sequenced. The resultant sequence had homology to known Δ12 desaturases, based on BLAST program analysis (Basic Local Alignment Search Tool; Altschul, S. F., et al., *J. Mol. Biol.* 215:403-410 (1993)).

Targeted Disruption of *Yarrowia lipolytica* Δ12 Desaturase Gene

Targeted disruption of the Δ12 desaturase gene in *Yarrowia lipolytica* ATCC #76982 was carried out by homologous recombination-mediated replacement of the Δ12 desaturase gene with a targeting cassette designated as pY23D12. pY23D12 was derived from plasmid pY20 (Example 1).

Specifically, pY23D12 was created by inserting a Hind III/Eco RI fragment into similarly linearized pY20. This 642 bp fragment consisted of (in 5' to 3' orientation): 3' homologous sequence from position +718 to +1031 (of the coding sequence (ORF) in SEQ ID NO:51), a Bgl II restriction site, and 5' homologous sequence from position +403 to +717 (of the coding sequence (ORF) in SEQ ID NO:51). The fragment was prepared by PCR amplification of 3' and 5' sequences from the 642 bp PCR product using sets of PCR primers P99 and P100 (SEQ ID NOs:43 and 44) and P101 and P102 (SEQ ID NOs:45 and 46), respectively.

pY23D12 was linearized by Bgl II restriction digestion and transformed into mid-log phase *Y. lipolytica* ATCC #76982 cells by the lithium acetate method according to the method of Chen, D. C. et al. (*Appl Microbiol Biotechnol.* 48(2):232-235 (1997)). Briefly, *Y. lipolytica* was streaked onto a YPD plate and grown at 30° C. for approximately 18 hr. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and 50 μg sheared salmon sperm DNA.

About 500 ng of plasmid DNA was incubated in 100 μl of resuspended cells, and maintained at 39° C. for 1 hr with vortex mixing at 15 min intervals. The cells were plated onto YPD hygromycin selection plates and maintained at 30° C. for 2 to 3 days.

Four hygromycin-resistant colonies were isolated and screened for targeted disruption by PCR. One set of PCR primers (P119 [SEQ ID NO:47] and P120 [SEQ ID NO:48]) was designed to amplify a specific junction fragment following homologous recombination. Another set of PCR primers (P121 [SEQ ID NO:49] and P122 [SEQ ID NO:50]) was designed to detect the native gene. Three of the four hygromycin-resistant colonies were positive for the junction fragment and negative for the native fragment, thus confirming targeted integration.

Determination of Fatty Acid Profile in the Δ12 Desaturase-Disrupted Strain

Disruption of the native Δ12 desaturase gene was further confirmed by GC analysis of the total lipids in one of the disrupted strains, designated as Q-d12D. Single colonies of wild type (ATCC #76982) and Q-d12D were each grown in 3 mL minimal media (formulation/L: 20 g glucose, 1.7 g yeast nitrogen base, 1 g L-proline, 0.1 g L-adenine, 0.1 g L-lysine, pH 6.1) at 30° C. to an $OD_{600}$~1.0. The cells were harvested, washed in distilled water, speed vacuum dried and subjected to direct trans-esterification and GC analysis (as described in the General Methods).

The fatty acid profile of wildtype *Yarrowia* and the transformant Q-d12D comprising the disrupted Δ12 desaturase are shown below in Table 5. Fatty acids are identified as 16:0 (palmitate), 16:1 (palmitoleic acid), 18:0,18:1 (oleic acid) and 18:2 (LA) and the composition of each is presented as a % of the total fatty acids.

TABLE 5

Fatty Acid Composition (% Of Total Fatty Acids) In Wildtype And Transformant *Yarrowia lipolytica*

| Strain | 16:0 | 16:1 | 18:0 | 18:1 | 18:2 |
|---|---|---|---|---|---|
| Wild type | 11 | 14 | 2 | 33 | 34 |
| Q-d12D disrupted | 6 | 15 | 1 | 74 | nd |

*nd = not detectable

Results indicated that the native Δ12 desaturase gene in the Q-d12D strain was inactivated. Thus, it was possible to conclude that there was only one gene encoding a functional Δ12 desaturase in *Yarrowia lipolytica* ATCC #76982.

Plasmid Rescue of the *Yarrowia lipolytica* Δ12 Desaturase Gene

Since the Δ12 desaturase gene was disrupted by the insertion of the entire pY23D12 vector that also contained an *E. coli* ampicillin-resistant gene and *E. coli* ori, it was possible to rescue the flanking sequences in *E. coli*. For this, genomic DNA of *Yarrowia lipolytica* strain Q-d12D was isolated using the DNeasy Tissue Kit. Specifically, 10 μg of the genomic DNA was digested with 50 μl of restriction enzymes Age I, Avr II, Nhe I and Sph I in a reaction volume of 200 μl. Digested DNA was extracted with phenol:chloroform and resuspended in 40 μl deionized water. The digested DNA (10 μl) was self-ligated in 200 μl ligation mixture containing 3 U T4 DNA ligase. Ligation was carried out at 16° C. for 12 hrs. The ligated DNA was extracted with phenol:chloroform and resuspended in 40 μl deionized water. Finally, 1 μl of the resuspended ligated DNA was used to transform E. coli by electroporation and plated onto LB plates containing ampicillin (Ap). Ap-resistant colonies were isolated and analyzed for the presence of plasmids by miniprep. The following insert sizes were found in the recovered or rescued plasmids (Table 6):

TABLE 6

Insert Sizes Of Recovered Plasmids, According To Restriction Enzyme

| Enzyme | plasmid insert size (kB) |
|---|---|
| AgeI | 1.6 |
| AvrII | 2.5 |
| NheI | 9.4 |
| SphI | 6.6 |

Sequencing of the plasmids was initiated with sequencing primers P99 (SEQ ID NO:43) and P102 (SEQ ID NO:46).

Based on the sequencing results, a full-length gene encoding the *Yarrowia lipolytica* Δ12 desaturase gene was assembled (1936 bp; SEQ ID NO:51). Specifically, the sequence encoded an open reading frame of 1257 bases (nucleotides +283 to +1539 of SEQ ID NO:51), while the deduced amino acid sequence was 419 residues in length (SEQ ID NO:52). This gene was also also publically disclosed as YALI-CDS3053.1 within the public *Y. lipolytica* protein database of the "Yeast project Genolevures" (Center for Bioinformatics, LaBRI, Talence Cedex, France) (see also Dujon, B. et al., *Nature* 430 (6995):35-44 (2004)).

Example 3

Expression of *Yarrowia lipolytica* Δ12 Desaturase ORF Under the Control of a Heterologous *Yarrowia* Promoter The present Example describes the expression of the *Y. lipolytica* Δ12 desaturase ORF (from Example 2) in a chimeric gene under the control of a heterologous (non-Δ12 desaturase) *Yarrowia* promoter. This enabled complementation of the Δ12 desaturase-disrupted mutant and overproduction of LA in the wildtype *Y. lipolytica* strain.

Specifically, the ORF encoding the *Y. lipolytica* Δ12 desaturase was PCR amplified using upper primer P147 (SEQ ID NO:53) and lower primer P148 (SEQ ID NO:54) from the genomic DNA of *Y. lipolytica* ATCC #76982. The correct sized (1260 bp) fragment was isolated, purified, digested with Nco I and Not I and cloned into NcoI-NotI cut pY5-13 vector (Example 1), such that the gene was under the control of the TEF promoter. Correct transformants were confirmed by miniprep analysis and the resultant plasmid was designated pY25-d12d.

Plasmids pY5-13 (the "control") and pY25-d12d were each individually transformed into *Y. lipolytica* ATCC #76982 wild-type (WT) and Δ12-disrupted strains (Q-d12D), using the transformation method described in Example 2. Positive transformants were selected on Bio101 DOB/CSM-Leu plates.

Single colonies of transformants were grown up and GC analyzed as described in the General Methods. Results are shown in the Table below. Fatty acids are identified as 16:0 (palmitate), 16:1 (palmitoleic acid), 18:0,18:1 (oleic acid) and 18:2 (LA); and the composition of each is presented as a % of the total fatty acids. "D12d SC" was calculated according to the following formula: ([18:2]/[18:1+18:2])*100 and represents percent substrate conversion (SC).

TABLE 7

Fatty Acid Composition (% Of Total Fatty Acids) Of *Yarrowia lipolytica* Transformed With *Yarrowia lipolytica* Δ12 Desaturase Gene

| Strain | Plasmid | % 16:0 | % 16:1 | % 18:0 | % 18:1 | % 18:2 | D12d SC |
|---|---|---|---|---|---|---|---|
| Q-d12D | pY5-13 | 8 | 10 | 2 | 80 | nd | 0 |
| Q-d12D | pY25-d12d | 11 | 8 | 2 | 34 | 45 | 57 |
| WT | pY5-13 | 10 | 10 | 1 | 32 | 47 | 59 |
| WT | pY25-d12d | 12 | 7 | 2 | 21 | 59 | 74 |

*nd = not detectable

The results showed that expression of *Y. lipolytica* Δ12 desaturase using the TEF promoter restores production of 18:2 in the strain with the endogenous gene disrupted.

Additionally, the results demonstrated that overexpression of the *Y. lipolytica* Δ12 desaturase gene in wild type cells resulted in increased levels of LA production (18:2). Specifically, the % product accumulation of LA increased from 47% in wild type cells to 59% in transformant cells (representing a change in the percent substrate conversion ["D12d SC"] from 59% in the wild type to 74% in those cells transformed with the chimeric Δ12 desaturase).

Example 4

Identification of Δ12 Desaturases from Filamentous Fungi

The present Example describes the identification of Δ12 desaturases in various filamentous fungi. These sequences were identified based on their homology to the *Yarrowia lipolytica* Δ12desaturase (Example 2); and, the sequences from each species fell into one of two "sub-families" based on phylogenetic analyses.

BLAST searches (Basic Local Alignment Search Tool; Altschul, S. F., et al., *J. Mol. Biol.* 215:403410 (1993)) were conducted using the *Yarrowia lipolytica* Δ12 desaturase protein sequence (SEQ ID NO:52) as a query against available sequence databases of filamentous fungi, including: 1.) public databases of *Neurospora crassa, Magnaporthe grisea, Aspergillus nidulans* and *Fusarium graminearium*; and 2.) a DuPont EST library of *Fusarium moniliforme* strain M-8114 (E.I. du Pont de Nemours and Co., Inc., Wilmington, Del.) (*F. moniliforme* strain M-8114 available from the Fusarium Research Center, University Park, Pa.; see also *Plant Disease* 81(2): 211-216 (1997)). These BLAST searches resulted in the identification of two homologs to the *Yarrowia lipolytica* Δ12 desaturase protein within each organism. The Table below summarizes details concerning each of these homologs.

TABLE 8

Description Of ORFs Having Homology To The *Yarrowia lipolytica* Δ12 Desaturase

| SEQ ID NOs* | Source | Abbreviation | Organism |
|---|---|---|---|
| 1, 2 | EST sequence database, E. I. duPont de Nemours and Co., Inc. | Fm1 or Fm d15 | *Fusarium moniliforme* |
| 3, 4 | EST sequence database, E. I. duPont de Nemours and Co., Inc. | Fm2 or Fm d12 | *Fusarium moniliforme* |
| 5, 6 | Contig 1.122 (scaffold 9) in the *A. nidulans* genome project (sponsored by the Center for Genome Research (CGR), Cambridge, MA); see also WO 2003/099216 | An1 or An d15 | *Aspergillus nidulans* |
| 7, 8 | Contig 1.15 (scaffold 1) in the *A. nidulans* genome project; AAG36933 | An2 or An d12 | *Aspergillus nidulans* |
| 9, 10 | Locus MG08474.1 in contig 2.1597 in the *M. grisea* genome project (sponsored by the CGR and International Rice Blast Genome Consortium) | Mg1 or Mg d15 | *Magnaporthe grisea* |
| 11, 12 | Locus MG01985.1 in contig 2.375 in the *M. grisea* genome project | Mg2 or Mg d12 | *Magnaporthe grisea* |
| 13, 14 | GenBank Accession No. AABX01000577); see also WO 2003/099216 | Nc1 or Nc d15 | *Neurospora crassa* |
| 15, 16 | GenBank Accession No. AABX01000374; see also WO 2003/099216 | Nc2 or Nc d12 | *Neurospora crassa* |
| 17, 18 | Contig 1.320 in the *F. graminearium* genome project (sponsored by the CGR and the International *Gibberella zeae* Genomics Consortium (IGGR); BAA33772.1) | Fg1 or Fg d15 | *Fusarium graminearium* |
| 19, 20 | Contig 1.233 in the *F. graminearium* genome project | Fg2 or Fg d12 | *Fusarium graminearium* |

*Note: Odd SEQ ID NOs refer to ORF nucleotide sequences and even SEQ ID NOs refer to the deduced amino acid sequences.

All of the homologs were either unannotated or annotated as a Δ12 desaturase or fatty acid desaturase. Furthermore, the nucleotide sequences from *F. graminearium* were genomic with putative intron sequences; the Applicants made a tentative assembly of the deduced amino acids for comparison with amino acid sequences from the other homologs.

Figure 4:
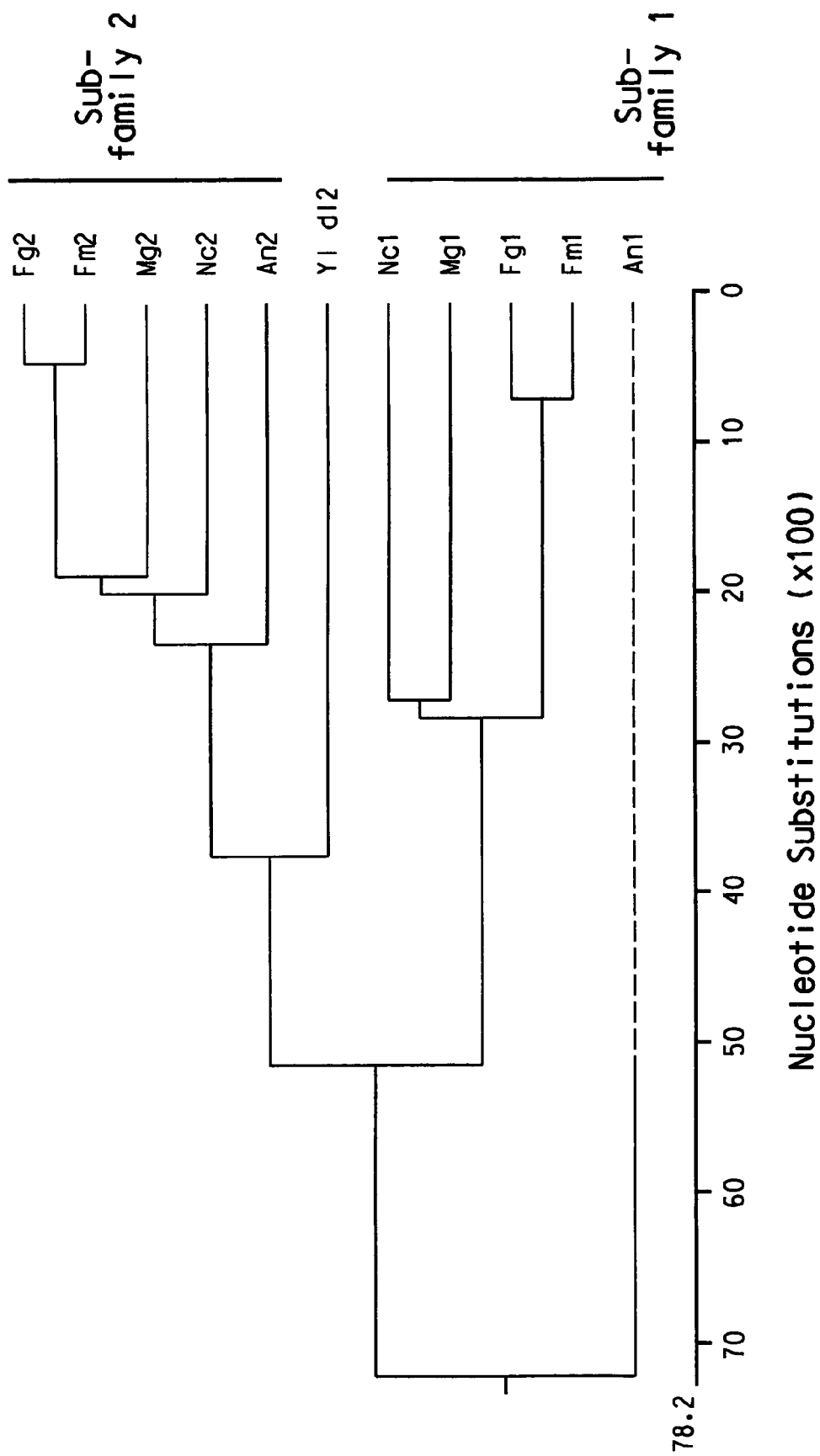
FIG. 4 shows a phylogenetic tree of proteins from different filamentous fungi (i.e., *Aspergillus nidulans, Fusarium moniliforme, F. graminearium, Magnaporthe grisea* and *Neurospora crassa*) having homology to the *Yarrowia lipolytica* Δ12 desaturase enzyme, and created using Megalign DNASTAR software.

Phylogenetic tree analysis of the Δ12 desaturase homologs from each species using the Megalign program of the LASERGENE bioinformatics computing suite (Windows 32 Megalign 5.06 1993-2003; DNASTAR Inc., Madison, Wis.) unexpectedly revealed two sub-families. As shown in FIG. 4, Nc1, Mg1, Fg1, Fm1 and An1 clustered in "sub-family 1" of the proteins having homology to the *Yarrowia lipolytica* Δ12 desaturase while Fg2, Fm2, Mg2, Nc2 and An2 clustered within "sub-family 2" of the Yarrowia lipolytica Δ12 desaturase protein homologs.

Subsequently, a single Δ12 desaturase homolog was also identified in public sequence databases for two additional organisms, as shown below in Table 9.

TABLE 9

Additional ORFs Having Homology To The *Yarrowia lipolytica* Δ12 Desaturase

| SEQ ID NO | Source | Symbol | Organism |
|---|---|---|---|
| 21 | AFA.133c 344248:345586 reverse (AfA5C5.001c) in the *Aspergillus fumigatus* genome project (sponsored by Sanger Institute, collaborators at the University of Manchester, and The Institute of Genome Research (TIGR)) | Af d12 | *Aspergillus fumigatus* |
| 22 | GenBank Accession No. AY280867 (VERSION AY280867.1; GI: 30721844) | — | *Aspergillus flavus* |

These additional sequences clustered within sub-family 2 of the Yarrowia lipolytica Δ12desaturase protein homologs.

Each of the proteins having homology to the *Yarrowia lipolytica* Δ12desaturase were then aligned using the method of Clustal W (slow, accurate, Gonnet option; Thompson et al., *Nucleic Acids Res.* 22:4673-4680 (1994)) of the Megalign program of DNASTAR software. The percent identities revealed by this method were used to determine whether the proteins were orthologs (FIG. 5). In addition, the homologs were compared to the known Δ12 desaturases shown below in Table 10 (FIG. 6).

TABLE 10

Known Δ12 Desaturases Used In Clustal W Analysis

| FIG. 6 Ref. No. | Symbol | Description | GenBank Accession No. |
|---|---|---|---|
| 1 | Sp d12 | *Spiruline platensis* Δ12 desaturase | X86736 |
| 2 | Ce d12 | *Caenorhabditis elegans* Δ12 desaturase | AF240777 |
| 3 | Cr d12 | *Chlamydomonas reinhardtii* Δ12 desaturase | AB007640 |
| 4 | Cv d12 | *Chlorella vulgaris* Δ12 desaturase | AB075526 |
| 5 | AtM d12 | *Arabidopsis thaliana* microsomal Δ12 desaturase | AP002063 |
| 6 | Yl d12 | *Yarrowia lipolytica* Δ12 desaturase (SEQ ID NO: 52 herein) | YALI-CDS3053.1 within the public *Y. lipolytica* protein database of the "Yeast project Genolevures" (Center for Bioinformatics, LaBRI, Talence Cedex, France) (see also Dujon, B. et al., Nature 430 (6995): 35-44 (2004)); see also U.S. Patent Application No. 10/840325 |
| 7 | Dh d12 | *Debaryomyces hansenii* Δ12 desaturase | >Ctg0330-0000227-2.1 (see "Yeast project Genolevures") |
| 8 | MaA d12 | *Mortierella alpina* Δ12 desaturase | >gi\|6448794\|gb\|AAF08684.1\| AF110509_1 |
| 9 | Mr d12 | *Mucor rouxii* Δ12 desaturase | AF161219 |
| 10 | Pa d12 | *Pichia augusta* Δ12 desaturase | >Ctg1334- 0000001-1.1. (see "Yeast project Genolevures") |

The proteins of sub-family 1 (SEQ ID NOs:2, 6, 10, 14 and 18; FIG. 5) were at least 46.2% identical to each other and were less than 45.2% identical to the proteins of sub-family 2 (SEQ ID NOs:4, 8, 12, 16, 20; FIG. 5). Furthermore, the proteins of sub-family 2 (SEQ ID NOs:4, 8, 12, 16, 20; FIG. 5) were at least 56.3% identical to each other. The maximum identity between the proteins of sub-family 2 and the Δ12 desaturases from *S. platensis, C. elegans, C. reinhardtii, C. vulgaris, A. thaliana, Y. lipolytica, D. hansenii, M. alpina, M. rouxii,* and *P. augusta* is 51.6% (FIG. 6).

Although not shown in FIG. 5 or FIG. 6, the *Aspergillus flavus* Δ12 desaturase homolog (SEQ ID NO:22) was similarly compared to the other proteins of sub-family 2 (SEQ ID NOs:4, 8, 12, 16, 20 and 21) using the method of Clustal W (supra). The following results were obtained:

79% protein identity of *Aspergillus flavus* against *A. fumigatus,* 68.5% protein identity against *N. crassa,* 60.9% protein identity against *F. graminearium,* 61.8% protein identity against *F. moniliforme,* 66.1% protein identity against *M. grisea* and 76% protein identity against *A. nidulans.* Thus, based on the homologies in FIGS. 5 and 6 and those presented above, the *F. moniliforme* Δ12desaturase (SEQ ID NO:4) was at least 56.3% identical to the remaining Δ12 desaturase proteins of sub-family 2 (herein defined as SEQ ID NOs:4, 8, 12, 16, 20, 21 and 22), based on the homology between the *F. moniliforme* and *M. grisea* protein sequences.

The analyses above clearly differentiated the two sub-families of proteins having homology to the *Yarrowia lipolytica* Δ12 desaturase (SEQ ID NO:52). Additionally, it was known that yeast such as *Y. lipolytica* can only synthesize 18:2 (but not 18:3), while each of the five filamentous fungi are able to synthesize both 18:2 and 18:3. Furthermore, a single Δ12 desaturase was isolated from *Yarrowia,* while most of the fungi had two homologs to the *Yarrowia* Δ12 desaturase. Thus, the Applicants postulated that one of the sub-families of desaturases in these organisms represented a Δ12 desaturase (permitting conversion of oleic acid to LA (18:2)) and the other represented a Δ15 desaturase (permitting conversion of LA to ALA (18:3)).

Example 5

Construction of Expression Plasmid pY35 (TEF::Fm2), Comprising the Fusarium moniliforme Desaturase of Sub-Family 2 (Encoding a Putative Δ12 Desaturase)

The present Example describes the construction of an expression plasmid comprising the Fusarium moniliforme Δ12 desaturase of sub-family 2 ("Fm2" or "Fm d12") identified in Example 4. Specifically, a chimeric gene was created, such that the putative Δ12 desaturase would be expressed under the control of the *Yarrowia* TEF promoter. This would enable subsequent determination of the protein's activity in *Yarrowia lipolytica,* by testing the ability of the expressed ORF to confer LA production in the wild type strain and to complement a Δ12 desaturase-disrupted mutant (infra, Example 6).

The ORF encoding the *F. moniliforme* Δ12 desaturase was PCR amplified using the cDNA clones ffm2c.pK007.g13 and ffm2c.pk001.p18 containing the full-length cDNA as the template and using upper and lower primers P194 (SEQ ID NO:55) and P195 (SEQ ID NO:56). The PCR was carried out in an Eppendorf Mastercycler Gradient Cycler using TA Taq and pfu polymerases, per the manufacturer's recommendations. Amplification was carried out as follows: initial denaturation at 95° C. for 1 min, followed by 30 cycles of denaturation at 95° C. for 30 sec, annealing at 58° C. for 1 min, and elongation at 72° C. for 1 min. A final elongation cycle at 72° C. for 10 min was carried out, followed by reaction termination at 4° C.

The correct-sized (ca. 1441 bp) fragment was obtained from both templates. The fragment was purified from an agarose gel using a Qiagen DNA purification kit, digested with NcoI and NotI and cloned into NcoI and NotI cut pY25-d12d (Example 3), thereby replacing the *Yarrowia* Δ12 desaturase ORF in the TEF::Yl D12d chimeric gene. This resulted in creation of a 8571 bp plasmid designated as pY35, which contained a TEF::Fm2 chimeric gene (as opposed to the *Yarrowia* Δ12 desaturase). Plasmid pY35 additionally contained the *E. coli* origin of replication, the bacterial ampicillin resistance gene, *Yarrowia* Leu 2 gene and the *Yarrowia* autonomous replication sequence (ARS).

Example 6

Expression of Plasmid DY35 (TEF::Fm2), Comprising the *Fusarium moniliforme* Desaturase of Sub-Family 2 (Encoding a Putative Δ12 Desaturase) In *Yarrowia lipolytica*

The present Example describes expression of plasmid pY35 (comprising the chimeric TEF::Fm2 gene; from Example 5) in *Yarrowia lipolytica.* Specifically, the ability of the expressed *F. moniliforme* ORF comprising the putative Δ12 desaturase was tested for its ability to confer LA production in the wild type strain of *Y. lipolytica* and to complement the Δ12 desaturase-disrupted mutant (from Example 2).

Plasmids pY5 (vector alone control, from Example 1), pY25-d12d (TEF::YI D12d, the "positive control" from Example 3), and pY35 (TEF::Fm2) were each individually transformed into wild type (WT) and Δ12 desaturase-disrupted (Q-d12D) strains of *Yarrowia lipolytica* ATCC #76892, using the transformation procedure described in Example 2. Transformant cells were selected on Bio101 DOB/CSM-Leu plates.

Single colonies of wild type and transformant cells were each grown in 3 mL minimal media, harvested, washed, dried and analyzed, as described in Example 2 and the General Methods.

The fatty acid profile of wildtype *Yarrowia* and each of the transformants are shown below in Table 11 (results obtained from two experiments). Fatty acids are identified as 16:0 (palmitate), 16:1 (palmitoleic acid), 18:0, 18:1 (oleic acid), 18:2 (LA) and 18:3 (ALA) and the composition of each is presented as a % of the total fatty acids. "d12d SC" was calculated according to the following formula: ([18:2]/[18:1+18:2])*100 and represents percent substrate conversion to 18:2.

TABLE 11

Confirmation Of The *Fusarium moniliforme* Fm2 ORF's Δ12 Desaturase Activity When Expressed In *Yarrowia lipolytica*

| strain | % 16:0 | % 16:1 | % 18:0 | % 18:1 | % 18:2 | % ALA | d12d % SC |
|---|---|---|---|---|---|---|---|
| WT | 11 | 11 | 2 | 33 | 39 | 0.0 | 55 |
| WT + pY5 (vector alone) | 9 | 25 | 0 | 32 | 35 | 0.0 | 52 |
| WT + TEF::Fm2 | 12 | 5 | 1 | 12 | 68 | 0.4 | 85 |
| Q-d12D | 6 | 11 | 1 | 80 | 0 | 0.0 | 0 |
| Q-d12D + TEF::Fm2 | 10 | 6 | 1 | 27 | 53 | 0.3 | 67 |

The results above demonstrated that the *F. moniliforme* ORF referred to herein as Fm2, and identified as a protein within sub-family 2 of those proteins having homology to the *Yarrowia lipolytica* Δ12 desaturase, is a Δ12 desaturase. Based on this confirmation, the Applicants predict that all other members of sub-family 2 (SEQ ID NOs:8, 12, 16, 20, 21 and 22) also will have Δ12 desaturase functionality.

Additionally, the results demonstrated that, unexpectedly, the *Fusarium moniliforme* Δ12 desaturase (Fm2) is even more efficient in its activity in *Yarrowia* than the native *Y. lipolytica* Δ12 desaturase. Specifically, comparison of the data in Table 11 to that of Table 7 (Example 3) reveals a percent substrate conversion (SC) of 85% in WT+TEF::Fm2 cells versus only 74% in WT+TEF::YI D12d cells. Likewise, the percent substrate conversion in Q-d12D+TEF::Fm2 cells was 67%, while the percent substrate conversion was only 57% in Q-d12D+TEF::YI D12d cells. Thus, it would be expected that expression of the *Fusarium moniliforme* Δ12 desaturase, in combination of other genes for PUFA biosynthesis (e.g., a Δ6 desaturase, elongase, Δ5 desaturase, Δ17 desaturase, Δ9 desaturase, Δ4 desaturase, Δ8 desaturase, Δ15 desaturase), would result in higher production of ω-3 and ω-6 PUFAs than would result using the native *Y. lipolytica* Δ12 desaturase.

Example 7

Production of DGLA in *Yarrowia lipolytica* Using Chimeric Genes Constructed with the *Fusarium moniliforme* Δ12 Desaturase Construct pKUNF12T6E (FIG. 7; SEQ ID NO:57) was generated to integrate four chimeric genes (comprising the *Fusarium moniliforme* Δ12 desaturase, a Δ6 desaturase and 2 elongases) into the Ura3 loci of wild type *Yarrowia* strain ATCC #20362, to thereby enable production of DGLA. The pKUNF12T6E plasmid contained the following components:

TABLE 12

Description of Plasmid pKUNF12T6E (SEQ ID NO: 57)

| RE Sites And Nucleotides Within SEQ ID NO: 57 | Description Of Fragment And Chimeric Gene Components |
|---|---|
| AscI/BsiWI (9420-8629) | 784 bp 5' part of *Yarrowia* Ura3 gene (GenBank Accession No. AJ306421) |
| SphI/PacI (12128-1) | 516 bp 3' part of *Yarrowia* Ura3 gene (GenBank Accession No. AJ306421) |
| SwaI/BsiWI (6380-8629) | FBAIN::EL1S: Pex20, comprising: FBAIN: FBAIN promoter (SEQ ID NO: 58; see co-pending U.S. Patent Application No. 60/519971, describing a fructose-bisphosphate aldolase enzyme promoter) EL1S: codon-optimized elongase 1 gene (SEQ ID NO: 59), derived from *Mortierella alpina* (GenBank Accession No. AX464731) Pex20: Pex20 terminator sequence from *Yarrowia* Pex20 gene (GenBank Accession No. AF054613) |
| BglII/SwaI (4221-6380) | TEF::Δ6S::Lip1, comprising: TEF: TEF promoter (GenBank Accession No. AF054508) Δ6S: codon-optimized Δ6 desaturase gene (SEQ ID NO: 61), derived from *Mortierella alpina* (GenBank Accession No. AF465281) Lip1: Lip1 terminator sequence from *Yarrowia* Lip1 gene (GenBank Accession No. Z50020) |
| PmeI/ClaI (4207-1459) | FBA::F.Δ12::Lip2, comprising: FBA: FBA promoter (SEQ ID NO: 63; see co-pending U.S. Patent Application No. 60/519971 describing a fructose-bisphosphate aldolase enzyme promoter) F.Δ12: *Fusarium moniliforme* Δ12 desaturase gene (SEQ ID NO: 3) Lip2: Lip2 terminator sequence from *Yarrowia* Lip2 gene (GenBank Accession No. AJ012632) |
| ClaI/PacI (1459-1) | TEF::EL2S::XPR, comprising: TEF: TEF promoter (GenBank Accession No. AF054508) EL2S: codon-optimized elongase gene (SEQ ID NO: 64), derived from *Thraustochytrium aureum* (U.S. Pat. No. 6,677,145) XPR: XPR terminator sequence of *Yarrowia* Xpr gene (GenBank Accession No. M17741) |

The pKUNF12T6E plasmid was digested with AscI/SphI, and then used for transformation of wild type *Y. lipolytica* ATCC #20362 (as described in Example 2). The transformant cells were plated onto 5-fluorouracil-6-carboxylic acid monohydrate ("FOA") selection media plates (0.17% yeast nitrogen base (DIFCO Laboratories, Detroit, Mich.) without ammonium sulfate or amino acids, 2% glucose, 0.1% proline, 75 mg/L uracil, 75 mg/L uridine, 20 g/L agar and 800 mg/L FOA (Zymo Research Corp., Orange, Calif. 92867)) and maintained at 30° C. for 2 to 3 days. The FOA resistant colonies were picked and streaked onto selection plates comprising either minimal media (20 g/L glucose, 1.7 g/L yeast nitrogen base without amino acids, 1 g/L L-proline, 0.1 g/L L-adenine, 0.1 g/L L-lysine, pH 6.1) or minimal media plus 0.01% uracil ("MMU"). The colonies that could grow on MMU plates but not on the minimal media plates were selected as Ura-strains. Single colonies of Ura-strains were then inoculated into liquid MMU at 30° C. and shaken at 250 rpm/min for 2 days.

GC analyses (as described in the General Methods) showed the presence of DGLA in the transformants containing the 4 chimeric genes of pKUNF12T6E, but not in the wild type Yarrowia control strain. Most of the selected 32 Ura⁻ strains produced about 6% DGLA of total lipids. There were 2 strains that produced about 8% DGLA of total lipids.

Example 8

Synthesis of a Codon-Optimized Δ12 Desaturase Gene for Expression in *Yarrowia lipolytica*

A codon-optimized Δ12 desaturase gene will be designed, based on the *Fusarium moniliforme* DNA sequence (SEQ ID NO:3), according to the *Yarrowia* codon usage pattern, the consensus sequence around the ATG translation initiation codon, and the general rules of RNA stability (Guhaniyogi, G. and J. Brewer, *Gene* 265(1-2):11-23 (2001)).

Determining the Preferred Codon Usage in *Yarrowia lipolytica*

Codon usage in *Yarrowia lipolytica* is shown in Table 13. It is based on the coding region of approximately 100 genes of *Y. lipolytica* found in the National Center for Biotechnology Information public database. The coding regions of these genes, comprising 121,167 bp, were translated by the Editseq program of DNAStar to the corresponding 40,389 amino acids and were tabulated to determine the *Y. lipolytica* codon usage profile shown in Table 13. The column titled "No." refers to the number of times a given codon encodes a particular amino acid in the sample of 40,389 amino acids. The column titled "%" refers to the frequency that a given codon encodes a particular amino acid. Entries shown in bold text represent the codons favored in *Yarrowia lipolytica*.

TABLE 13

Codon Usage In *Yarrowia lipolytica*

| Codon | Amino Acid | No. | % |
|---|---|---|---|
| GCA | Ala (A) | 359 | 11.4 |
| GCC | Ala (A) | 1523 | 48.1 |
| GCG | Ala (A) | 256 | 8.1 |
| GCU | Ala (A) | 1023 | 32.3 |
| AGA | Arg (R) | 263 | 13.2 |
| AGG | Arg (R) | 91 | 4.6 |
| CGA | Arg (R) | 1133 | 56.8 |
| CGC | Arg (R) | 108 | 5.4 |
| CGG | Arg (R) | 209 | 1.0 |
| CGU | Arg (R) | 189 | 9.5 |
| AAC | Ans (N) | 1336 | 84.0 |

TABLE 13-continued

Codon Usage In *Yarrowia lipolytica*

| Codon | Amino Acid | No. | % |
|---|---|---|---|
| AAU | Ans (N) | 255 | 16.0 |
| GAC | Asp (D) | 1602 | 66.8 |
| GAU | Asp (D) | 795 | 33.2 |
| UGC | Cys (C) | 268 | 53.2 |
| UGU | Cys (C) | 236 | 46.8 |
| CAA | Gln (Q) | 307 | 17.0 |
| CAG | Gln (Q) | 1490 | 83.0 |
| GAA | Glu (E) | 566 | 23.0 |
| GAG | Glu (E) | 1893 | 77.0 |
| GGA | Gly (G) | 856 | 29.7 |
| GGC | Gly (G) | 986 | 34.2 |
| GGG | Gly (G) | 148 | 5.1 |
| GGU | Gly (G) | 893 | 31.0 |
| CAC | His (H) | 618 | 65.5 |
| CAU | His (H) | 326 | 34.5 |
| AUA | Ile (I) | 42 | 2.1 |
| AUC | Ile (I) | 1106 | 53.7 |
| AUU | Ile (I) | 910 | 44.2 |
| CUA | Leu (L) | 166 | 4.7 |
| CUC | Leu (L) | 1029 | 29.1 |
| CUG | Leu (L) | 1379 | 38.9 |
| CUU | Leu (L) | 591 | 16.7 |
| UUA | Leu (L) | 54 | 1.5 |
| UUG | Leu (L) | 323 | 9.1 |
| AAA | Lys (K) | 344 | 14.8 |
| AAG | Lys (K) | 1987 | 85.2 |
| AUG | Met (M) | 1002 | 100 |
| UUC | Phe (F) | 996 | 61.1 |
| UUU | Phe (F) | 621 | 38.9 |
| CCA | Pro (P) | 207 | 9.6 |
| CCC | Pro (P) | 1125 | 52.0 |
| CCG | Pro (P) | 176 | 8.2 |
| CCU | Pro (P) | 655 | 30.2 |
| AGC | Ser (S) | 335 | 11.3 |
| AGU | Ser (S) | 201 | 6.8 |
| UCA | Ser (S) | 221 | 7.5 |
| UCC | Ser (S) | 930 | 31.5 |

TABLE 13-continued

Codon Usage In *Yarrowia lipolytica*

| Codon | Amino Acid | No. | % |
|---|---|---|---|
| UCG | Ser (S) | 488 | 16.5 |
| UCU | Ser (S) | 779 | 26.4 |
| UAA | Term | 38 | 46.9 |
| UAG | Term | 30 | 37.0 |
| UGA | Term | 13 | 16.1 |
| ACA | Thr (T) | 306 | 12.7 |
| ACC | Thr (T) | 1245 | 51.6 |
| ACG | Thr (T) | 269 | 11.1 |
| ACU | Thr (T) | 595 | 24.6 |
| UGG | Trp (W) | 488 | 100 |
| UAC | Tyr (Y) | 988 | 83.2 |
| UAU | Tyr (Y) | 200 | 16.8 |
| GUA | Val (V) | 118 | 4.2 |
| GUC | Val (V) | 1052 | 37.3 |

TABLE 13-continued

Codon Usage In *Yarrowia lipolytica*

| Codon | Amino Acid | No. | % |
|---|---|---|---|
| GUG | Val (V) | 948 | 33.6 |
| GUU | Val (V) | 703 | 24.9 |

The synthetic, codon-optimized Δ12 desaturase is made by methods known to one skilled in the art.

For further optimization of gene expression in *Y. lipolytica*, the consensus sequence around the 'ATG' initiation codon of 79 genes was examined. Seventy seven percent of the genes analyzed had an 'A' in the −3 position (with the first 'A' of the translation initiation codon (ATG) labeled as +1), indicating a strong preference for 'A' at this position. There was also preference for 'A' or 'C' at the −4, −2 and −1 positions, an 'A', 'C' or 'T' at position +5, and a 'G' or 'C' at position +6. Thus, the preferred consensus sequence of the codon-optimized translation initiation site for optimal expression of genes in *Y. lipolytica* is 'MAMMATGNHS' (SEQ ID NO:66), wherein the nucleic acid degeneracy code used is as follows: M=A/C; S=C/G; H=A/C/T; and N=A/C/G/T.

One skilled in the art would readily be able to use the information provided above to synthesize a codon-optimized Δ12 desaturase gene, based on the *Fusarium moniliforme* Δ12 desaturase sequence provided herein.

What is claimed is:

1. An isolated nucleic acid fragment encoding a fungal Δ12 desaturase enzyme, encoding the amino acid sequence as set forth in SEQ ID NO:4;

or, an isolated nucleic acid fragment that is complementary to over the full length of the isolated nucleic acid sequence encoding the amino acid sequence as set forth in SEQ ID NO:4.

2. The isolated nucleic acid fragment of claim 1 as set forth in SEQ ID NO:3.

3. The isolated nucleic acid fragment of claim 1 isolated from *Fusarium moniliforme*.

4. A chimeric gene comprising the isolated nucleic acid fragment of claim 1 operably linked to suitable regulatory sequences.

5. A method for the production of linoleic acid comprising:
   (a) providing an oleaginous yeast comprising:
      (i) the isolated nucleic acid fragment according to claim 1; and
      (ii) a source of oleic acid;
   (b) growing the yeast of step (a) under conditions wherein the nucleic acid fragment encoding a polypeptide having Δ12 desaturase activity is expressed and the oleic acid is converted to linoleic acid; and
   (c) optionally recovering the linoleic acid of step (b).

6. A method for the production of polyunsaturated fatty acids comprising:
   (a) providing an oleaginous yeast comprising:
      (i) the isolated nucleic acid fragment of claim 1; and
      (ii) genes encoding a functional ω-3/ω-6 fatty acid biosynthetic pathway;
   (b) providing a source of desaturase substrate comprising oleic acid; and
   (c) growing the oleaginous yeast of step (a) with the desaturase substrate of (b) under conditions wherein polyunsaturated fatty acids are produced; and
   (d) optionally recovering the polyunsaturated fatty acids of step (c).

* * * * *